United States Patent
Ritter et al.

(10) Patent No.: US 10,759,764 B2
(45) Date of Patent: Sep. 1, 2020

(54) FLUORINATION OF ORGANIC COMPOUNDS

(71) Applicant: President and Fellows of Harvard College, Cambridge, MA (US)

(72) Inventors: Tobias Ritter, Cambridge, MA (US); Constanze Nicole Neumann, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 101 days.

(21) Appl. No.: 15/029,602

(22) PCT Filed: Oct. 17, 2014

(86) PCT No.: PCT/US2014/061066
§ 371 (c)(1),
(2) Date: Apr. 14, 2016

(87) PCT Pub. No.: WO2015/058047
PCT Pub. Date: Apr. 23, 2015

(65) Prior Publication Data
US 2016/0272593 A1    Sep. 22, 2016

Related U.S. Application Data

(60) Provisional application No. 62/037,418, filed on Aug. 14, 2014, provisional application No. 61/895,254, filed on Oct. 24, 2013, provisional application No. 61/892,935, filed on Oct. 18, 2013.

(51) Int. Cl.
| | |
|---|---|
| *C07D 233/70* | (2006.01) |
| *C07B 59/00* | (2006.01) |
| *A61K 51/04* | (2006.01) |
| *C07C 309/04* | (2006.01) |
| *C07D 233/84* | (2006.01) |

(52) U.S. Cl.
CPC .......... *C07D 233/70* (2013.01); *A61K 51/04* (2013.01); *C07B 59/00* (2013.01); *C07B 59/001* (2013.01); *C07B 59/007* (2013.01); *C07C 309/04* (2013.01); *C07D 233/84* (2013.01); *C07B 2200/05* (2013.01)

(58) Field of Classification Search
None
See application file for complete search history.

(56) References Cited

U.S. PATENT DOCUMENTS

| | | |
|---|---|---|
| 3,136,774 A | 6/1964 | Stoffel |
| 3,136,776 A | 6/1964 | Stoffel |
| 3,137,701 A | 6/1964 | Ayer |
| 3,641,153 A | 2/1972 | Kyburz et al. |
| 3,972,936 A | 8/1976 | Christy |
| 3,991,103 A | 11/1976 | Barton et al. |
| 4,236,008 A | 11/1980 | Henderson |
| 4,402,956 A | 9/1983 | Silvestrini et al. |
| 4,487,773 A | 12/1984 | Temple, Jr. et al. |
| 4,578,222 A | 3/1986 | Ishikawa et al. |
| 6,069,110 A | 5/2000 | Klaui et al. |
| 6,127,583 A | 10/2000 | Sonoda et al. |
| 6,160,158 A | 12/2000 | Bartlett et al. |
| 7,108,846 B1 | 9/2006 | Marchand et al. |
| 7,115,249 B2 | 10/2006 | Luthra et al. |
| 8,686,158 B2 | 4/2014 | Furuya et al. |
| 9,024,093 B2 | 5/2015 | Ritter et al. |
| 9,150,516 B2 | 10/2015 | Ritter et al. |
| 9,273,083 B2 | 3/2016 | Ritter et al. |
| 2005/0085474 A1 | 4/2005 | Ebenbeck et al. |
| 2005/0137421 A1 | 6/2005 | Walsh et al. |
| 2006/0083677 A1 | 4/2006 | Brady et al. |
| 2007/0092441 A1 | 4/2007 | Wadsworth et al. |
| 2009/0247517 A1 | 10/2009 | Liu et al. |
| 2011/0054175 A1 | 3/2011 | Ritter et al. |
| 2011/0212936 A1 | 9/2011 | Furuya et al. |
| 2011/0312903 A1 | 12/2011 | Ritter et al. |
| 2012/0095217 A1 | 4/2012 | Ritter et al. |
| 2012/0149900 A1 | 6/2012 | Ritter et al. |
| 2012/0316120 A1 | 12/2012 | Ritter |
| 2012/0316341 A1 | 12/2012 | Ritter |
| 2014/0018538 A1 | 1/2014 | Lee et al. |

(Continued)

FOREIGN PATENT DOCUMENTS

| | | |
|---|---|---|
| CN | 1263882 A | 8/2000 |
| CN | 1897891 A1 | 1/2007 |

(Continued)

OTHER PUBLICATIONS

Maas et al., Dication Ethers. 7[1]. Dication Ether Salts from Cyclic Bisureas. Journal of Heterocyclic Chemistry, 1985, 22, 907-910.*
Burfurd et al., Chalcogeno-urea Ligands on a Phosphadiazonium Lewis Acceptor: A New Synthetic Approach to Ch—P Bonds (Ch=O, S, Se). Inorganic Chemistry 2003, 42, 4949-4954.*
CAPLUS printout of "Burfurd et al., Chalcogeno-urea Ligands on a Phosphadiazonium Lewis Acceptor: A New Synthetic Approach to Ch—P Bonds (Ch=O, S, Se). Inorganic Chemistry 2003, 42, 4949-4954."*
ACS printout of "Burfurd et al., Chalcogeno-urea Ligands on a Phosphadiazonium Lewis Acceptor: A New Synthetic Approach to Ch—P Bonds (Ch=O, S, Se). Inorganic Chemistry 2003, 42, 4949-4954."*

(Continued)

*Primary Examiner* — Po-Chih Chen
(74) *Attorney, Agent, or Firm* — Wolf, Greenfield & Sacks, P.C.

(57) ABSTRACT

Methods for fluorinating organic compounds utilizing a novel organic reagent are described herein. The invention further discloses the utility of this reagent for incorporation of the 18 F isotope into hydroxyl group-containing organic molecules for PET imaging studies. Preparation of the reagents is described along with isolable intermediate structures from reaction of the reagent with a hydroxyl group-containing organic molecule.

30 Claims, 8 Drawing Sheets

(56) References Cited

U.S. PATENT DOCUMENTS

| | | | |
|---|---|---|---|
| 2014/0058106 | A1 | 2/2014 | Ritter et al. |
| 2015/0252067 | A1 | 9/2015 | Ritter et al. |

FOREIGN PATENT DOCUMENTS

| | | |
|---|---|---|
| DE | 23 60 940 A1 | 4/1975 |
| EP | 0 618 491 A1 | 10/1994 |
| EP | 0 915 094 A1 | 5/1999 |
| EP | 1 013 629 A1 | 6/2000 |
| GB | 1 177 525 A | 1/1970 |
| JP | 63-166159 A | 7/1988 |
| JP | 2001-322984 A | 11/2001 |
| WO | WO 03/020732 A2 | 3/2003 |
| WO | WO 2005/063254 A2 | 7/2005 |
| WO | WO 2005/117872 A2 | 12/2005 |
| WO | WO 2006/078752 A2 | 7/2006 |
| WO | WO 2008/081477 A1 | 7/2008 |
| WO | WO 2008/091818 A1 | 7/2008 |
| WO | WO 2009/033751 A2 | 3/2009 |
| WO | WO 2009/100014 A1 | 8/2009 |
| WO | WO 2009/141053 A1 | 11/2009 |
| WO | WO 2009/149347 A1 | 12/2009 |
| WO | WO 2010/059943 A2 | 5/2010 |
| WO | WO 2010/081034 A2 | 7/2010 |
| WO | WO 2010/081036 A2 | 7/2010 |
| WO | WO 2011/006088 A2 | 1/2011 |
| WO | WO 2012/024604 A2 | 2/2012 |
| WO | WO 2012/054782 A2 | 4/2012 |
| WO | WO 2012/142162 A2 | 10/2012 |

OTHER PUBLICATIONS

Stang et al., Dictation Ether Salts, R+-O-R+·2CF3SO3-, from the Reaction of Trifluoromethanesulfonic Anhydride with Activated Ketone. Journal of American Chemical Society, 1981, 103, 4837-4845.*

Chemical Abstract Registry No. 96514-51-7, indexed in the Registry File on STN CAS Online Nov. 16, 1984.*

Chemical Abstract Registry No. 586400-94-4, indexed in the Registry File on STN CAS Online Sep. 16, 2003.*

Invitation to Pay Additional Fees for PCT/US2014/061066 mailed Jan. 12, 2015.

International Search Report and Written Opinion for PCT/US2014/061066, dated May 8, 2015.

International Preliminary Report on Patentability for PCT/US2014/061066, dated Apr. 28, 2016.

Invitation to Pay Additional Fees for PCT/US2013/061968 mailed Jan. 3, 2014.

International Search Report and Written Opinion for PCT/US2013/061968 dated Mar. 7, 2014.

International Preliminary Report on Patentability for PCT/US2013/061968 dated Apr. 9, 2015.

Extended European Search Report for EP 09759505.2 dated Jan. 20, 2012.

International Search Report and Written Opinion for PCT/US2009/046401 dated Sep. 22, 2009.

International Preliminary Report on Patentability for PCT/US2009/046401 dated Dec. 16, 2010.

International Search Report and Written Opinion for PCT/US2009/032855 dated Jun. 8, 2009.

International Preliminary Report on Patentability for PCT/US2009/032855 dated Aug. 12, 2010.

Invitation to Pay Additional Fees for PCT/US2010/041561 mailed Sep. 28, 2010.

International Search Report and Written Opinion for PCT/US2010/041561 dated Jun. 15, 2011.

International Preliminary Report on Patentability for PCT/US2010/041561 dated Jan. 19, 2012.

Extended European Search Report for EP 10729595.8 dated May 22, 2013.

International Search Report and Written Opinion for PCT/US2010/020544 dated Oct. 7, 2010.

International Preliminary Report on Patentability for PCT/US2010/020544 dated Jul. 21, 2011.

Extended European Search Report for EP 09828291.6 dated May 18, 2012.

International Search Report and Written Opinion for PCT/US2009/065339 dated Jul. 12, 2010.

International Preliminary Report on Patentability for PCT/US2009/065339 dated Jun. 3, 2011.

International Search Report and Written Opinion for PCT/US2011/048451 dated Mar. 22, 2012.

International Preliminary Report on Patentability for PCT/US2011/048451 dated Mar. 7, 2013.

Extended European Search Report for EP 11818838.2 dated Dec. 10, 2013.

International Search Report and Written Opinion for PCT/US2012/033125 dated Nov. 9, 2012.

International Preliminary Report on Patentability for PCT/US2012/033125 dated Oct. 24, 2013.

Extended European Search Report for EP 12771755.1 dated Aug. 5, 2014.

Extended European Search Report for EP 10729593.3 dated May 3, 2012.

International Search Report and Written Opinion for PCT/US2010/020540 dated Oct. 6, 2010.

International Preliminary Report on Patentability for PCT/US2010/020540 dated Jul. 21, 2011.

International Search Report and Written Opinion for PCT/US2011/057176 dated May 3, 2012.

International Preliminary Report on Patentability for PCT/US2011/057176 dated May 2, 2013.

International Search Report and Written Opinion for PCT/US2015/28446 dated Jul. 27, 2015.

International Preliminary Report on Patentabilityfor PCT/US2015/28446 dated Nov. 10, 2016.

[No Author Listed] PubChem CID No. 3903. 'Enkephalin, Leucine' (Mar. 25, 2005) [Retrieved from the Internet Sep. 12, 2014: http://pubchem.ncbi.nlm.nih.gov/summary/summary.cgi?cid=3903&loc=ec_rcs#].

[No Author Listed] Wired Chemist. Common Bond Energies (D) and Bond Lengths (r). 2013. Available at http://www.wiredchemist.com/chemistry/data/bond_energies_lengths.html. Last accessed Nov. 18, 2013. 10 pages.

Adams et al., Nucleophilic routes to selectively fluorinated aromatics. Chem Soc Rev. 1999;28:225-31.

Alvarez-Corral et al., Silver-mediated synthesis of heterocycles. Chem Rev. Aug. 2008;108(8):3174-98. doi: 10.1021/cr0783611. Epub Jul. 17, 2008.

Andrae et al., Energy-adjustedab initio pseudopotentials for the second and third row transition elements. Theor Chem Acta. 1990;77(2):123-41.

Andrae et al., Energy-adjustedab initio pseudopotentials for the second and third row transition elements: Molecular test for M2 (M=Ag, Au) and MH (M=Ru, Os). Theor Chim Acta. 1991;78(4):247-66.

Balz et al., Über aromatische Fluorverbindungen, I.: Ein neues Verfahren zu ihrer Darstellung. Ber Deut Chem Ges. 1927;60:1186-90.

Becke, Density-functional thermochemistry. III. The role of exact exchange. J Chem Phys. 1993;98(7): 5648-52.

Berge et al., Pharmaceutical Salts. J. Pharmaceutical Sciences 1977;66:1-19.

Bergman et al., Fluorine-18-labeled fluorine gas for synthesis of tracer molecules. Nucl Med Biol. Oct. 1997;24(7):677-83.

Billingsley et al., Palladium-catalyzed borylation of aryl chlorides: scope, applications, and computational studies. Angew Chem. 2007;119(28):5455-59.

Black et al., Observations on the mechanism of halogen-bridge cleavage by unidentate ligands in square planar palladium and platinum complexes. Australian Journal of Chemistry. 1994;47(2):217-227.

(56) References Cited

OTHER PUBLICATIONS

Bohm et al., Fluorine in medicinal chemistry. Chembiochem. May 3, 2004;5(5):637-43.

Brazier et al., The condensation of alpha-Keto-beta-anilino-alphabeta-diphenyl ethane and its Homologues with phenylcarbimide and with phenylthiocarbimide. J Chem Soc. 1912;101:2352-58.

Brown et al., Transition-metal-mediated reactions for C(sp2)-F bond construction: the state of play. Angew Chem Int Ed Engl. 2009;48(46):8610-4. doi: 10.1002/anie.200902121.

Cámpora et al., Redox Behavior of an Organometallic Palladium(II)/Palladium(IV) System. A New Method for the Synthesis of Cationic Palladium(IV) Complexes. Organometallics. 2005;24(15):3624-3628.

Canty et al., Carbon-Oxygen Bond Formation at Metal(IV) Centers: Reactivity of Palladium(II) and Platinum(II) Complexes of the [2,6-(Dimethylaminomethyl)phenyl-N,C,N]—(Pincer) Ligand toward Iodomethane and Dibenzoyl Peroxide; Structural Studies of M(II) and M(IV) Complexes. Organometallics. 2004;23(23):5432-5439.

Canty et al., Synthesis and Characterization of Ambient Temperature Stable Organopalladium(IV) Complexes, Including Aryl-, .eta. 1-Allyl-, Ethylpalladium(IV), and Pallada(IV)cyclopentane Complexes. Structures of the Poly(pyrazol-1-yl)borate Complexes PdMe3{(pz)3BH} and PdMe3{(pz)4B } and Three Polymorphs of PdMe2Et{(pz)3BH}. Organometallics. 1995;14(1):199-206.

Canty et al., Synthesis of halogeno, pseudohalogeno, and carboxylatopalladium(IV) complexes by halogen exchange. Crystal structure of azido(2,2'-bipyridyl)-benzylpalladium(II), formed on reductive elimination of ethane from Pd(N3)Me2(CH2Ph)(bpy). J Organometallic Chem. 1992;433(1-2):213-22.

Casitas et al., Nucleophilic aryl fluorination and aryl halide exchange mediated by a Cu(I)/Cu(III) catalytic cycle. J Am Chem Soc. Dec. 7, 2011;133(48):19386-92. doi: 10.1021/ja2058567. Epub Nov. 14, 2011.

Chan et al., Palladium(II)-catalyzed selective monofluorination of benzoic acids using a practical auxiliary: a weak-coordination approach. Angew Chem Int Ed Engl. Sep. 19, 2011;50(39):9081-4. doi: 10.1002/anie.201102985. Epub Jul. 11, 2011.

Chuang et al., A dinuclear palladium catalyst for α-hydroxylation of carbonyls with O2. J Am Chem Soc. Feb. 16, 2011;133(6):1760-2. doi: 10.1021/ja108396k. Epub Jan. 19, 2011.

Constaninou et al., Xenon difluoride exchanges fluoride under mild conditions: a simple preparation of [(18)F]xenon difluoride for PET and mechanistic studies. J Am Chem Soc. Feb. 28, 2001;123(8):1780-1.

Cope et al., Electrophilic aromatttic substitution reactions by platinum(II) and palladium(II) chlorides on N,N-dimethylbenzylamines. J Am Chem Soc. 1968;90(4):909-913.

Couturier et al., Fluorinated tracers for imaging cancer with positron emission tomography. Eur J Nucl Med Mol Imaging. Aug. 2004;31(8):1182-206. Epub Jul. 6, 2004.

Danielson et al., Use of 19F NMR to probe protein structure and conformational changes. Annu Rev Biophys Biomol Struct. 1996;25:163-95.

Database Accession No. CID 5255788. Oct. 7, 2005.

Dick et al., A highly selective catalytic method for the oxidative functionalization of C—H bonds. J Am Chem Soc. Mar. 3, 2004;126(8):2300-1.

Dick et al., Carbon-Nitrogen Bond-Forming Reactions of Palladacycles with Hypervalent Iodine Reagents. Organometallics. 2007;26(6):1365-1370.

Dick et al., Unusually stable palladium(IV) complexes: detailed mechanistic investigation of C—O bond-forming reductive elimination. J Am Chem Soc. Sep. 21, 2005;127(37):12790-1.

Edwards et al., In vitro and in vivo studies of neutral cyclometallated complexes against murine leukemias. Canadian Journal of Chemistry. 2005;83(6-7):980-989.

Ehlers et al., A set of f-polarization functions for pseudo-potential basis sets of the transition metals Sc Cu, Y Ag and La Au. Chem Phys Lett. 1993;208(1-2):111-14.

Espinet et al., (CN)-chelate, N,N'-bridged dimeric palladium complexes derived from hydrazones PhC(R):NN'HPh. X-ray structure of [Pd(o-C6H4C(R):NNPh)L]2 [R=Me, L=P(OMe)3]. Inorg Chem., 1989;28(23):4207-4211.

Evans, the determination of the paramagnetic susceptibility of substances in solution by nuclear magnetic resonance. J Chem Soc. 1959;2003-2005.

Fier et al., Copper-mediated fluorination of aryl iodides. J Am Chem Soc. Jul. 4, 2012;134(26):10795-8. doi: 10.1021/ja304410x. Epub Jun. 22, 2012.

Fier et al., Copper-mediated fluorination of arylboronate esters. Identification of a copper(III) fluoride complex. J Am Chem Soc. Feb. 20, 2013;135(7):2552-9. doi: 10.1021/ja310909q. Epub Feb. 5, 2013.

Folgado et al., Fluxionality in hexacoordinated copper(II) complexes with 2,2':6',2"-terpyridine (terpy) and related ligands: structural and spectroscopic investigations. Inorg Chem. 1990;29(11):2035-2042.

Ford et al., Regioselectivity in metallation reactions of 2-(2'-naphthyl)pyridine: 1'-versus 3'-reactivity in mercuration and palladation reactions. Crystal structure of chloro(pyridine) [2-(2-pyridiny)naphthyl-C3,N]palladium. J Organometallic Chem. 1995;493(1-2):215-20.

Fraser et al., Molecular Fluoro Palladium Complexes. J Am Chem Soc. 1997;119(20):4769-70.

Fujimoto et al., PhenoFluor: Practical Synthesis, New Formulation, and Deoxyfluorination of Heteroaromatics. Org Process Res Dev. Aug. 15, 2014;18(8):1041-1044. Epub Jul. 23, 2014.

Furuya et al., Carbon-Fluorine Bond Formation for the Synthesis of Aryl Fluorides. Synthesis. 2010;11:1804-1821.

Furuya et al., Carbon-fluorine bond formation. Curr Opin Drug Discov Devel. Nov. 2008;11(6):803-19.

Furuya et al., Carbon-fluorine reductive elimination from a high-valent palladium fluoride. J Am Chem Soc. Aug. 6, 2008;130(31):10060-1. doi: 10.1021/ja803187x. Epub Jul. 11, 2008.

Furuya et al., Catalysis for fluorination and trifluoromethylation. Nature. May 26, 2011;473(7348):470-7. doi: 10.1038/nature10108.

Furuya et al., Fluorination of boronic acids mediated by silver(I) triflate. Org Lett. Jul. 2, 2009;11(13):2860-3. doi: 10.1021/ol901113t.

Furuya et al., Mechanism of C—F reductive elimination from palladium(IV) fluorides. J Am Chem Soc. Mar. 24, 2010;132(11):3793-807. doi: 10.1021/ja909371t.

Furuya et al., Palladium-mediated fluorination of arylboronic acids. Angew Chem Int Ed Engl. 2008;47(32):5993-6. doi: 10.1002/anie.200802164.

Furuya et al., Silver-mediated fluorination of functionalized aryl stannanes. J Am Chem Soc. Feb. 11, 2009;131(5):1662-3. doi: 10.1021/ja8086664.

Gilicinski et al., On the relative power of electrophilic fluorinating reagents of the N F class. J Fluor Chem. 1992;59(1):157-162.

Grushin et al., Ar—F Reductive Elimination from Palladium(II) Revisited. Organometallics. 2007;26(20):4997-5002.

Grushin et al., Facile Ar-CF3 bond formation at Pd. Strikingly different outcomes of reductive elimination from [(Ph3P)2Pd(CF3)Ph] and [(Xantphos)Pd(CF3)Ph]. J Am Chem Soc. Oct. 4, 2006;128(39):12644-5.

Grushin et al., Is fluoride bonded to two Pd acceptors still basic? Three CH2Cl2 molecules encapsulating a Pd2(mu-F)2 square and new implications for catalysis. Angew Chem Int Ed Engl. Dec. 2, 2002;41(23):4476-9.

Grushin et al., Palladium Fluoride Complexes: One More Step toward Metal-Mediated C—F Bond Formation. Chemistry—A European Journal. 2002;8(5):1006-14.

Gullick et al., Catalytic asymmetric heterogeneous aziridination of styrene using Cu2+-exchanged zeolite Y: effect of the counter-cation on enantioselectivity and on the reaction profile. New J Chem. 2004;28:1470-1478.

Hartwell et al., The formation of palladium(II)- and platinum(II)-carbon bonds by proton abstraction from benzo[h]quinoline and 8-methylquinoline. J Chem Soc D. 1970:912.

Hauchecorne et al., Halogen bonding to a divalent sulfur atom: an experimental study of the interactions of CF3X (X=Cl, Br, I) with

(56) References Cited

OTHER PUBLICATIONS dimethyl sulfide. Phys Chem Chem Phys. Jun. 7, 2011;13(21):10204-13. doi: 10.1039/c0cp02960b. Epub Apr. 20, 2011.

Hayashi et al., 2,2-Difluoro-1,3-dimethylimidazolidine (DFI). A new fluorinating agent. Chem Commun (Camb). Aug. 7, 2002;(15):1618-9. Chem Commun (Camb). Aug. 7, 2002;(15):1618-9.

Henriksen et al., Syntheses, biological evaluation, and molecular modeling of 18F-labeled 4-anilidopiperidines as mu-opioid receptor imaging agents. J Med Chem. Dec. 1, 2005;48(24):7720-32.

Holschumacher et al., Sulfur and Selenium Activation by Frustrated NHC/B(C6F5)3 Lewis Pairs; Conformational Flexibility of Products. Z Naturforsch.. 2011;66b:371-77.

Huang et al., Silver-mediated trifluoromethoxylation of aryl stannanes and arylboronic acids. J Am Chem Soc. Aug. 31, 2011;133(34):13308-10. doi: 10.1021/ja204861a. Epub Aug. 9, 2011.

Hull et al., Palladium-catalyzed fluorination of carbon-hydrogen bonds. J Am Chem Soc. Jun. 7, 2006;128(22):7134-5.

Jasim et al., Contrasting Reactivity of Fluoropyridines at Palladium and Platinum: C—F Oxidative Addition at Palladium, P—C and C—F Activation at Platinum. Organometallics 2004;23(26):6140-49.

Jeschke, The Unique Role of Fluorine in the Design of Active Ingredients for Modern Crop Protection. ChemBioChem. 2004;5(5):570-589.

Julia et al., Orientation de la palladation du noyau naphtalenique dans les α et β dimethylaminomethyl naphtalenes. J Organometallic Chem. 1975;102(2):239-43.

Kamlet et al., Application of palladium-mediated (18)F-fluorination to PET radiotracer development: overcoming hurdles to translation. PLoS One. 2013;8(3):e59187. doi: 10.1371/journal.pone.0059187. Epub Mar. 12, 2013.

Kaspi et al., Xenon difluoride induced aryl iodide reductive elimination: a simple access to difluoropalladium(II) complexes. Inorg Chem. Jan. 7, 2008;47(1):5-7. Epub Dec. 4, 2007.

Khusnutdinova et al., The aerobic oxidation of a Pd(II) dimethyl complex leads to selective ethane elimination from a Pd(III) intermediate. J Am Chem Soc. Feb. 1, 2012;134(4):2414-22. doi: 10.1021/ja210841f. Epub Jan. 20, 2012.

Kilbourn et al., Fluorine-18 labeling of proteins. J Nucl Med. Apr. 1987;28(4):462-70.

Kirk, Fluorination in Medicinal Chemistry: Methods, Strategies, and Recent Developments. Org Process Res Dev. 2008;12(2):305-321.

Laali et al., N-(trifluoromethylsulfonyl)aryloxytrifluoromethylsulfoximines [ArO—So(CF3)=NTf] and N-aryltriflimides Ar—N(Tf)2 by thermal and photolytic dediazoniation of [ArN2] [BF4] in [BMIM] [Tf2N] ionic liquid: exploiting the ambident nucleophilic character of a "nonnucleophilic" anion. J Org Chem. Aug. 31, 2007;72(18):6758-62. Epub Aug. 1, 2007.

Lanci et al., Oxidatively induced reductive elimination from ((t)Bu2bpy)Pd(Me)2: palladium(IV) intermediates in a one-electron oxidation reaction. J Am Chem Soc. Nov. 4, 2009;131(43):15618-20. doi: 10.1021/ja905816q.

Larsen et al., Halogen Complexes. III. The Association of 2,4,6-Trimethylpyridine and Trifluoroiodomethane. J Phys Chem. 1965;69(7):2400-2401.

Lasne et al., Chemistry of beta(+)-emitting compounds based on fluorine-18. In: Contrast Agents II. 2002;222:201-58.

Lee et al., A fluoride-derived electrophilic late-stage fluorination reagent for PET imaging. Science. Nov. 4, 2011;334(6056):639-42. doi: 10.1126/science.1212625.

Lee et al., Nickel-mediated oxidative fluorination for PET with aqueous [18F] fluoride. J Am Chem Soc. Oct. 24, 2012;134(42):17456-8. doi: 10.1021/ja3084797. Epub Oct. 12, 2012.

Li et al., Synthesis and local anesthetic activity of fluoro-substituted imipramine and its analogues. Bioorg Med Chem Lett. Jul. 1, 2007;17(13):3733-5. Epub Apr. 10, 2007.

Liang et al., Introduction of fluorine and fluorine-containing functional groups. Angew Chem Int Ed Engl. Aug. 5, 2013;52(32):8214-64. doi: 10.1002/anie.201206566. Epub Jul. 19, 2013.

Lin et al., Interactions of aziridines with nickel complexes: oxidative-addition and reductive-elimination reactions that break and make C—N bonds. J Am Chem Soc. Mar. 27, 2002;124(12):2890-1.

Liu et al., Oxidative aliphatic C—H fluorination with fluoride ion catalyzed by a manganese porphyrin. Science. Sep. 14, 2012;337(6100):1322-5. doi: 10.1126/science.1222327.

Liu et al., Synthesis and properties of 12-fluororetinal and 12-fluororhodopsin. Model system for fluorine-19 NMR studies of visual pigments. J Am Chem Soc. 1981;103(24):7195-201.

Lovey et al., Fluorinated retinoic acids and their analogs. 3. Synthesis and biological activity of aromatic 6-fluoro analogs. J Med Chem. 1982;25(1):71-75.

Maas et al., Dication disulfides by reaction of thioureas and related compounds with trifluoromethanesulfonic anhydride. The role of triflic anhydride as an oxidizing agent. J Org Chem. 1981;46(8):1606-1610.

Maas et al., Dication ethers. 7. Dication ether salts from cyclic bisureas. J Heterocyclic Chemistry. 1985;22(3):907-10.

Mack et al., Effect of Chelate Ring Expansion on Jahn-Teller Distortion and Jahn-Teller Dynamics in Copper(II) Complexes. Inorg Chem. 2012;51(14):7851-7858.

Maeda et al., Amino Acids and Peptides. X. : Leu-Enkephalin Analogues Containing a Fluorinated Aromatic Amino Acid. Chem Pharm Bull. 1989;37(3):826-28.

Maimone et al., Evidence for in situ catalyst modification during the Pd-catalyzed conversion of aryl triflates to aryl fluorides. J Am Chem Soc. Nov. 16, 2011;133(45):18106-9. doi: 10.1021/ja208461k. Epub Oct. 21, 2011.

Makleit et al., Synthesis and chemical transformation of halogen-containing morphine derivatives. Magyar Kemikusok Lapja. 1997;52(6):282-89.

Marshall et al., Single-Crystal X-ray and Solution 13C NMR Study of Fluoro(p-nitrophenyl)bis(triphenylphosphine)palladium(II). Are There Effects of Through-Conjugation? Organometallics. 1998;17(24):5427-30.

Matthews et al., Equilibrium acidities of carbon acids. VI. Establishment of an absolute scale of acidities in dimethyl sulfoxide solution. J Am Chem Soc. 1975;97(24):7006-7014.

Mazzotti et al., Palladium(III)-Catalyzed Fluorination of Arylboronic Acid Derivatives. J Am Chem Soc. Sep. 25, 2013;135(38):14012-5. doi: 10.1021/ja405919z. Epub Sep. 16, 2013.

McCombie et al., The condensation of a-Keto-beta-anilino-alpha-phenylethane and its Homologues with Carbonyl Chloride, Phenylcarbimide, and Phenylthiocarbimide. J Chem Soc. 1913;103:56-63.

McGaraughty et al., Effects of A-317491, a novel and selective P2X3/P2X2/3 receptor antagonist, on neuropathic, inflammatory and chemogenic nociception following intrathecal and intraplantar administration. Br J Pharmacol. Dec. 2003;140(8):1381-8. Epub Nov. 17, 2003.

McMurtrey et al., Pd-catalyzed C—H fluorination with nucleophilic fluoride. Pd-catalyzed C—H fluorination with nucleophilic fluoride. Org Lett. Aug. 17, 2012;14(16):4094-7. doi: 10.1021/ol301739f. Epub Jul. 30, 2012.

Mendoza-Espinosa et al., Synthesis of 4- and 4,5-Functionalized Imidazol-2-ylidenes from a Single 4,5-Unsubstituted Imidazol-2-ylidene. J Am Chem Soc. 2010;132(21):7264-7265.

Miao et al., PET of EGFR Expression with an [18]F-Labeled Affibody Molecule. J Nucl Med. 2012;53:1110-1118 (10.2967/jnumed.111.100842).

Miller et al., Synthesis of 11C, 18F, 15O, and 13N radiolabels for positron emission tomography. Angew Chem Int Ed Engl. 2008;47(47):8998-9033. doi: 10.1002/anie.200800222.

Mirica et al., Structure and electronic properties of Pd(III) complexes. Coord Chem Rev. 2013;257(2):299-314.

Muller et al., Fluorine in pharmaceuticals: looking beyond intuition. Science. Sep. 28, 2007;317(5846):1881-6.

Muller et al., The rhodium(II)-catalyzed aziridination of olefins with {[(4-nitrophenyl)sulfonyl]imino}phenyl-lambda3-iodane. Canadian J of Chem. 1998;76(6):738-750.

(56) References Cited

OTHER PUBLICATIONS

Murphy et al., Organometallic Fluorides: Compounds Containing Carbonminus signMetalminus signFluorine Fragments of d-Block Metals. Chem Rev. Dec. 18, 1997;97(8):3425-3468.
Nagakura et al., Allodynia and hyperalgesia in adjuvant-induced arthritic rats: time course of progression and efficacy of analgesics. J Pharmacol Exp Ther. Aug. 2003;306(2):490-7. Epub May 1, 2003.
Noel et al., Accelerating palladium-catalyzed C—F bond formation: use of a microflow packed-bed reactor. Angew Chem Int Ed Engl. Sep. 12, 2011;50(38):8900-3. doi: 10.1002/anie.201104652. Epub Aug. 11, 2011.
Nyffeler et al., Selectfluor: Mechanistic Insight and Applications. Angew Chem Int Ed Engl. 2004;44(2):192-212.
Onishi et al., Palladium Polypyrazolylborate Complexes Containing A Pd—C Bond. Chem Lett. 1976:955-58.
Ortiz et al., A Convenient Synthesis of Methyl- and Isopropyl-Benzyl Ethers Using Silver(II) Oxide as Reagent. Synth Commun. 1993;23(6):749-56.
Park et al., Metabolism of fluorine-containing drugs. Annu Rev Pharmacol Toxicol. 2001;41:443-70.
Pawlikowski et al., Alkyl carbon-nitrogen reductive elimination from platinum(IV)-sulfonamide complexes. J Am Chem Soc. Aug. 29, 2007;129(34):10382-93. Epub Aug. 2, 2007.
Pérez et al., Thermal Study of [Pd(2-Phpy)Cl(L)] Complexes (L=pyridines and amines). Journal of Thermal Analysis and Calorimetry. 2001;66(2):361-370.
Phelps, Positron emission tomography provides molecular imaging of biological processes. Proc Natl Acad Sci U S A. Aug. 1, 2000;97(16):9226-33.
Pidlypnyi et al., N-Heterocyclic carbenes from ylides of indolyl-imidazolium, azaindolyl-imidazolium, and indolyl-triazolium salts, and their borane adducts. Tetrahedron. 2014;70(45):8672-80.
Powers et al., Bimetallic palladium catalysis: direct observation of Pd(III)-Pd(III) intermediates. J Am Chem Soc. Dec. 2, 2009;131(47):17050-1. doi: 10.1021/ja906935c.
Powers et al., Bimetallic Pd(III) complexes in palladium-catalysed carbon-heteroatom bond formation. Nat Chem. Jul. 2009;1(4):302-9.
Powers et al., Bimetallic redox synergy in oxidative palladium catalysis. Acc Chem Res. Jun. 19, 2012;45(6):840-50. doi: 10.1021/ar2001974. Epub Oct. 7, 2011.
Powers et al., Bimetallic reductive elimination from dinuclear Pd(III) complexes. J Am Chem Soc. Oct. 13, 2010;132(40):14092-103. doi: 10.1021/ja1036644.
Powers et al., Connecting binuclear Pd(III) and mononuclear Pd(IV) chemistry by Pd—Pd bond cleavage. J Am Chem Soc. Jul. 25, 2012;134(29):12002-9. doi: 10.1021/ja304401u. Epub Jul. 17, 2012.
Powers et al., On the mechanism of palladium-catalyzed aromatic C—H oxidation. J Am Chem Soc. Oct. 20, 2010;132(41):14530-6. doi: 10.1021/ja1054274.
Powers et al., Palladium(III) in Synthesis and Catalysis. Top Organomet Chem. Jan. 1, 2011;503:129-156.
Privalov et al., Theoretical Studies of the Mechanism of Aerobic Alcohol Oxidation with Palladium Catalyst Systems. Organometallics. 2005;24(5):885-893.
Purser et al., Fluorine in medicinal chemistry. Chem Soc Rev. Feb. 2008;37(2):320-30. doi: 10.1039/b610213c. Epub Dec. 13, 2007.
Reed et al., Intermolecular interactions from a natural bond orbital, donor-acceptor viewpoint. Chem Rev. 1988;88(6):899-926.
Roe et al., Structure and Solution Dynamics of [(Ph3P)2Pd(Ph)(FHF)]. Organometallics. 2000;19(22):4575-82.
Ryabov et al., Synthesis by ligand exchange, structural characterization, and aqueous chemistry of ortho-palladated oximes. Inorg Chem. 1992;31(14):3083-3090.
Sandford, Elemental fluorine in organic chemistry (1997-2006). J Fluorine Chem. 2007;128:90-104.
Sarwar, Thermodynamic studies of halogen bonding in solution and application to anion recognition. Doctoral Thesis. University of Toronto. 2012. pp. 1-234. Retrieved on Jun. 17, 2015.
Sasaki et al., Solid phase synthesis and opioid receptor binding activities of [D-Ala2, D-Leu5]enkephalin analogs containing a fluorinated aromatic amino acid. Chem Pharm Bull (Tokyo). Nov. 1990;38(11):3162-3.
Serguchev et al., Transannular additions of selectfluor and xenon difluoride: regioselectivity and mechanism. J Phys Org Chem. 2011;24(5):407-13.
Sheldrick, A short history of SHELX. Acta Cryst Sect A. 2008;A64:112-122.
Singh et al., Recent highlights in electrophilic fluorination with 1-chloromethyl-4-fluoro-1,4-diazoniabicyclo[2.2.2]octane bis(tetrafluoroborate). Acc Chem Res. Jan. 2004;37(1):31-44.
Sladojevich et al., Late-stage deoxyfluorination of alcohols with PhenoFluor. J Am Chem Soc. Feb. 20, 2013;135(7):2470-3. doi: 10.1021/ja3125405. Epub Feb. 11, 2013.
Sladojevich et al., Condensed-phase, halogen-bonded CF3I and C2F5I adducts for perfluoroalkylation reactions. Angew Chem Int Ed Engl. Mar. 16, 2015;54(12):3712-6. doi: 10.1002/anie.201410954. Epub Feb. 4, 2015.
Sun et al., Room-temperature nucleophilic aromatic fluorination: experimental and theoretical studies. Angew Chem Int Ed Engl. Apr. 21, 2006;45(17):2720-5.
Tang et al., Deoxyfluorination of phenols. J Am Chem Soc. Aug. 3, 2011;133(30):11482-4. doi: 10.1021/ja2048072. Epub Jul. 12, 2011.
Tang et al., Silver-catalyzed late-stage fluorination. J Am Chem Soc. Sep. 1, 2010;132(34):12150-4. doi: 10.1021/ja105834t.
Tang et al., Silver-mediated fluorination of aryl silanes. Tetrahedron. Jun. 17, 2011;67(24):4449-4454.
Taylor et al., Catalytic asymmetric heterogeneous aziridination of styrene using CuHY: effect of nitrene donor on enantioselectivity. J Chem Soc Perkin Trans 2. 2001:1714-1723.
Teare et al., Synthesis and reactivity of [18F]-N-fluorobenzenesulfonimide. Chem Commun (Camb). Jun. 21, 2007;2007(23):2330-2.
Ting et al., Arylfluoroborates and alkylfluorosilicates as potential PET imaging agents: high-yielding aqueous biomolecular 18F-labeling. J Am Chem Soc. Sep. 28, 2005;127(38):13094-5.
Tius et al., The reaction of XeF2 with trialkylvinylstannanes: Scope and some mechanistic observations. Tetrahedron. 1995;51(14):3997-4010.
Tredwell et al., Electrophilic fluorination of organosilanes. Org Biomol Chem. Jan. 7, 2006;4(1):26-32. Epub Nov. 23, 2005.
Trofimenko, Boron-pyrazole chemistry. II. Poly(1-pyrazolyl)-borates. J Am Chem Soc. 1967;89(13):3170-3177.
Trofimenko, Polypyrazolylborates, a new class of ligands. Acc Chem Res. 1971;4(1):17-22.
Trofimenko, Recent advances in poly(pyrazolyl)borate (scorpionate) chemistry. Chem Rev. 1993;93(3):943-980.
Vasdev et al., On the preparation of fluorine-18 labelled XeF(2) and chemical exchange between fluoride ion and XeF(2). J Am Chem Soc. Oct. 30, 2002;124(43):12863-8.
Vicente et al., Synthesis of Tris- and Tetrakis(pyrazol-1-yl)borate Gold(III) Complexes. Crystal Structures of [Au{κ2-N,N'-BH(Pz)3}Cl2] (pz=Pyrazol-1-yl) and [Au{κ2-N,N'-B(Pz)4}(κ2-C,N-C6H4CH2NMe2-2)]ClO4·CHCl3. Inorg Chem. 2002;41(7):1870-1875.
Wang et al., Versatile Pd(OTf)2 x 2 H2O-catalyzed ortho-fluorination using NMP as a promoter. J Am Chem Soc. Jun. 10, 2009;131(22):7520-1. doi: 10.1021/ja901352k.
Watson et al., Formation of ArF from LPdAr(F): catalytic conversion of aryl triflates to aryl fluorides. Science. Sep. 25, 2009;325(5948):1661-4. doi: 10.1126/science.1178239. Epub Aug. 13, 2009.
Williams et al., Main group metal halide complexes with sterically hindered thioureas. VIII. Complexes of lead(II) halides with 1,3-dimethyl-2(3H)-imidazolethione. Inorganica Chimica Acta. 1988;144(2):237-40.
Woo et al., Direct conversion of pyranose anomeric OH→F→R in the artemisinin family of antimalarial trioxanes. Tetrahedron Lett. 1998;39(12):1533-36.
Yahav et al., Synthesis of the Elusive (R3P)2MF2 (M=Pd, Pt) Complexes. J Am Chem Soc. 2003;125(45):13634-35.

(56) References Cited

OTHER PUBLICATIONS

Yahav-Levi et al., Competitive aryl-iodide vs aryl-aryl reductive elimination reactions in Pt(IV) complexes: experimental and theoretical studies. J Am Chem Soc. Jan. 16, 2008;130(2):724-31.
Yamada et al., Synthesis And Reaction Of New Type I—N Ylide, N-Tosyliminoiodinane. Chem Lett. 1975;4(4):361-62.
Yandulov et al., Aryl-fluoride reductive elimination from Pd(II): feasibility assessment from theory and experiment. J Am Chem Soc. Feb. 7, 2007;129(5):1342-58.
Ye et al., Mild copper-mediated fluorination of aryl stannanes and aryl trifluoroborates. J Am Chem Soc. Mar. 27, 2013;135(12):4648-51. doi: 10.1021/ja400300g. Epub Mar. 13, 2013.
Zhang et al., Interception of the radicals produced in electrophilic fluorination with radical traps (Tempo, Dmpo) studied by electrospray ionization mass spectrometry. Rapid Commun Mass Spectrom. 2006;20(12):1877-82.
Zhang et al., Investigation of radical cation in electrophilic fluorination by ESI-MS. Org Lett. Sep. 1, 2005;7(18):3877-80.
Neumann et al., Concerted nucleophilic aromatic substitution with (19)F(−) and (18)F(−). Nature. Jun. 16, 2016;534(7607):369-73. doi: 10.1038/nature17667. Epub May 18, 2016.
U.S. Appl. No. 14/431,371, filed Mar. 26, 2015, Ritter et al.
U.S. Appl. No. 15/057,400, filed Mar. 1, 2016, Ritter et al.
U.S. Appl. No. 12/996,274, filed May 10, 2011, Furuya et al.
U.S. Appl. No. 12/865,703, filed Feb. 2, 2009, Ritter et al.
U.S. Appl. No. 13/953,449, filed Jul. 29, 2013, Ritter et al.
U.S. Appl. No. 13/383,055, filed Aug. 23, 2012, Ritter.
U.S. Appl. No. 13/143,705, filed Dec. 27, 2011, Ritter et al.
U.S. Appl. No. 13/130,033, filed Aug. 3, 2011, Ritter et al.
U.S. Appl. No. 13/817,874, filed Oct. 3, 2013, Lee et al.
U.S. Appl. No. 13/444,676, filed Apr. 11, 2012, Ritter et al.
U.S. Appl. No. 13/143,694, filed Feb. 27, 2012, Ritter et al.
U.S. Appl. No. 13/880,606, filed Oct. 20, 2011, Ritter et al.
PCT/US2014/061066, Jan. 12, 2015, Invitation to Pay Additional Fees.
PCT/US2014/061066, May 8, 2015, International Search Report and Written Opinion.
PCT/US2014/061066, Apr. 28, 2016, International Preliminary Report on Patentability.
PCT/US2013/061968, Jan. 3, 2014, Invitation to Pay Additional Fees.
PCT/US2013/061968, Mar. 7, 2014, International Search Report and Written Opinion.
PCT/US2013/061968, Apr. 9, 2015, International Preliminary Report on Patentability.
EP 09759505.2, Jan. 20, 2012, Extended European Search Report.
PCT/US2009/046401, Sep. 22, 2009, International Search Report and Written Opinion.
PCT/US2009/046401, Dec. 16, 2010, International Preliminary Report on Patentability.
PCT/US2009/032855, Jun. 8, 2009, International Search Report and Written Opinion.
PCT/US2009/032855, Aug. 12, 2010, International Preliminary Report on Patentability.
PCT/US2010/041561, Sep. 28, 2010, Invitation to Pay Additional Fees.
PCT/US2010/041561, Jun. 15, 2011, International Search Report and Written Opinion.
PCT/US2010/041561, Jan. 19, 2012, International Preliminary Report on Patentability.
EP 10729595.8, May 22, 2013, Extended European Search Report.
PCT/US2010/020544, Oct. 7, 2010, International Search Report and Written Opinion.
PCT/US2010/020544, Jul. 21, 2011, International Preliminary Report on Patentability.
EP 09828291.6, May 18, 2012, Extended European Search Report.
PCT/US2009/065339, Jul. 12, 2010, International Search Report and Written Opinion.
PCT/US2009/065339, Jun. 3, 2011, International Preliminary Report on Patentability.
PCT/US2011/048451, Mar. 22, 2012, International Search Report and Written Opinion.
PCT/US2011/048451, Mar. 7, 2013, International Preliminary Report on Patentability.
EP 11818838.2, Dec. 10, 2013, Extended European Search Report.
PCT/US2012/033125, Nov. 9, 2012, International Search Report and Written Opinion.
PCT/US2012/033125, Oct. 24, 2013, International Preliminary Report on Patentability.
EP 12771755.1, Aug. 5, 2014, Extended European Search Report.
EP 10729593.3, May 3, 2012, Extended European Search Report.
PCT/US2010/020540, Oct. 6, 2010, International Search Report and Written Opinion.
PCT/US2010/020540, Jul. 21, 2011, International Preliminary Report on Patentability.
PCT/US2011/057176, May 3, 2012, International Search Report and Written Opinion.
PCT/US2011/057176, May 2, 2013, International Preliminary Report on Patentability.
PCT/US2015/028446, Jul. 27, 2015, International Search Report and Written Opinion.
PCT/US2015/028446, Nov. 10, 2016, International Preliminary Report on Patentability.

\* cited by examiner

| Radiofluorination method | Convenient SM | Substrate scope | Practicality | NCA | Aliphatic |
|---|---|---|---|---|---|
| Fluorination with $^{18}$F-F$_2$ | ✓ | | | | |
| Diaryliodonium salt fluorination | | | ✓ | ✓ | |
| [$^{18}$F]-F-TEDA fluorination | ✓ | ✓ | | | |
| Palladium-mediated fluorination | | ✓ | | ✓ | |
| Nickel-mediated fluorination | ✓ | ✓ | ✓ | ✓ | |
| Nucleophilic substitution | ✓ | | | ✓ | ✓ |
| Fluorination with Formula (I) | ✓ | | ✓ | ✓ | ✓ |

Figure 3

| Reg | (mm) Start | (mm) Stop | (mm) Centroid | RF | Region Counts | Region CPM | % of Total | % of ROI |
|---|---|---|---|---|---|---|---|---|
| Rgn 1 | 57.1 | 65.7 | 61.2 | 0.021 | 5303.0 | 5303.0 | 25.79 | 29.38 |
| Rgn 2 | 76.1 | 86.4 | 80.7 | 0.345 | 12744.0 | 12744.0 | 61.98 | 70.62 |
| 2 Peaks | | | | | 18047.0 | 18047.0 | 87.77 | 100.00 |

FLUORINATION OF ORGANIC COMPOUNDS

RELATED APPLICATIONS

This application is a national stage filing under 35 U.S.C. § 371 of international PCT application, PCT/US2014/061066, filed Oct. 17, 2014, which claims priority under 35 U.S.C. § 119(e) to U.S. Provisional Patent Applications, U.S. Ser. No. 61/892,935 filed Oct. 18, 2013, U.S. Ser. No. 61/895,254 filed Oct. 24, 2013, and U.S. Ser. No. 62/037,418 filed Aug. 14, 2014, each of which is incorporated herein by reference.

GOVERNMENT SUPPORT

This invention was made with Government support under grants GM088237 and EB013042 awarded by National Institutes of Health. The Government has certain rights in the invention.

FIELD OF THE INVENTION

The invention relates to compounds, compositions, kits, systems, and methods of fluorinating an organic compound using a fluorinating agent.

BACKGROUND OF INVENTION

Functionalized aryl fluorides are used as pharmaceuticals and agrochemicals, in part due to their favorable pharmacological properties such as increased metabolic stability (see, for example, Müller et al., *Science* 2007, 317, 1881-1886; Kirk et al., *Org. Process Res. Dev.* 2001, 41, 443-470; and Jeschke, P. *ChemBioChem* 2004, 5, 570-589). Aryl fluorides also find applications as tracers in positron emission tomography using the [$^{18}$F]isotope (Lasne et al., In *Contrast Agents II*, 2002; Vol. 222, pp 201-258). Fluorine has the highest electronegativity, the highest oxidation potential, and the smallest anionic radius of all elements, each of which complicates carbon-fluorine bond formation when compared to other carbon-heteroatom bond formations (see, for example, Chambers, R. D., *Fluorine in organic chemistry*. Oxford: New York, 2004; and Furuya et al., *Curr. Opin. Drug Discov. Devel.* 2008, 11, 803-819).

SUMMARY OF INVENTION

The invention relates to compounds, compositions, kits, systems, and methods of fluorinating an organic compound using a fluorinating agent. Besides the vast number of applications of fluorinated organic molecules bearing the natural $^{19}$F isotope, compounds bearing the radioisotope $^{18}$F are invaluable as ligands for Positron Emission Tomography (PET). PET is a non-invasive imaging technique used to observe and probe biological processes in vivo. The non-natural isotope $^{18}$F, which is manufactured within 100 miles of ~98% of the hospital beds in the US, is the radionucleus of choice for many imaging applications due to its favorable half-life of 109 min and its low positron emission energy. The unnatural isotope $^{18}$F is generated using a cyclotron, either as nucleophilic $^{18}$F-fluoride or as electrophilic $^{18}$F-fluorine gas ($^{18}$F—$_2$). $^{18}$F-fluoride is the preferred source of $^{18}$F due to its high isotopic enrichment, wide availability and ease of use. The low reactivity of $^{18}$F$^-$ towards arenes renders radiofluorination challenging particularly for complex substrates that require mild reaction conditions. Due to the 109 min half-life of $^{18}$F the introduction of the radionuclide needs to occur late-stage in the synthesis of the desired radiotracer to avoid unproductive decay. Currently, positron emission tomography (PET) with $^{18}$F is most recognized as a clinical tool for the diagnosis and staging of cancer.

While simple molecules such as 2-deoxy-2-($^{18}$F)fluoro-D-glucose ([$^{18}$F]FDG) can be efficiently prepared, structurally more complex molecules often cannot. The potential biomedical applications of PET for studying a variety of diseases such as cancer, cardiovascular disease, autoimmunity, neurodegeneration, and psychiatric illness are impeded by the lack of suitable $^{18}$F-based PET tracers. To find a PET tracer with the desired in vivo properties, a wide range of candidates commonly have to be radiolabelled and tested. Due to the lack of robust late-stage radiofluorination reactions currently available, tracer synthesis often requires evaluation of several labeling methods and multistep syntheses. Consequently, a general method that can tolerate a multitude of structural elements would severely curtail the development time required for new PET tracers.

Broad access to a variety of $^{18}$F-labeled molecules could transform molecular imaging aimed at determining pathophysiology of diseases in pre-clinical and clinical research and, ultimately, impact patient care through improved diagnostic and prognostic criteria. Moreover, drug development can be streamlined by employing radiolabeled probe molecules in phase 0 clinical trials, which reveal drug distribution and real-time pharmacokinetics throughout all tissues of the body.

Nucleophilic substitution chemistry is widely used in PET probe synthesis due to its predictability, operational convenience, and applicability to aliphatic and aromatic substrates. Electron-rich and many electron-neutral aromatic substrates, however, do not undergo displacement, and side reactions plague nucleophilic substitutions at many hindered or secondary aliphatic centers.

Incorporation into diaryl iodonium salts render aromatic rings activated towards nucleophilic attack even if no additional electron-withdrawing groups are present. A drawback of this approach is the difficulty associated with the synthesis and purification of diaryliodonium salts; many (particularly acid-sensitive) functional groups are not tolerated under the synthesis conditions currently available.

An ideal radiofluorination method would meet all of the following criteria: non-carrier-added reactions, commercially available, bench stable reagents, readily accessible starting materials, operationally simple radiolabeling and purification procedures, general applicability to aliphatic and aromatic substrates. Currently available radiofluorination methods fall short of at least one of these goals (see FIG. 3).

The inventors have previously described a reagent for fluorination (see FIG. 2). The reagent, known as PhenoFluor®, exhibits exceptional substrate scope and functional group tolerance. The new reagents of Formula (I) provide access to late-stage fluorination similar to PhenoFluor®, but without the need for additional fluoride, so that no-carrier-added (nca) reactions become feasible.

The new fluorinating reagent is capable of site-specific substitution of hydroxyl groups with non-carrier-added $^{18}$F-fluoride in a one-step transformation. The transformation is metal-free and combines the substrate scope of late-stage fluorination with the convenient and broadly implemented reaction setup of simple displacement chemistry. The use of readily available phenols or alcohols as labeling precursors allows rapid access to new PET probes. Development of this method of radiofluorination into a fully automated, versatile $^{18}$F-labeling protocol would considerably streamline tracer development through the synthesis of desirable PET probes.

The fluorination reagent of Formula (I) stems from development of a radiofluorination reaction that can convert convenient starting materials to fluorides using non-carrier-added $^{18}$F-fluoride in a straightforward one-step procedure. Phenols and alcohols can readily be synthesized and purified, and the fluorination method can tolerate a wide range of functional groups, including tertiary amines and protic functional groups.

Substrates such as estrone, which lack electron-withdrawing activating groups, undergo radiofluorination. The ability to introduce $^{18}$F-fluoride into electron-neutral aromatic substrates (see Examples) sets the proposed transformation apart from nucleophilic aromatic substitution chemistry. Secondary aliphatic alcohols such as cholesterol, menthol, testosterone, and epiandrosterone yield the corresponding radiolabeled derivatives, in most cases with complete stereocontrol (inversion) as was established by the inventors through deoxyfluorination with PhenoFluor®. A yield of 25% for the radiofluorination of menthol is particularly noteworthy (see Experimental section) because menthol contains a hindered, branched substituent in the β-position to the hydroxyl group, which renders the reaction site sterically crowded; conventional nucleophilic displacement reactions typically afford significant amounts of byproducts such as those derived from elimination as observed for displacement reactions at hindered secondary carbon atoms. Unprotected primary anilines such can be tolerated in fluorination with reagents of Formula (I).

Purification of the radiolabeled material by HPLC is facile because both phenol and alcohol starting material have a significantly different polarity from the fluorinated product. In addition, radiofluorination with reagents of Formula (I) is a metal-free transformation, which further simplifies purification because reaction mixtures can be directly concentrated and purified by preparative HPLC. The inventors have found that radiolabeling with reagents of Formula (I) is a very clean reaction, with only minimal side product formation: The HPLC UV-trace shows only the starting phenol and urea (urea=deprotonated I-c).

One embodiment of the present invention provides compounds of Formula (I):

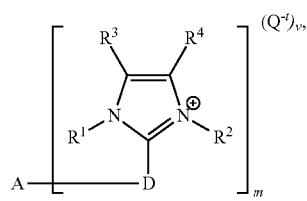

(I)

wherein:
  D is oxygen or sulfur;
  A is hydrogen or a Lewis acid;
  Q is an anion;
  $R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —NH$_2$, —NHR$^7$, —N(R$^7$)$_2$, —OH, —SH, —SO$_2$R$^7$, —SOR$^7$, —SO$_2$NR$^7$$_2$, and —SR$^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two R$^7$ groups are taken together with their intervening atoms to form an optionally substituted heterocyclic ring;

$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH$_2$, —NHR$^7$, —N(R$^7$)$_2$, —OH, —SH, —SO$_2$R$^7$, —SOR$^7$, —SO$_2$NR$^7$$_2$, and —SR$^7$;

t is the anion charge number, ranging from 1-3;
  v is 0-3; and
  m is 1-5.

Exemplary compounds of Formula (I) include compounds of Formula (I-c) and Formula (I-d):

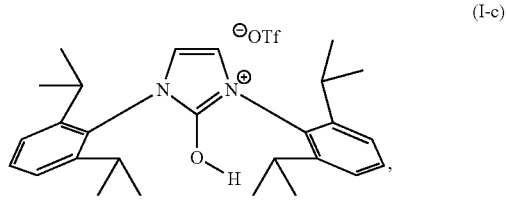

(I-c)

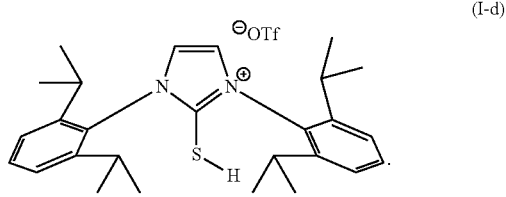

(I-d)

In another aspect, the present invention provides compounds represented by Formula (II):

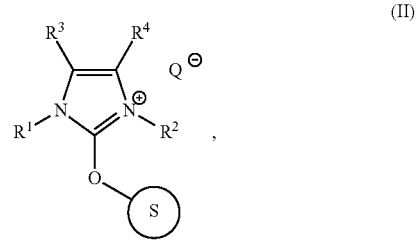

(II)

wherein S is an organic substrate.

In certain embodiments, the compound of Formula (II) is a compound of Formula (II-c)-(II-h):

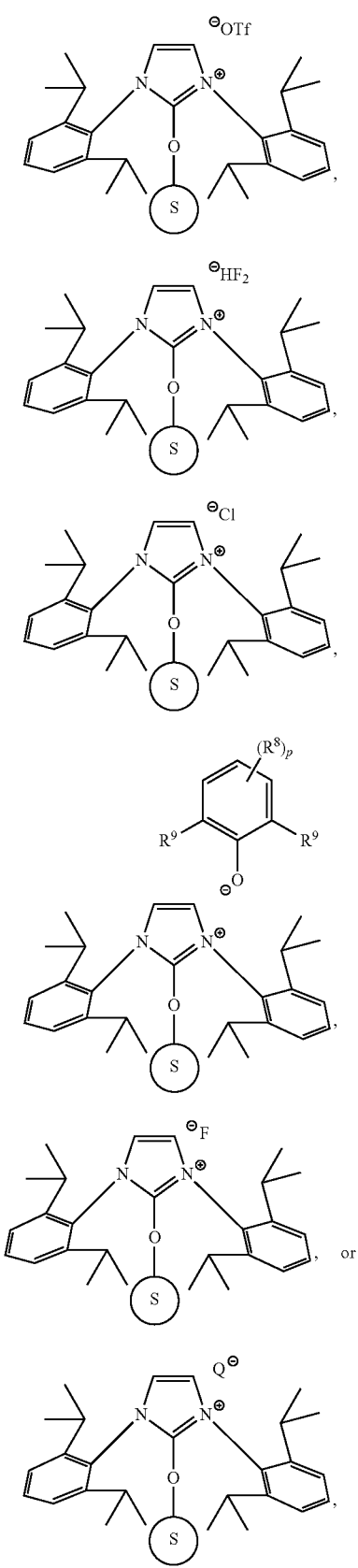

wherein each occurrence of $R^8$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$N(R^{8a})_2$, —$OR^{8a}$, —$CO_2R^{8a}$, —$SO_2R^{8a}$, —$SOR^{8a}$, —$SO_2N(R^{8a})_2$, and —$SR^{8a}$;

each occurrence of $R^9$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, and optionally substituted 4-10 membered heterocyclylalkyl, acyl, —$N(R^{9a})_2$, —$OR^{9a}$, —$CO_2R^{9a}$, —$SO_2R^{9a}$, —$SOR^{9a}$, —$SO_2N(R^{9a})_2$, and —$SR^{9a}$;

each occurrence of $R^{8a}$ or $R^{9a}$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^{8a}$ or $R^{9a}$ groups are taken together with their intervening atoms to form an optionally substituted heterocyclic ring; and p is 0, 1, 2, or 3.

In another aspect, the present invention provides compounds represented by Formula (V):

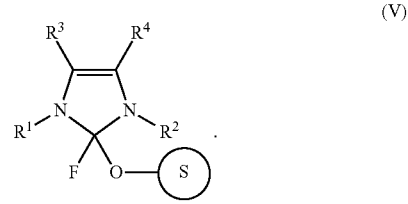

In certain embodiments, the fluorine is enriched in the $^{18}F$ isotope.

In certain embodiments, the compound of Formula (V) is a compound of Formula (V-c):

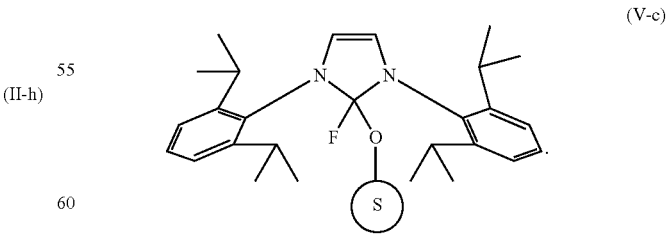

In certain embodiments, the fluorine is enriched in the $^{18}F$ isotope.

In another aspect, the present invention provides compounds represented by Formula (VI):

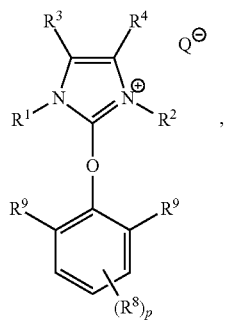

(VI)

wherein each occurrence of $R^8$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —N($R^{8a}$)$_2$, —O$R^{8a}$, —CO$_2R^{8a}$, —SO$_2R^{8a}$, —SO$R^{8a}$, —SO$_2$N($R^{8a}$)$_2$, and —S$R^{8a}$;

each occurrence of $R^9$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, and optionally substituted 4-10 membered heterocyclylalkyl, acyl, —N($R^{9a}$)$_2$, —O$R^{9a}$, —CO$_2R^{9a}$, —SO$_2R^{9a}$, —SO$R^{9a}$, —SO$_2$N($R^{9a}$)$_2$, and —S$R^{9a}$;

each occurrence of $R^{8a}$ or $R^{9a}$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^{8a}$ or $R^{9a}$ groups are taken together with their intervening atoms to form an optionally substituted heterocyclic ring; and p is 0, 1, 2, or 3.

In certain embodiments, the compound of Formula (VI) is a compound of Formula (VI-c)-(VI-f):

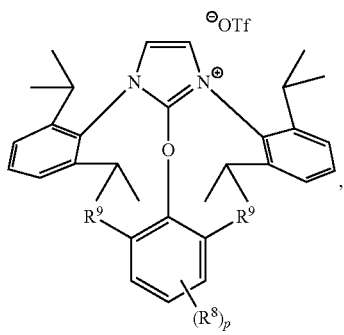

(VI-c)

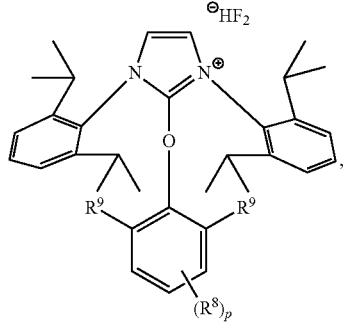

(VI-d)

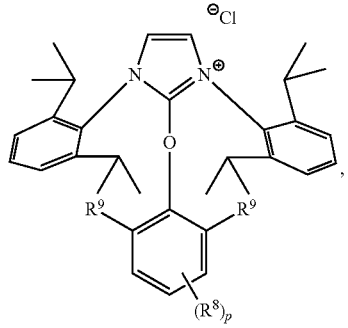

(VI-e)

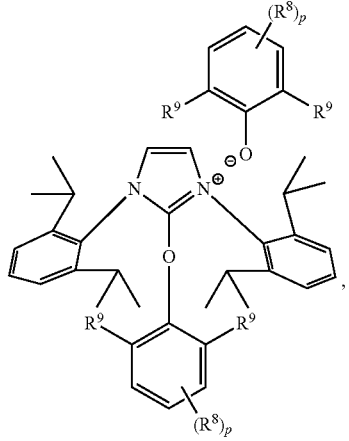

(VI-f)

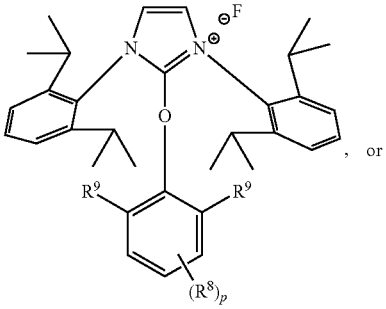

(VI-g)

, or

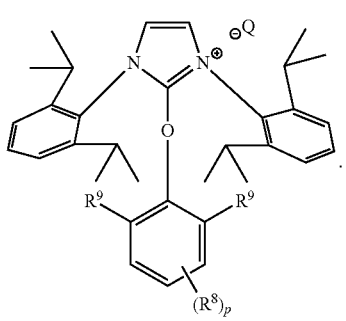

(VI-h)

In another aspect, the present invention provides methods of replacing a hydroxyl group on an organic compound with a fluorine atom, the method comprising contacting a compound of Formula (I):

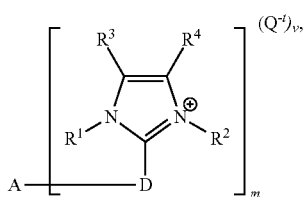

(I)

with an organic compound under conditions sufficient to fluorinate the organic compound, thereby providing a fluorinated organic compound.

In certain embodiments, the method comprises contacting a compound of Formula (I-c):

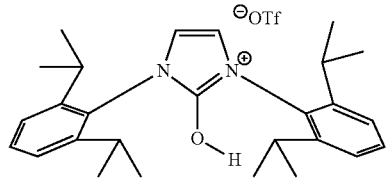

(I-c)

with an organic compound under conditions sufficient to fluorinate the organic compound, thereby providing a fluorinated organic compound.

In another aspect, the present invention provides methods of replacing a hydroxyl group of an organic compound with a fluorine atom, the method comprising exchanging an anion Q of a compound of Formula (II):

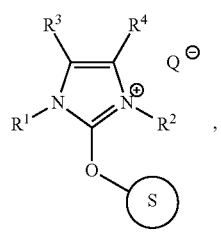

(II)

with a fluoride or $HF_2$ anion. In certain embodiments, the ion exchange reaction is carried out using an anion exchange resin or anion exchange chromatography. In certain embodiments, the fluorine source is enriched in the $^{18}F$ isotope. In certain embodiments, the anion exchange reaction is carried out in aqueous dioxane. In certain embodiments, the resulting intermediate is heated to approximately 110° C. following anion exchange. In certain embodiments, the intermediate is heated for approximately 5 minutes.

In certain embodiments, the method comprises exchanging the chloride anion of a compound of Formula (II-e):

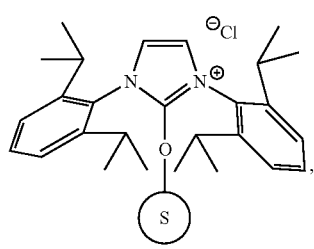

(II-e)

with a fluoride or $HF_2$ anion. In certain embodiments, the ion exchange reaction is carried out using an anion exchange resin or anion exchange chromatography. In certain embodiments, the fluorine source is enriched in the $^{18}F$ isotope. In certain embodiments, the anion exchange reaction is carried out in aqueous dioxane. In certain embodiments, the resulting intermediate is heated to approximately 110° C. following anion exchange. In certain embodiments, the intermediate is heated for approximately 5 minutes.

In certain embodiments, the method comprises exchanging the phenolate anion of a compound of Formula (II-f):

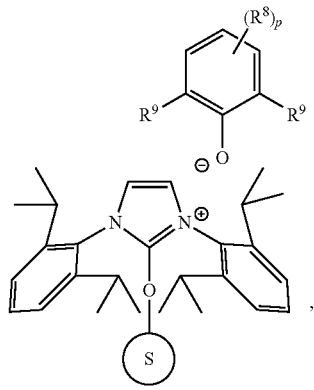

(II-f)

with a fluoride or $HF_2$ anion. In certain embodiments, the ion exchange reaction is carried out using an anion exchange resin or anion exchange chromatography. In certain embodiments, the fluorine source is enriched in the $^{18}F$ isotope. In certain embodiments, the anion exchange reaction is carried out in aqueous dioxane. In certain embodiments, the resulting intermediate is heated to approximately 110° C. following anion exchange. In certain embodiments, the intermediate is heated for approximately 5 minutes.

In another aspect, the present invention is directed to a method of producing a compound of Formula (II):

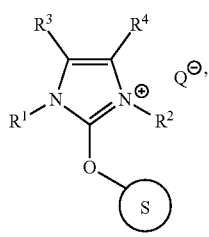

the method comprising contacting a compound of Formula (VI):

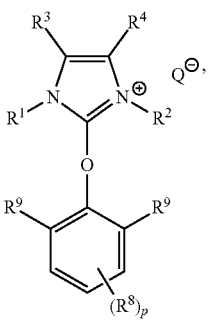

with a hydroxyl group-containing organic substrate and exchanging

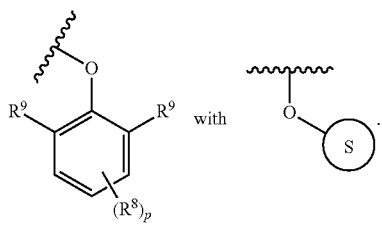

In another aspect, the present invention is directed to a method of producing a compound of Formula (I), the method comprising contacting a compound of Formula (I-e):

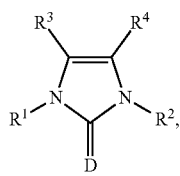

with a Brønsted acid, a Lewis acid, or an acid anhydride to produce the compound of Formula (I).

In another aspect, the present invention provides kits comprising a container with a compound described herein. The provided kits may be useful in a method of the invention. In certain embodiments, the kit further includes instructions for using the kit.

BRIEF DESCRIPTION OF THE DRAWINGS

FIG. 3 shows the comparison of several radiofluorination methods where a tick marks a positive feature of the respective technique (SM=starting material=labeling precursor, NCA=non-carrier-added, Aliphatic=applicability to aliphatic substrates).

FIG. 6 shows Radio TLC scans for isotopic labeling experiments.

FIG. 7 shows fluorination reactions carried out through treatment of uronium intermediates with exogenous fluorine sources.

DEFINITIONS

Figure 1:
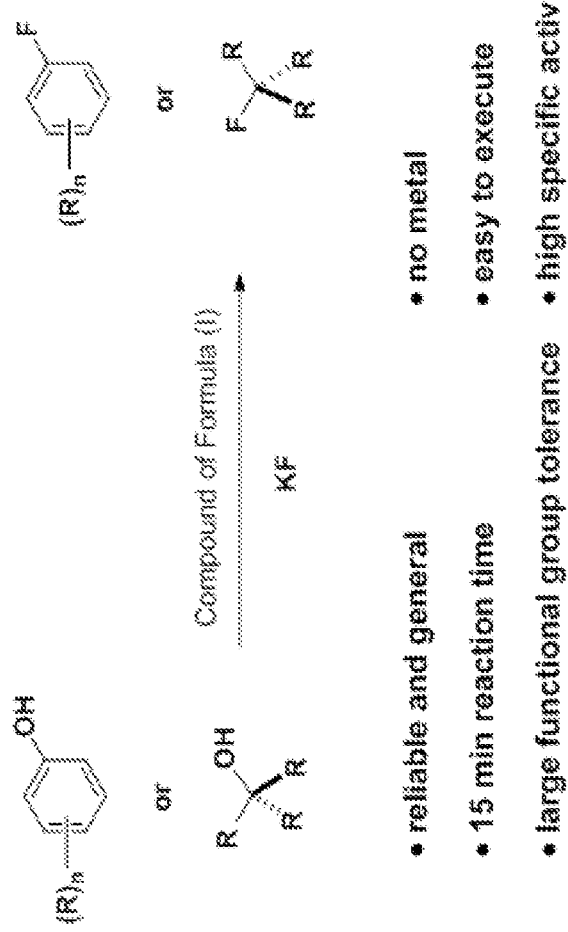
FIG. 1 shows the general fluorination reactions accomplished through use of reagents of Formula (I).

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

It is to be understood that the compounds of the present invention may be depicted as different tautomers. It should also be understood that when compounds have tautomeric forms, all tautomeric forms are intended to be included in the scope of the present invention, and the naming of any compound described herein does not exclude any tautomer form.

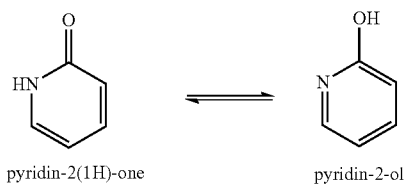 [SMILES: O=c1cccc[nH]1 ; Oc1ccccn1]

pyridin-2(1H)-one      pyridin-2-ol

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

The term "aliphatic," as used herein, includes both saturated and unsaturated, nonaromatic, straight chain (i.e., unbranched), branched, acyclic, and cyclic (i.e., carbocyclic) hydrocarbons. In certain embodiments, an aliphatic group is optionally substituted with one or more functional groups. As will be appreciated by one of ordinary skill in the art, "aliphatic" is intended herein to include alkyl, alkenyl, alkynyl, cycloalkyl, and cycloalkenyl moieties.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In certain embodiments, an alkyl group has 1 to 10 carbon atoms ("$C_{1-10}$ alkyl"). In certain embodiments, an alkyl group has 1 to 9 carbon atoms ("$C_{1-9}$ alkyl"). In certain embodiments, an alkyl group has 1 to 8 carbon atoms ("$C_{1-8}$ alkyl"). In certain embodiments, an alkyl group has 1 to 7 carbon atoms ("$C_{1-7}$ alkyl"). In certain embodiments, an alkyl group has 1 to 6 carbon atoms ("$C_{1-6}$ alkyl"). In certain embodiments, an alkyl group has 1 to 5 carbon atoms ("$C_{1-5}$ alkyl"). In certain embodiments, an alkyl group has 1 to 4 carbon atoms ("$C_{1-4}$ alkyl"). In certain embodiments, an alkyl group has 1 to 3 carbon atoms ("$C_{1-3}$ alkyl"). In certain embodiments, an alkyl group has 1 to 2 carbon atoms ("$C_{1-2}$ alkyl"). In certain embodiments, an alkyl group has 1 carbon atom ("$C_1$ alkyl"). In certain embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

In certain embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In certain embodiments, the alkyl moiety has 1 to 8 carbon atoms ("$C_{1-8}$ perhaloalkyl"). In certain embodiments, the alkyl moiety has 1 to 6 carbon atoms ("$C_{1-6}$ perhaloalkyl"). In certain embodiments, the alkyl moiety has 1 to 4 carbon atoms ("$C_{1-4}$ perhaloalkyl"). In certain embodiments, the alkyl moiety has 1 to 3 carbon atoms ("$C_{1-3}$ perhaloalkyl"). In certain embodiments, the alkyl moiety has 1 to 2 carbon atoms ("$C_{1-2}$ perhaloalkyl"). In certain embodiments, all of the hydrogen atoms are replaced with fluoro. In certain embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In certain embodiments, an alkenyl group has 2 to 10 carbon atoms ("$C_{2-10}$ alkenyl"). In certain embodiments, an alkenyl group has 2 to 9 carbon atoms ("$C_{2-9}$ alkenyl"). In certain embodiments, an alkenyl group has 2 to 8 carbon atoms ("$C_{2-8}$ alkenyl"). In certain embodiments, an alkenyl group has 2 to 7 carbon atoms ("$C_{2-7}$ alkenyl"). In certain embodiments, an alkenyl group has 2 to 6 carbon atoms ("$C_{2-6}$ alkenyl"). In certain embodiments, an alkenyl group has 2 to 5 carbon atoms ("$C_{2-5}$ alkenyl"). In certain embodiments, an alkenyl group has 2 to 4 carbon atoms ("$C_{2-4}$ alkenyl"). In certain embodiments, an alkenyl group has 2 to 3 carbon atoms ("$C_{2-3}$ alkenyl"). In certain embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In certain embodiments, an alkynyl group has 2 to 10 carbon atoms ("$C_{2-10}$ alkynyl"). In certain embodiments, an alkynyl group has 2 to 9 carbon atoms ("$C_{2-9}$ alkynyl"). In certain embodiments, an alkynyl group has 2 to 8 carbon atoms ("$C_{2-8}$ alkynyl"). In certain embodiments, an alkynyl group has 2 to 7 carbon atoms ("$C_{2-7}$ alkynyl"). In certain embodiments, an alkynyl group has 2 to 6 carbon atoms ("$C_{2-6}$ alkynyl"). In certain embodiments, an alkynyl group has 2 to 5 carbon atoms ("$C_{2-5}$ alkynyl"). In certain embodiments, an alkynyl group has 2 to 4 carbon atoms ("$C_{2-4}$ alkynyl"). In certain embodiments, an alkynyl group has 2 to 3 carbon atoms ("$C_{2-3}$ alkynyl"). In certain embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In certain embodiments, a carbocyclyl group has 3 to 8 ring carbon atoms ("$C_{3-8}$ carbocyclyl"). In certain embodiments, a carbocyclyl group has 3 to 6 ring carbon atoms ("$C_{3-6}$ carbocyclyl"). In certain embodiments, a carbocyclyl group has 3 to 6 ring carbon atoms ("$C_{3-6}$ carbocyclyl"). In certain embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or is a fused, bridged or spiro-fused ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In certain embodiments, "carbocyclyl" is a monocyclic, saturated carbocyclyl group having from 3 to 10 ring carbon atoms ("$C_{3-10}$ cycloalkyl"). In certain embodiments, a cycloalkyl group has 3 to 8 ring carbon atoms ("$C_{3-8}$ cycloalkyl"). In certain embodiments, a cycloalkyl group has 3 to 6 ring carbon atoms ("$C_{3-6}$ cycloalkyl"). In certain embodiments, a cycloalkyl group has 5 to 6 ring carbon atoms ("$C_{5-6}$ cycloalkyl"). In certain embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro-fused ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In certain embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In certain embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In certain embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In certain embodiments, the 5-6 membered heterocyclyl has 1-3 ring heteroatoms independently selected from nitrogen, oxygen, and sulfur. In certain embodiments, the 5-6 membered heterocyclyl has 1-2 ring heteroatoms independently selected from nitrogen, oxygen, and sulfur. In certain embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In certain embodiments, an aryl group has six ring carbon atoms ("$C_6$ aryl"; e.g., phenyl). In certain embodiments, an aryl group has ten ring carbon atoms ("$C_{10}$ aryl"; e.g., naphthyl such as 1-naphthyl and 2-naphthyl). In certain embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In certain embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In certain embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In certain embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In certain embodiments, the 5-6 membered heteroaryl has 1-3 ring heteroatoms independently selected from nitrogen, oxygen, and sulfur. In certain embodiments, the 5-6 membered heteroaryl has 1-2 ring heteroatoms independently selected from nitrogen, oxygen, and sulfur. In certain embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Fused" or "ortho-fused" are used interchangeably herein, and refer to two rings that have two atoms and one bond in common, e.g.,

napthalene

"Bridged" refers to a ring system containing (1) a bridgehead atom or group of atoms which connect two or more non-adjacent positions of the same ring; or (2) a bridgehead atom or group of atoms which connect two or more positions of different rings of a ring system and does not thereby form an ortho-fused ring, e.g.,

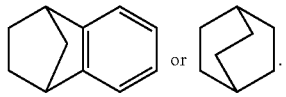

"Spiro" or "Spiro-fused" refers to a group of atoms which connect to the same atom of a carbocyclic or heterocyclic ring system (geminal attachment), thereby forming a ring, e.g.,

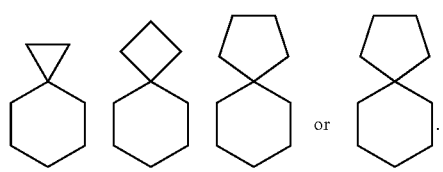

Spiro-fusion at a bridgehead atom is also contemplated.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In certain embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, OC(=NR$^{ff}$)R$^{ee}$, —OC(=NR$^{ff}$)OR$^{ee}$, —C(=NR)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$alkyl)$_2$, —NHC(=O)NH(C$_{1-6}$alkyl), —NHC(=O)NH$_2$, —C(=NH)O(C$_{1-6}$ alkyl), —OC(=NH)(C$_{1-6}$alkyl), —OC(=NH)OC$_{1-6}$alkyl, —C(=NH)N(C$_{1-6}$ alkyl)$_2$, —C(=NH)NH(C$_{1-6}$alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(=O)_2R$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

The term "acyl," used alone or a part of a larger moiety, refers to groups formed by removing a hydroxy group from a carboxylic acid. Exemplary acyl groups include, without limitation, —C(=O)Me, —C(=O)Et, —C(=O)i-Pr, —C(=O)aryl, and —C(=O)CH$_2$F.

The term "Lewis acid" refers to a species as defined by IUPAC, that is "a molecular entity (and the corresponding chemical species) that is an electron-pair acceptor and therefore able to react with a Lewis base to form a Lewis adduct, by sharing the electron pair furnished by the Lewis base." Exemplary Lewis acids include, without limitation, boron trifluoride, aluminum trichloride, tin tetrachloride, titanium tetrachloride, and iron tribromide.

The term "Brønsted acid" refers to a protic or proton-donating species. Exemplary Brønsted acids include, without limitation, acetic acid, triflic acid, hydrochloric acid, and barbituric acid.

The term "acid anhydride" refers to an organic compound that has two acyl, phosphoryl, or sulfonyl groups bound to the same oxygen atom. Most commonly, the acyl groups are derived from the same carboxylic acid. One or both acyl groups of an acid anhydride may also be derived from another type of organic acid, such as sulfonic acid or a phosphonic acid. One of the acyl groups of an acid anhydride can be derived from an inorganic acid such as phosphoric acid. Exemplary acid anhydrides include, without limitation, acetic anhydride, maleic anhydride, and triflic anhydride.

The term "PhenoFluor" refers to the trade name for the fluorinating reagent 1,3-bis(2,6-diisopropylphenyl)-2,2-difluoro-2,3-dihydro-1H-imidazole. The invention is described in international application, PCT/US2012/033125, published as WO 12/142162, which is incorporated herein by reference.

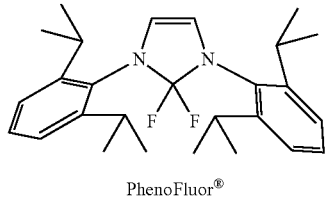 [SMILES: CC(C)c1cccc(C(C)C)c1N1C=CN(c2c(C(C)C)cccc2C(C)C)C1(F)F]

PhenoFluor®

The term "no-carrier-added" or "non-carrier-added" reaction typically refers to a reaction carried out with preparation of a radioactive isotope without deliberate addition of a non-radioactive isotope. However, in the context of the preparation of PET imaging agents labeled with $^{18}$F, using only the radioactive isotope would be ideal but can be practically challenging or even impossible due to the very low quantities of the $^{18}$F-labelled reagent (e.g., K$^{18}$F) relative to the organic reactant. Inefficient reactions will therefore rely on the inclusion of excess "carrier" stable isotope (e.g., $^{19}$F) in order to promote reaction progress, thus producing PET imaging agents of lower radioactivity. Therefore, development of "non-carrier-added" reactions is beneficial for the generation of high-specific activity agents, but sometimes this cannot be achieved based on a given reaction and/or substrate.

The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998)), and include those useful in techniques such as the "split and pool" or "parallel" synthesis techniques, solid-phase and solution-phase techniques, and encoding techniques (see, for example, Czarnik, A. W., *Curr. Opin. Chem. Bio.*, (1997) 1, 60).

The term "stereospecific" refers to the property of a reaction mechanism that leads to different stereoisomeric reaction products from different stereoisomeric reactants, or which operates on only one (or a subset) of the stereoisomers. An example of a stereospecific reaction includes, but is not limited to, a nucleophilic substitution reaction ($S_n^2$) at an sp$^3$ stereocenter, leading to perfect inversion of stereochemistry without erosion of enantiomeric purity.

DETAILED DESCRIPTION OF CERTAIN EMBODIMENTS OF THE INVENTION

As described above, functionalized aryl fluorides find frequent use as pharmaceuticals and agrochemicals, in part due to their favorable pharmacological properties such as increased metabolic stability. Besides the vast number of applications of fluorinated organic molecules bearing the natural $^{19}$F isotope, compounds bearing the radioisotope $^{18}$F are invaluable as ligands for Positron Emission Tomography (PET). The low reactivity of $^{18}$F$^-$ towards arenes renders radiofluorination challenging particularly for complex substrates that require mild reaction conditions. The potential biomedical applications of PET for studying a variety of diseases such as cancer, cardiovascular disease, autoimmunity, neurodegeneration, and psychiatric illness are impeded by the lack of suitable $^{18}$F-based PET tracers. Various synthetic methods used to make PET tracers (e.g., nucleophilic substitution chemistry, incorporation into diaryl iodonium salts) are not broadly applicable.

Figure 2:
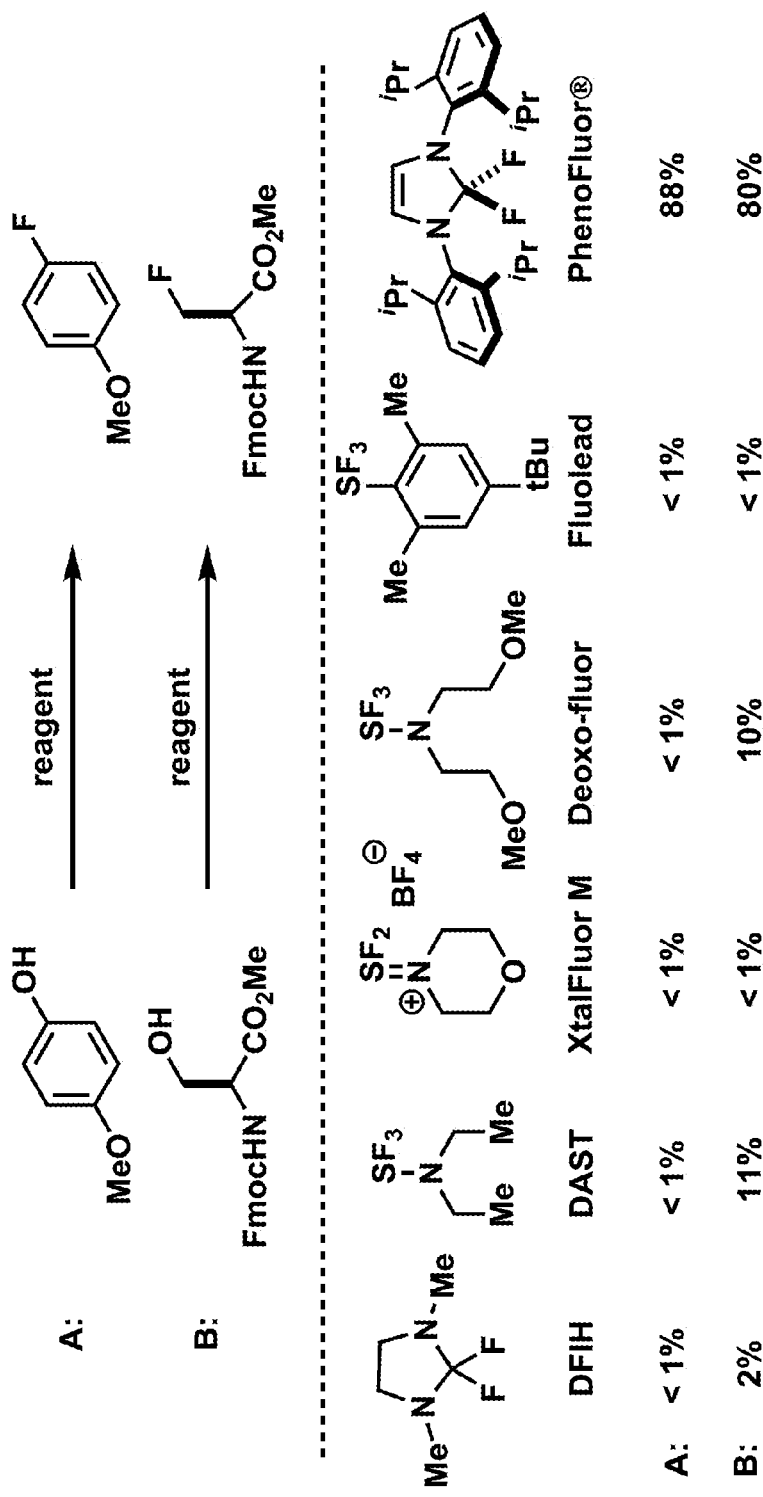
FIG. 2 shows the effective fluorination of both challenging aryl and aliphatic hydroxyl groups using PhenoFluor®, a reagent previously discovered by the inventors. Comparison to other fluorinating agents is highlighted to demonstrate the superiority of PhenoFluor®.

The inventors have previously described a reagent for fluorination (see FIG. 2). The reagent, known as Pheno-Fluor®, exhibits exceptional substrate scope and functional group tolerance. The new reagents of Formula (I) provide access to late-stage fluorination similar to PhenoFluor®, but without the need for additional fluoride, so that no-carrier-added (nca) reactions become feasible.

The new fluorinating reagent is capable of site-specific substitution of hydroxyl groups with non-carrier-added $^{18}$F-fluoride in a one-step transformation. The transformation is metal-free and combines the substrate scope of late-stage fluorination with the convenient and broadly implemented reaction set-up of simple displacement chemistry. The use of readily available phenols or alcohols as labeling precursors allows rapid access to new PET probes. Development of this method of radiofluorination into a fully automated, versatile $^{18}$F-labeling protocol will considerably streamline tracer development through the synthesis of desirable PET probes.

Described herein are methods of fluorinating reagents and methods of making fluorinated organic compounds. Upon making a fluorinating reagent (which may be isolated or used in situ) a reaction of a hydroxyl group-containing organic compound or tautomer thereof and a fluorinating agent is described herein. This subsequent reaction provides a fluorinated organic compound in which the hydroxyl group (or tautomeric carbonyl) of the organic compound is replaced with a fluorine substituent (for example, FIG. 1).

The reaction is not limited to phenyl and aliphatic and may contain a number of other chemical groups. Typical groups include, without limitation, alkyl (e.g., $C_1$, $C_2$, $C_3$, $C_4$, $C_5$, $C_6$, $C_7$, $C_8$, $C_9$, $C_{10}$, $C_{11}$, $C_{12}$ straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkylamino, dialkylamino, $SO_3H$, sulfate, phosphate, methylenedioxy (—O—CH$_2$—O— wherein oxygens are attached to vicinal atoms), ethylenedioxy, oxo, thioxo (e.g., C=S), imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). The substituents are independently any one single, or any subset of the aforementioned substituents. A substituent may itself be substituted with any one of the above substituents. In certain embodiments, two groups may be taken together to form a ring, e.g., an aryl, heteroaryl, cyclyl or heterocyclyl ring, which may itself be further substituted with any one of the above substituents.

In one aspect, the present invention is directed to a compound of Formula (I):

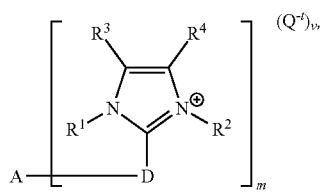

(I)

wherein
D is oxygen or sulfur;
A is hydrogen or a Lewis acid;
Q is an anion;
$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;
$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —NH$_2$, —NHR$^7$, —N(R$^7$)$_2$, —OH, —SH, —SO$_2$R$^7$, —SOR$^7$, —SO$_2$NR$^7$$_2$, and —SR$^7$;
$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring;
$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH$_2$, —NHR$^7$, —N(R$^7$)$_2$, —OH, —SH, —SO$_2$R$^7$, —SOR$^7$, —SO$_2$NR$^7$$_2$, and —SR$^7$;
t is the anion charge number, ranging from 1-3;
v is 0-3; and
m is 1-5.

In certain embodiments, the compound of Formula (I) is a compound of Formula (I-a):

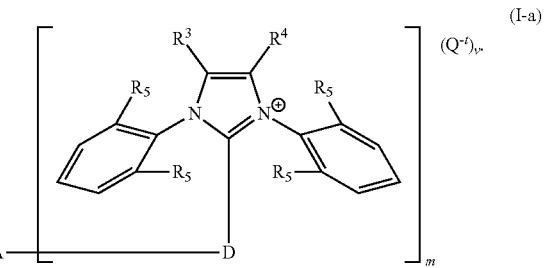

(I-a)

In certain embodiments, the compound of Formula (I) is a compound of Formula (I-b):

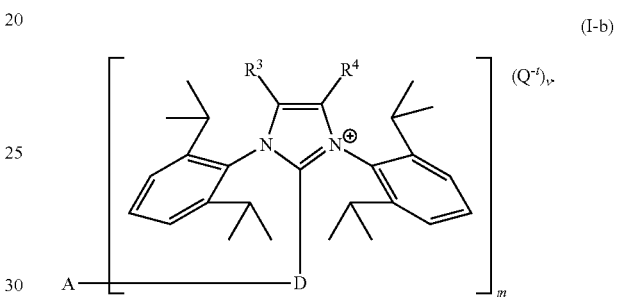

(I-b)

In certain embodiments, D is oxygen. In certain embodiments, D is sulfur.

In certain embodiments, A is hydrogen, m is 1, and v is 1. In certain embodiments, A is hydrogen, m is 1, v is 1, and t is 1. In certain embodiments, A is a Lewis acid, m is 1-4, and v is 0 or 1. In certain embodiments, A is a Lewis acid, m is 1, and v is 0. In certain embodiments, A is a Lewis acid, m is 1, and v is 1. In certain embodiments, A is a Lewis acid, m is 2, and v is 0. In certain embodiments, A is a Lewis acid, m is 2, and v is 1. In certain embodiments, A is a Lewis acid, m is 3, and v is 0. In certain embodiments, A is a Lewis acid, m is 3, and v is 1. In certain embodiments, A is a Lewis acid, m is 4, and v is 0. In certain embodiments, A is a Lewis acid, m is 4, and v is 1.

In certain embodiments, t is 1. In certain embodiments, t is 2. In certain embodiments, t is 3.

In certain embodiments, the compound of Formula (I) is a compound of Formula (I-c):

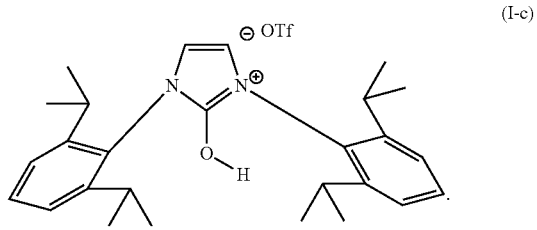 [SMILES: CC(C)c1cccc(C(C)C)c1-n1cc[n+](-c2c(C(C)C)cccc2C(C)C)c1O ; "OTf"]

(I-c)

In certain embodiments, the compound of Formula (I) is a compound of Formula (I-d):

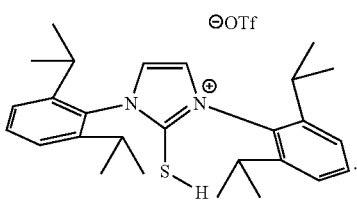 (I-d)

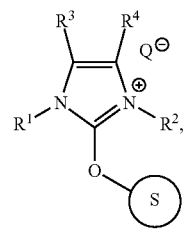 (II)

In certain embodiments, Q of Formula (I) is any suitable counterion. In certain embodiments, Q of Formula (I) is halogen (e.g., fluoro, chloro, bromo, or iodo), trifluoroacetate, trichloroacetate, $NO_2^-$, $NO_3^-$, $H_2PO_4^-$, $PF_6^-$, $HF^{2-}$, $HSO_4^-$, $SbF_6^-$, $ClO_4^-$, $SO_4^{-2}$, $(R^6)SO_3^-$, $OTf^-$, $OTs^-$, $ONf^-$, $ONs^-$, $BF_4^-$, or $B(R^6)_4^-$, wherein $R^6$ is $C_{1-6}$ alkyl, $-OR^7$, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, or 3-10 membered carbocyclylalkyl, each of which is optionally substituted with 0 to 5 occurrences of $R^5$. In certain embodiments, Q of Formula (I) is trifluoroacetate. In certain embodiments, Q of Formula (I) is trichloroacetate. In certain embodiments, Q of Formula (I) is $NO_2^-$. In certain embodiments, Q of Formula (I) is $NO_3^-$. In certain embodiments, Q of Formula (I) is $H_2PO_4^-$. In certain embodiments, Q of Formula (I) is $PF_6^-$. In certain embodiments, Q of Formula (I) is $HF^{2-}$. In certain embodiments, Q of Formula (I) is $HSO_4^-$. In certain embodiments, Q of Formula (I) is $SbF_6^-$. In certain embodiments, Q of Formula (I) is $ClO_4^-$. In certain embodiments, Q of Formula (I) is $SO_4^{-2}$. In certain embodiments, Q of Formula (I) is $(R^6)SO_3^-$. In certain embodiments, Q of Formula (I) is $OTf^-$. In certain embodiments, Q of Formula (I) is $OTs^-$. In certain embodiments, Q of Formula (I) is $ONf^-$. In certain embodiments, Q of Formula (I) is $ONs^-$. In certain embodiments, Q of Formula (I) is $BF_4^-$. In certain embodiments, Q of Formula (I) is $B(R^6)_4^-$. In certain embodiments, Q of Formula (I) is $B(R^6)_4^-$. In certain embodiments, Q of Formula (I) is fluoro. In certain embodiments, Q of Formula (I) is chloro. In certain embodiments, Q of Formula (I) is bromo. In certain embodiments, Q of Formula (I) is iodo.

In certain embodiments, A is LiX, $MgX_2$, $ScX_3$, $ScR^6_3$, $YX_3$, $YR^6_3$, $BR^6_3$, $BX_3$, $TiX_4$, $TiR^6_4$, $ZrX_4$, $ZrR^6_4$, $FeX_3$, $FeR^6_3$, $ZnX_2$, $ZnR^6_2$, $AlX_3$, $AlR^6_3$, $InX_3$, $InR^6_3$, $SiX_4$, $SiR^6_4$, $SnX_2$, $SnR^6_2$, $SnX_4$, $SnR^6_4$, $BiX_3$, $BiR^6_3$, m is 1, and v is 0, wherein X is halogen or Q, and $R^6$ is defined as above. In certain embodiments, A is LiX. In certain embodiments, A is $MgX_2$. In certain embodiments, A is $ScX_3$. In certain embodiments, A is $ScR^6_3$. In certain embodiments, A is $YX_3$. In certain embodiments, A is $YR^6_3$. In certain embodiments, A is $BR^6_3$. In certain embodiments, A is $BX_3$. In certain embodiments, A is $TiX_4$. In certain embodiments, A is $TiR^6_4$. In certain embodiments, A is $ZrX_4$. In certain embodiments, A is $ZrR^6_4$. In certain embodiments, A is $AlX_3$. In certain embodiments, A is $AlR^6_3$. In certain embodiments, A is $InX_3$. In certain embodiments, A is $InR^6_3$. In certain embodiments, A is $SiX_4$. In certain embodiments, A is $SiR^6_4$. In certain embodiments, A is $SnX_2$. In certain embodiments, A is $SnR^6_2$. In certain embodiments, A is $BiX_3$. In certain embodiments, A is $BiR^6_3$.

In another aspect, the present invention is directed to a compound of Formula (II):

wherein

S is an organic substrate;

Q is an anion;

$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-NH_2$, $-NHR^7$, $-N(R^7)_2$, $-OH$, $-SH$, $-SO_2R^7$, $-SOR^7$, $-SO_2NR^7_2$, and $-SR^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and $R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, $-NH_2$, $-NHR^7$, $-N(R^7)_2$, $-OH$, $-SH$, $-SO_2R^7$, $-SOR^7$, $-SO_2NR^7_2$, and $-SR^7$.

In certain embodiments, $R^1$ and $R^2$ of Formula (II) are independently $C_{6-10}$ aryl, optionally substituted with 0 to 5 occurrences of $R^5$. In certain embodiments, $R^1$ and $R^2$ of Formula (II) are independently 5-10 membered heteroaryl, optionally substituted with 0 to 5 occurrences of $R^5$. In certain embodiments, $R^1$ and $R^2$ of Formula (II) are independently 4-10 membered heterocyclyl, optionally substituted with 0 to 5 occurrences of $R^5$. In certain embodiments, $R^1$ and $R^2$ of Formula (II) are independently 3-10 membered carbocyclyl, optionally substituted with 0 to 5 occurrences of $R^5$.

In certain embodiments, the compound of Formula (II) is a compound of Formula (II-a):

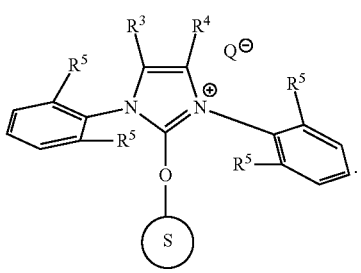

(II-a)

In certain embodiments, the compound of Formula (II) is a compound of Formula (II-b):

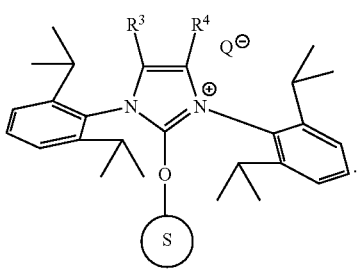

(II-b)

In certain embodiments, R³ of Formula (II) is hydrogen. In certain embodiments, R⁴ of Formula (II) is hydrogen. In certain embodiments, both R³ and R⁴ of Formula (II) are hydrogen.

In certain embodiments, the compound of Formula (II) is a compound of Formula (II-c):

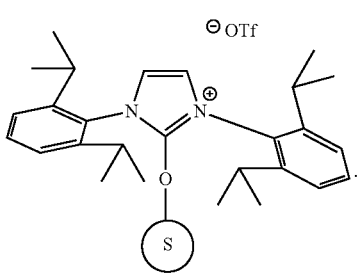

(II-c)

In certain embodiments, the compound of Formula (II) is a compound of Formula (II-d):

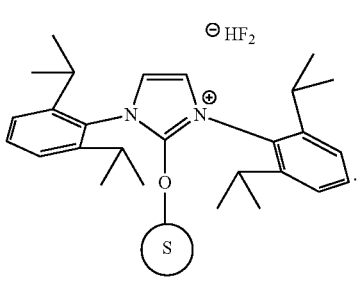

(II-d)

In certain embodiments, the compound of Formula (II) is a compound of Formula (II-e):

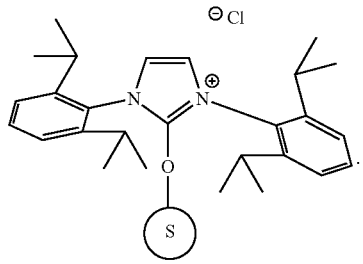

(II-e)

In certain embodiments, the compound of Formula (II) is a compound of Formula (II-f):

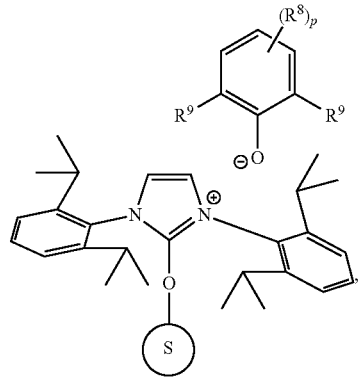

(II-f)

wherein each occurrence of $R^8$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —N($R^{8a}$)₂, —O$R^{8a}$, —CO₂$R^{8a}$, —SO₂$R^{8a}$, —SO$R^{8a}$, —SO₂N($R^{8a}$)₂, and —S$R^{8a}$;

each occurrence of $R^9$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, and optionally substituted 4-10 membered heterocyclylalkyl, acyl, —N($R^{9a}$)₂, —O$R^{9a}$, —CO₂$R^{9a}$, —SO₂$R^{9a}$, —SO$R^{9a}$, —SO₂N($R^{9a}$)₂, and —S$R^{9a}$;

each occurrence of $R^{8a}$ or $R^{9a}$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^{8a}$ or $R^{9a}$ groups are taken together with their intervening atoms to form an optionally substituted heterocyclic ring; and p is 0, 1, 2, or 3.

In certain embodiments, the compound of Formula (II) is a compound of Formula (II-g):

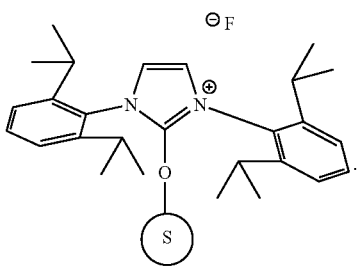

(II-g)

In certain embodiments, the compound of Formula (II) is a compound of Formula (II-h):

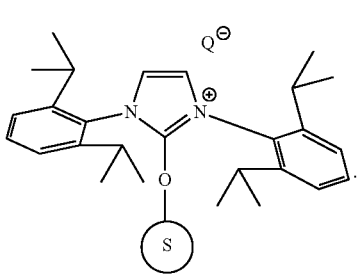

(II-h)

In certain embodiments, Q of Formula (II) is any suitable counterion. In certain embodiments, Q of Formula (II) is

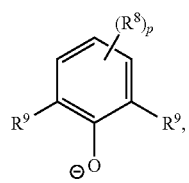

halogen (e.g., fluoro, chloro, bromo, or iodo), trifluoroacetate, trichloroacetate, $NO_2^-$, $NO_3^-$, $H_2PO_4^-$, $PF_6^-$, $HF^{2-}$, $HSO_4^-$, $SbF_6^-$, $ClO_4^-$, $SO_4^{-2}$, $(R^6)SO_3^-$, $OTf^-$, $OTs^-$, $ONf^-$, $ONs^-$, $BF_4^-$, or $B(R^6)_4^-$, wherein $R^6$ is $C_{1-6}$ alkyl, —$OR^7$, $C_{6-10}$ aryl, $C_{6-10}$ aralkyl, 5-10 membered heteroaryl, 5-10 membered heteroaralkyl, 4-10 membered heterocyclylalkyl, 3-10 membered carbocyclyl, or 3-10 membered carbocyclylalkyl, each of which is optionally substituted with 0 to 5 occurrences of $R^5$. In certain embodiments, Q of Formula (II) is

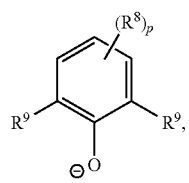

In certain embodiments, Q of Formula (II) is trifluoroacetate. In certain embodiments, Q of Formula (II) is trichloroacetate. In certain embodiments, Q of Formula (II) is $NO_2^-$. In certain embodiments, Q of Formula (II) is $NO_3^-$. In certain embodiments, Q of Formula (II) is $H_2PO_4^-$. In certain embodiments, Q of Formula (II) is $PF_6^-$. In certain embodiments, Q of Formula (II) is $HF^{2-}$. In certain embodiments, Q of Formula (II) is $HSO_4^-$. In certain embodiments, Q of Formula (II) is $SbF_6^-$. In certain embodiments, Q of Formula (II) is $ClO_4^-$. In certain embodiments, Q of Formula (II) is $SO_4^{-2}$. In certain embodiments, Q of Formula (II) is $(R^6)SO_3^-$. In certain embodiments, Q of Formula (II) is $OTf^-$. In certain embodiments, Q of Formula (II) is $OTs^-$. In certain embodiments, Q of Formula (II) is $ONf^-$. In certain embodiments, Q of Formula (II) is $ONs^-$. In certain embodiments, Q of Formula (II) is $BF_4^-$. In certain embodiments, Q of Formula (II) is $B(R^6)_4^-$. In certain embodiments, Q of Formula (II) is fluoro. In certain embodiments, Q of Formula (II) is chloro. In certain embodiments, Q of Formula (II) is bromo. In certain embodiments, Q of Formula (II) is iodo.

In another aspect, the present invention is directed to a compound of Formula (III):

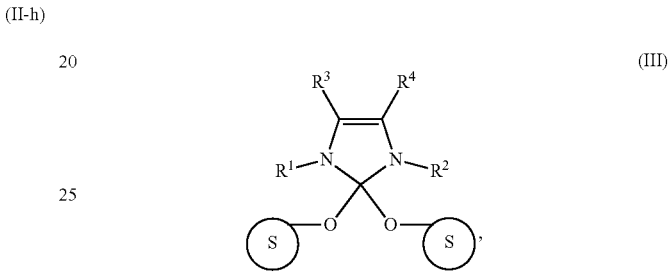

(III)

wherein

S is an organic substrate;

$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7_2$, and —$SR^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and $R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7_2$, and —$SR^7$.

In certain embodiments, $R^1$ and $R^2$ of Formula (III) are independently $C_{6-10}$ aryl, optionally substituted with 0 to 5 occurrences of $R^5$. In certain embodiments, $R^1$ and $R^2$ of Formula (III) are independently 5-10 membered heteroaryl, optionally substituted with 0 to 5 occurrences of R⁵. In certain embodiments, R¹ and R² of Formula (III) are independently 4-10 membered heterocyclyl, optionally substituted with 0 to 5 occurrences of R⁵. In certain embodiments, R¹ and R² of Formula (III) are independently 3-10 membered carbocyclyl, optionally substituted with 0 to 5 occurrences of R⁵.

In certain embodiments, the compound of Formula (III) is a compound of Formula (III-a):

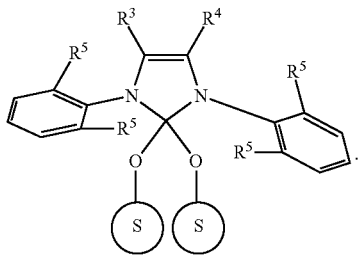

(III-a)

In certain embodiments, the compound of Formula (III) is a compound of Formula (III-b):

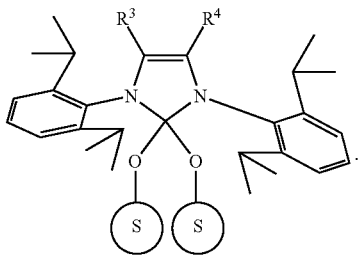

(III-b)

In certain embodiments, R³ of Formula (III) is hydrogen. In certain embodiments, R⁴ of Formula (III) is hydrogen. In certain embodiments, both R³ and R⁴ of Formula (III) are hydrogen.

In certain embodiments, the compound of Formula (III) is a compound of Formula (III-c):

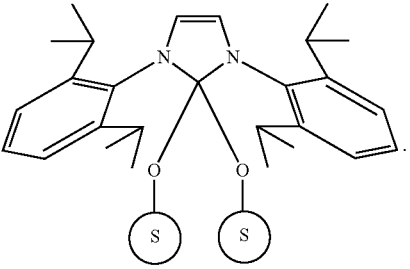

(III-c)

In another aspect, the present invention is directed to a compound of Formula (IV):

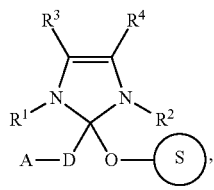

(IV)

wherein

S is an organic substrate;

D is oxygen or sulfur;

A is hydrogen or a Lewis acid;

R¹ and R² are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of R⁵;

R³ and R⁴ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —NH₂, —NHR⁷, —N(R⁷)₂, —OH, —SH, —SO₂R⁷, —SOR⁷, —SO₂NR⁷₂, and —SR⁷;

R⁷ is independently selected from the group consisting of hydrogen, acyl, optionally substituted aliphatic, optionally substituted carbocyclyl, optionally substituted heterocyclyl, optionally substituted aryl, and optionally substituted heteroaryl, or two R⁷ groups are taken together with their intervening atoms to form an optionally substituted heterocyclic ring; and R⁵ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH₂, —NHR⁷, —N(R⁷)₂, —OH, —SH, —SO₂R⁷, —SOR⁷, —SO₂NR⁷₂, and —SR⁷.

In certain embodiments, R¹ and R² of Formula (IV) are independently $C_{6-10}$ aryl, optionally substituted with 0 to 5 occurrences of R⁵. In certain embodiments, R¹ and R² of Formula (IV) are independently 5-10 membered heteroaryl, optionally substituted with 0 to 5 occurrences of R⁵. In certain embodiments, R¹ and R² of Formula (IV) are independently 4-10 membered heterocyclyl, optionally substituted with 0 to 5 occurrences of R⁵. In certain embodiments, R¹ and R² of Formula (IV) are independently 3-10 membered carbocyclyl, optionally substituted with 0 to 5 occurrences of R⁵.

In certain embodiments, the compound of Formula (IV) is a compound of Formula (IV-a):

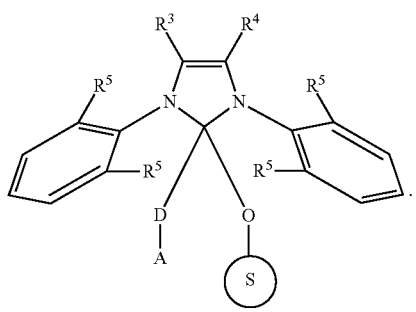

(IV-a)

In certain embodiments, the compound of Formula (IV) is a compound of Formula (IV-b):

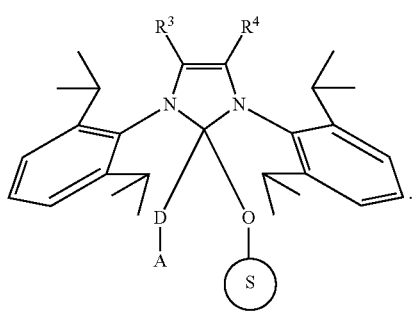

(IV-b)

In certain embodiments, $R^3$ of Formula (IV-b) is hydrogen. In certain embodiments, $R^4$ of Formula (IV-b) is hydrogen. In certain embodiments, both $R^3$ and $R^4$ of Formula (IV-b) are hydrogen.

In certain embodiments, the compound of Formula (IV) is a compound of Formula (IV-c):

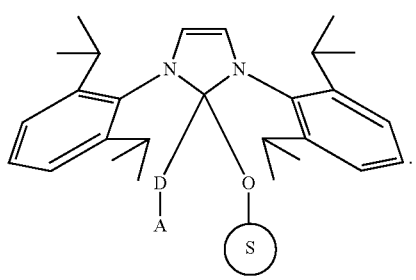

(IV-c)

In another aspect, the present invention is directed to a compound of Formula (IV):

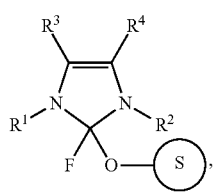

(V)

wherein

S is an organic substrate;

$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —NH$_2$, —NHR$^7$, —N(R$^7$)$_2$, —OH, —SH, —SO$_2$R$^7$, —SOR$^7$, —SO$_2$NR$^7{}_2$, and —SR$^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and $R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH$_2$, —NHR$^7$, —N(R$^7$)$_2$, —OH, —SH, —SO$_2$R$^7$, —SOR$^7$, —SO$_2$NR$^7{}_2$, and —SR$^7$.

In certain embodiments, $R^1$ and $R^2$ of Formula (V) are independently $C_{6-10}$ aryl, optionally substituted with 0 to 5 occurrences of $R^5$. In certain embodiments, $R^1$ and $R^2$ of Formula (V) are independently 5-10 membered heteroaryl, optionally substituted with 0 to 5 occurrences of $R^5$. In certain embodiments, $R^1$ and $R^2$ of Formula (V) are independently 4-10 membered heterocyclyl, optionally substituted with 0 to 5 occurrences of $R^5$. In certain embodiments, $R^1$ and $R^2$ of Formula (V) are independently 3-10 membered carbocyclyl, optionally substituted with 0 to 5 occurrences of $R^5$.

In certain embodiments, the compound of Formula (V) is a compound of Formula (V-a):

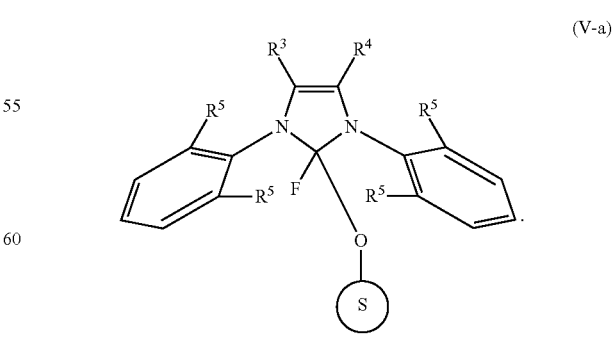

(V-a)

In certain embodiments, the compound of Formula (V) is a compound of Formula (V-b):

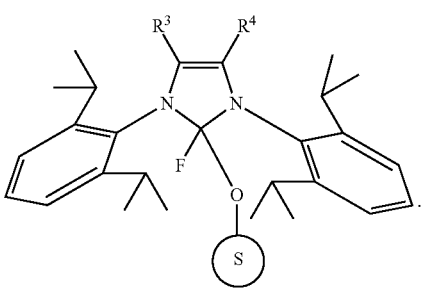

(V-b)

In certain embodiments, $R^3$ of Formula (V-b) is hydrogen. In certain embodiments, $R^4$ of Formula (V-b) is hydrogen. In certain embodiments, both $R^3$ and $R^4$ of Formula (V-b) are hydrogen.

In certain embodiments, the compound of Formula (V) is a compound of Formula (V-c):

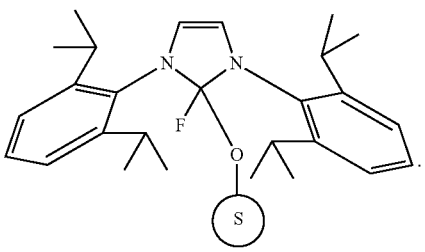

(V-c)

In another aspect, the present invention is directed to a compound of Formula (VI):

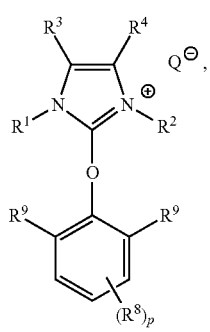

(VI)

wherein

Q is an anion;

$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7_2$, and —$SR^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and $R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7_2$, and —$SR^7$;

each occurrence of $R^8$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$N(R^{8a})_2$, —$OR^{8a}$, —$CO_2R^{8a}$, —$SO_2R^{8a}$, —$SOR^{8a}$, —$SO_2N(R^{8a})_2$, and —$SR^{8a}$;

each occurrence of $R^9$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, and optionally substituted 4-10 membered heterocyclylalkyl, acyl, —$N(R^{9a})_2$, —$OR^{9a}$, —$CO_2R^{9a}$, —$SO_2R^{9a}$, —$SOR^{9a}$, —$SO_2N(R^{9a})_2$, and —$SR^{9a}$;

each occurrence of $R^{8a}$ or $R^{9a}$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^{8a}$ or $R^{9a}$ groups are taken together with their intervening atoms to form an optionally substituted heterocyclic ring; and p is 0, 1, 2, or 3.

In certain embodiments, $R^1$ and $R^2$ of Formula (VI) are independently $C_{6-10}$ aryl, optionally substituted with 0 to 5 occurrences of $R^5$. In certain embodiments, $R^1$ and $R^2$ of Formula (VI) are independently 5-10 membered heteroaryl, optionally substituted with 0 to 5 occurrences of $R^5$. In certain embodiments, $R^1$ and $R^2$ of Formula (VI) are independently 4-10 membered heterocyclyl, optionally substituted with 0 to 5 occurrences of $R^5$. In certain embodiments, $R^1$ and $R^2$ of Formula (VI) are independently 3-10 membered carbocyclyl, optionally substituted with 0 to 5 occurrences of $R^5$.

In certain embodiments, the compound of Formula (VI) is a compound of Formula (VI-a):

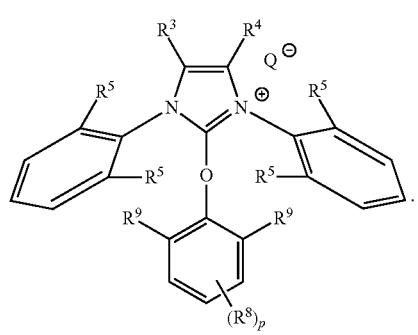 (VI-a)

In certain embodiments, the compound of Formula (VI) is a compound of Formula (VI-b):

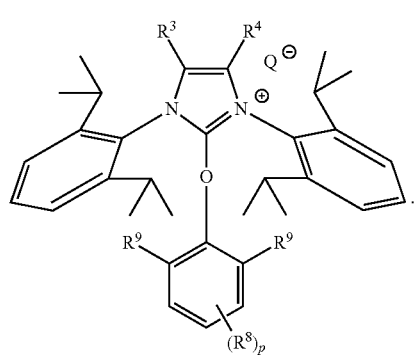 (VI-b)

In certain embodiments, R³ of Formula (VI) is hydrogen. In certain embodiments, R⁴ of Formula (VI) is hydrogen. In certain embodiments, both R³ and R⁴ of Formula (VI) are hydrogen.

In certain embodiments, the compound of Formula (VI) is a compound of Formula (VI-c):

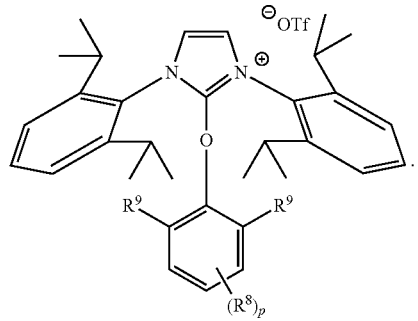 (VI-c)

In certain embodiments, the compound of Formula (VI) is a compound of Formula (VI-d):

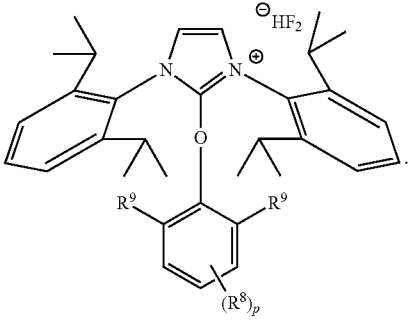 (VI-d)

In certain embodiments, the compound of Formula (VI) is a compound of Formula (VI-e):

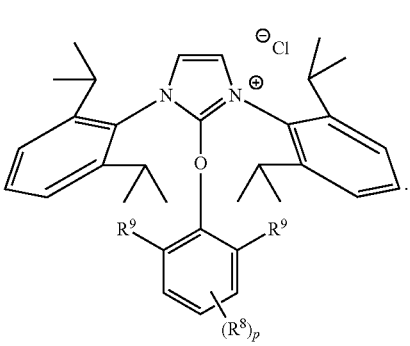 (VI-e)

In certain embodiments, the compound of Formula (VI) is a compound of Formula (VI-f):

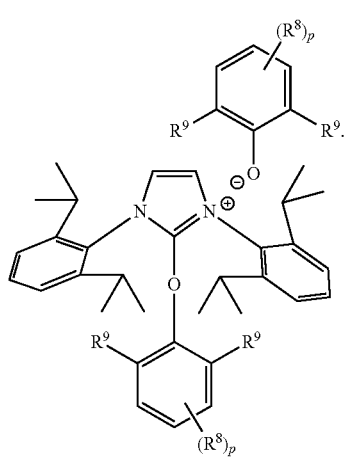 (VI-f)

In certain embodiments, the compound of Formula (VI) is a compound of Formula (VI-g):

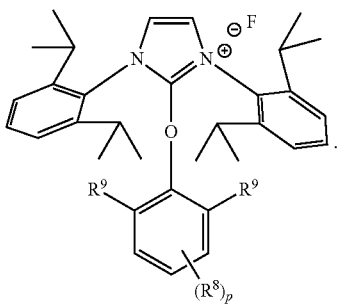

(VI-g)

In certain embodiments, the compound of Formula (VI) is a compound of Formula (VI-h):

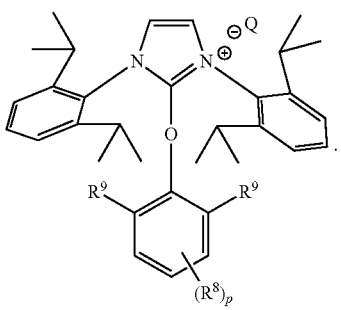

(VI-h)

In certain embodiments, Q of Formula (VI) is any suitable counterion. In certain embodiments, Q of Formula (VI) is

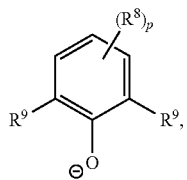

halogen (e.g., fluoro, chloro, bromo, or iodo), trifluoroacetate, trichloroacetate, $NO_2^-$, $NO_3^-$, $H_2PO_4^-$, $PF_6^-$, $HF^{2-}$, $HSO_4^-$, $SbF_6^-$, $ClO_4^-$, $SO_4^{-2}$, $(R^6)SO_3^-$, $OTf^-$, $OTs^-$, $ONf^-$, $ONs^-$, $BF_4^-$, or $B(R^6)_4^-$, wherein $R^6$ is $C_{1-6}$ alkyl, $-OR^7$, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, or 3-10 membered carbocyclylalkyl, each of which is optionally substituted with 0 to 5 occurrences of $R^5$. In certain embodiments, Q of Formula (VI) is

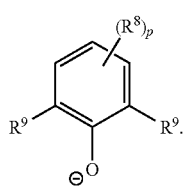

In certain embodiments, Q of Formula (VI) is trifluoroacetate. In certain embodiments, Q of Formula (VI) is trichloroacetate. In certain embodiments, Q of Formula (VI) is $NO_2^-$. In certain embodiments, Q of Formula (VI) is $NO_3^-$. In certain embodiments, Q of Formula (VI) is $H_2PO_4^-$. In certain embodiments, Q of Formula (VI) is $PF_6^-$. In certain embodiments, Q of Formula (VI) is $HF^{2-}$. In certain embodiments, Q of Formula (VI) is $HSO_4^-$. In certain embodiments, Q of Formula (VI) is $SbF_6^-$. In certain embodiments, Q of Formula (VI) is $ClO_4^-$. In certain embodiments, Q of Formula (VI) is $SO_4^{-2}$. In certain embodiments, Q of Formula (VI) is $(R^6)SO_3^-$. In certain embodiments, Q of Formula (VI) is $OTf^-$. In certain embodiments, Q of Formula (VI) is $OTs^-$. In certain embodiments, Q of Formula (VI) is $ONf^-$. In certain embodiments, Q of Formula (VI) is $ONs^-$. In certain embodiments, Q of Formula (VI) is $BF_4^-$. In certain embodiments, Q of Formula (VI) is $B(R^6)_4^-$. In certain embodiments, Q of Formula (VI) is $B(R^6)_4^-$. In certain embodiments, Q of Formula (VI) is fluoro. In certain embodiments, Q of Formula (VI) is chloro. In certain embodiments, Q of Formula (VI) is bromo. In certain embodiments, Q of Formula (VI) is iodo.

In another aspect, the present invention is directed to a method of replacing a hydroxyl group on an organic compound with a fluorine atom, the method comprising contacting a compound of Formula (I):

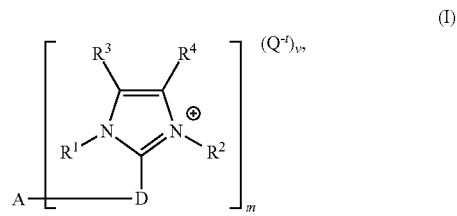

(I)

wherein

D is oxygen or sulfur;

A is hydrogen or a Lewis acid;

Q is an anion;

$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-NH_2$, $-NHR^7$, $-N(R^7)_2$, $-OH$, $-SH$, $-SO_2R^7$, $-SOR^7$, $-SO_2NR^7_2$, and $-SR^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring;

$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH$_2$, —NHR$^7$, —N(R$^7$)$_2$, —OH, —SH, —SO$_2$R$^7$, —SOR$^7$, —SO$_2$NR$^7$$_2$, and —SR$^7$;

t is the anion charge number, ranging from 1-3;

v is 0-3;

m is 1-5;

with an organic compound under conditions sufficient to fluorinate the organic compound, thereby providing a fluorinated organic compound.

In certain embodiments of the method, R$^1$ and R$^2$ of Formula (I) are independently C$_{6-10}$ aryl, optionally substituted with 0 to 5 occurrences of R$^5$. In certain embodiments of the method, R$^1$ and R$^2$ of Formula (I) are independently 5-10 membered heteroaryl, optionally substituted with 0 to 5 occurrences of R$^5$. In certain embodiments of the method, R$^1$ and R$^2$ of Formula (I) are independently 4-10 membered heterocyclyl, optionally substituted with 0 to 5 occurrences of R$^5$. In certain embodiments of the method, R$^1$ and R$^2$ of Formula (I) are independently 3-10 membered carbocyclyl, optionally substituted with 0 to 5 occurrences of R$^5$.

In certain embodiments, the method comprises contacting a compound of Formula (I-c):

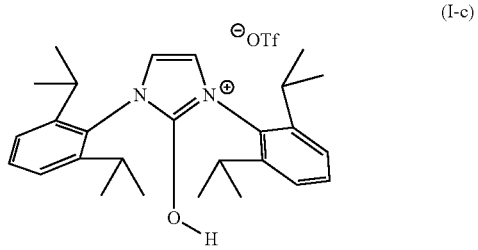 [SMILES: CC(C)c1cccc(C(C)C)c1-n1cc[n+](-c2c(C(C)C)cccc2C(C)C)c1O ; "OTf"]

(I-c)

with an organic compound under conditions sufficient to fluorinate the organic compound, thereby providing a fluorinated organic compound.

In certain embodiments, the fluorinated organic compound comprises $^{18}$F. In certain embodiments, the hydroxyl group-containing organic substrate is aliphatic. In certain embodiments, the hydroxyl group-containing organic substrate is aryl. In certain embodiments, the hydroxyl group-containing organic substrate is vinyl. In certain embodiments, the hydroxyl group-containing organic substrate is heteroaryl. In certain embodiments, the hydroxyl group-containing organic substrate comprises a tautomer of a heteroaryl hydroxyl group. In certain embodiments, the hydroxyl group-containing organic substrate is heterocyclic. In certain embodiments, the hydroxyl group-containing organic substrate comprises a tautomer of a heterocyclic hydroxyl group. In certain embodiments, the method further comprises a source of fluorine. In certain embodiments, the fluorine source is a fluoride salt. In certain embodiments, the fluorine source is a sodium, potassium, or cesium fluoride salt. In certain embodiments, the fluorine source is the counter ion Q. In certain embodiments, the method comprises approximately 1-10 equivalents of a fluorine source. In certain embodiments, the method comprises approximately 1-5 equivalents of a fluorine source. In certain embodiments, the method comprises approximately 5-10 equivalents of a fluorine source. In certain embodiments, the method comprises approximately 3-5 equivalents of a fluorine source. In certain embodiments, the method comprises greater than 10 equivalents of a fluorine source. In certain embodiments, the fluorine source comprises $^{18}$F. In certain embodiments, the step of contacting is performed in the presence of an organic or inorganic base. In certain embodiments, the base is an inorganic base. In certain embodiments, the base is sodium, potassium, or cesium carbonate. In certain embodiments, the method comprises approximately 1-10 equivalents of a base. In certain embodiments, the method comprises approximately 1-5 equivalents of a base. In certain embodiments, the method comprises approximately 5-10 equivalents of a base. In certain embodiments, the method comprises approximately 3-5 equivalents of a base. In certain embodiments, the method comprises greater than 10 equivalents of a base. In certain embodiments, the step of contacting comprises heating the compound of Formula (I) and the hydroxyl group-containing organic substrate to a temperature of approximately 80-140° C. In certain embodiments, the step of contacting comprises heating the compound of Formula (I) and the hydroxyl group-containing organic substrate to a temperature of approximately 100-120° C. In certain embodiments, the step of contacting comprises heating the compound of Formula (I) and the hydroxyl group-containing organic substrate to a temperature of about 110° C. In certain embodiments, the step of contacting lasts 5 minutes or less. In certain embodiments, the step of contacting lasts 15 minutes or less. In certain embodiments, the step of contacting lasts 30 minutes or less. In certain embodiments, the step of contacting lasts 1 hour or less. In certain embodiments, the step of contacting more than 1 hour. In certain embodiments, the method further comprises purifying the fluorinated organic compound. In certain embodiments, said method is incorporated into an automated process by which PET imaging agents are produced via reaction of hydroxyl group containing organic compounds with a compound of Formula (I), and a source of $^{18}$F. In certain embodiments, the yield of the fluorinated organic compound from the organic compound is at least about 5%. In certain embodiments, the yield of the fluorinated organic compound from the organic compound is at least about 10%. In certain embodiments, the yield of the fluorinated organic compound from the organic compound is at least about 15%. In certain embodiments, the yield of the fluorinated organic compound from the organic compound is at least about 20%. In certain embodiments, the yield of the fluorinated organic compound from the organic compound is at least about 25%. In certain embodiments, the yield of the fluorinated organic compound from the organic compound is at least about 30%. In certain embodiments, the yield of the fluorinated organic compound from the organic compound is at least about 35%. In certain embodiments, the yield of the fluorinated organic compound from the organic compound is at least about 40%. In certain embodiments, the yield of the fluorinated organic compound from the organic compound is at least about 45%. In certain embodiments, the yield of the fluorinated organic compound from the organic compound is at least about 50%. In certain embodiments, the yield of the fluorinated organic compound from the organic compound is at least about 55%. In certain embodiments, the yield of the fluorinated organic compound from the organic compound is at least about 60%. In certain embodiments, the yield of the fluorinated organic compound from the organic compound is at least about 65%. In certain embodiments, the yield of the fluorinated organic compound from the organic compound is at least about 70%. In certain embodiments, the yield of the fluorinated organic compound from the organic compound is at least about 75%. In certain embodiments, the yield of the fluorinated organic compound from the organic compound is at least about 80%. In certain embodiments, the yield of the fluorinated organic compound from the organic compound is at least about 85%. In certain embodiments, the yield of the fluorinated organic compound from the organic compound is at least about 90%. In certain embodiments, the yield of the fluorinated organic compound from the organic compound is at least about 95%. In certain embodiments, the yield of the fluorinated organic compound from the organic compound is greater than 95%.

In another aspect, the present invention provides methods of replacing a hydroxyl group on an organic compound with a fluorine atom, the method comprising exchanging an anion Q of a compound of Formula (II):

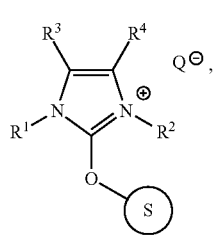
(II)

wherein
S is an organic substrate;
Q is an anion;
$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;
$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7{}_2$, and —$SR^7$;
$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and
$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7{}_2$, and —$SR^7$, with a fluoride or $HF_2$ anion. In certain embodiments, the ion exchange reaction is carried out using an anion exchange resin or anion exchange chromatography.

In certain embodiments of the method, $R^1$ and $R^2$ of Formula (II) are independently $C_{6-10}$ aryl, optionally substituted with 0 to 5 occurrences of $R^5$. In certain embodiments of the method, $R^1$ and $R^2$ of Formula (II) are independently 5-10 membered heteroaryl, optionally substituted with 0 to 5 occurrences of $R^5$. In certain embodiments of the method, $R^1$ and $R^2$ of Formula (II) are independently 4-10 membered heterocyclyl, optionally substituted with 0 to 5 occurrences of $R^5$. In certain embodiments of the method, $R^1$ and $R^2$ of Formula (II) are independently 3-10 membered carbocyclyl, optionally substituted with 0 to 5 occurrences of $R^5$.

In certain embodiments, the method of replacing a hydroxyl group on an organic compound with a fluorine atom comprises exchanging a chloride anion of a compound of Formula (II-e):

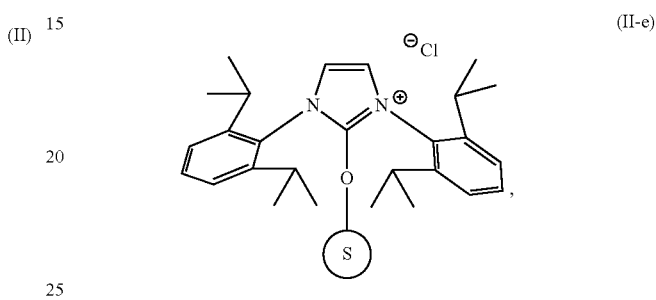
(II-e)

with a fluoride or $HF_2$ anion.

In certain embodiments, the method of replacing a hydroxyl group on an organic compound with a fluorine atom comprises exchanging a phenolate anion of a compound of Formula (II-f):

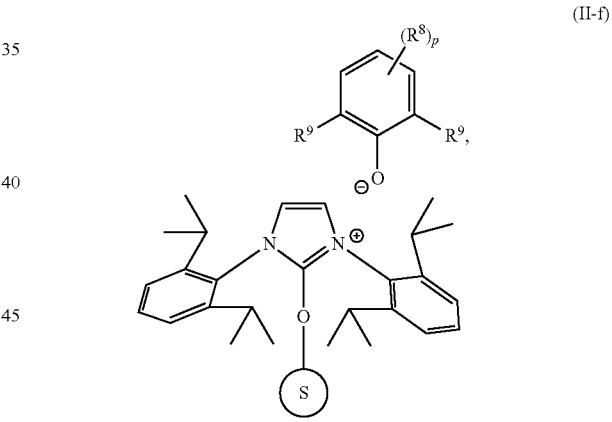
(II-f)

with a fluoride or $HF_2$ anion.

In certain embodiments, the fluorinated organic compound comprises $^{18}F$. In certain embodiments, the hydroxyl group-containing organic substrate is aliphatic. In certain embodiments, the hydroxyl group-containing organic substrate is aryl. In certain embodiments, the hydroxyl group-containing organic substrate is vinyl. In certain embodiments, the hydroxyl group-containing organic substrate is heteroaryl. In certain embodiments, the hydroxyl group-containing organic substrate comprises a tautomer of a heteroaryl hydroxyl group. In certain embodiments, the hydroxyl group-containing organic substrate is heterocyclic. In certain embodiments, the hydroxyl group-containing organic substrate comprises a tautomer of a heterocyclic hydroxyl group. In certain embodiments, the method further comprises a source of fluorine. In certain embodiments, the fluorine source is a fluoride salt. In certain embodiments, the fluorine source is a sodium, potassium, or cesium fluoride salt. In certain embodiments, the fluorine source is the counter ion Q. In certain embodiments, the method comprises approximately 1-10 equivalents of a fluorine source. In certain embodiments, the method comprises approximately 1-5 equivalents of a fluorine source. In certain embodiments, the method comprises approximately 5-10 equivalents of a fluorine source. In certain embodiments, the method comprises approximately 3-5 equivalents of a fluorine source. In certain embodiments, the method comprises greater than 10 equivalents of a fluorine source. In certain embodiments, the fluorine source comprises $^{18}F$. In certain embodiments, the step of contacting is performed in the presence of an organic or inorganic base. In certain embodiments, the base is an inorganic base. In certain embodiments, the base is sodium, potassium, or cesium carbonate. In certain embodiments, the method comprises approximately 1-10 equivalents of a base. In certain embodiments, the method comprises approximately 1-5 equivalents of a base. In certain embodiments, the method comprises approximately 5-10 equivalents of a base. In certain embodiments, the method comprises approximately 3-5 equivalents of a base. In certain embodiments, the method comprises greater than 10 equivalents of a base. In certain embodiments, the step of contacting comprises heating the compound of Formula (II) and a fluorine source. In certain embodiments, the compound of Formula (II) and the fluorine source are heated to a temperature of approximately 80-140° C. In certain embodiments, the compound of Formula (II) and the fluorine source are heated to a temperature of approximately 100-120° C. In certain embodiments, the compound of Formula (II) and the fluorine source are heated to a temperature of about 110° C. In certain embodiments, the step of fluorinating a compound of Formula (II) lasts 5 minutes or less. In certain embodiments, the step of the step of fluorinating a compound of Formula (II) lasts 15 minutes or less. In certain embodiments, the step of the step of fluorinating a compound of Formula (II) lasts 30 minutes or less. In certain embodiments, the step of the step of fluorinating a compound of Formula (II) lasts 1 hour or less. In certain embodiments, the step of contacting lasts more than 1 hour. In certain embodiments, the step of fluorinating a compound of Formula (II) or exchanging the anion Q is carried out in a mixture of water and an organic solvent. In certain embodiments, the step of fluorinating a compound of Formula (II) or exchanging the anion Q is carried out in a mixture of water and dioxane. In certain embodiments, the method further comprises purifying the fluorinated organic compound. In certain embodiments, said method is incorporated into an automated process by which PET imaging agents are produced via reaction of a compound of Formula (II) and a source of $^{18}F$. In certain embodiments, the yield of the fluorinated organic compound from the organic compound is at least about 5%. In certain embodiments, the yield of the fluorinated organic compound from the organic compound is at least about 10%. In certain embodiments, the yield of the fluorinated organic compound from the organic compound is at least about 15%. In certain embodiments, the yield of the fluorinated organic compound from the organic compound is at least about 20%. In certain embodiments, the yield of the fluorinated organic compound from the organic compound is at least about 25%. In certain embodiments, the yield of the fluorinated organic compound from the organic compound is at least about 30%. In certain embodiments, the yield of the fluorinated organic compound from the organic compound is at least about 35%. In certain embodiments, the yield of the fluorinated organic compound from the organic compound is at least about 40%. In certain embodiments, the yield of the fluorinated organic compound from the organic compound is at least about 45%. In certain embodiments, the yield of the fluorinated organic compound from the organic compound is at least about 50%. In certain embodiments, the yield of the fluorinated organic compound from the organic compound is at least about 55%. In certain embodiments, the yield of the fluorinated organic compound from the organic compound is at least about 60%. In certain embodiments, the yield of the fluorinated organic compound from the organic compound is at least about 65%. In certain embodiments, the yield of the fluorinated organic compound from the organic compound is at least about 70%. In certain embodiments, the yield of the fluorinated organic compound from the organic compound is at least about 75%. In certain embodiments, the yield of the fluorinated organic compound from the organic compound is at least about 80%. In certain embodiments, the yield of the fluorinated organic compound from the organic compound is at least about 85%. In certain embodiments, the yield of the fluorinated organic compound from the organic compound is at least about 90%. In certain embodiments, the yield of the fluorinated organic compound from the organic compound is at least about 95%. In certain embodiments, the yield of the fluorinated organic compound from the organic compound is greater than 95%.

In certain embodiments, the method of replacing a hydroxyl group on an organic compound with a fluorine atom comprises exchanging an anion Q of a compound of Formula (II) with a fluoride or $HF_2$ anion. In certain embodiments, the ion exchange reaction is carried out using an anion exchange resin or anion exchange chromatography. In certain embodiments the anion exchange medium is a weak anion exchange resin. In certain embodiments, the anion exchange medium comprises primary, secondary, or tertiary amine functional groups. In certain embodiments, the anion exchange medium is Amberlite® CR5550, Amberlite® FPA51, Amberlite® FPA53, Amberlite® FPA54, Amberlite® FPA55, Amberlite® IRA-67, Amberlite® IRA-67RF, Amberlite® IRA-70RF, Amberlite® IRA-96, Amberlite® IRA-96RF, Amberlite® IRA-96SB, Amberlite® IRA743, Amberlyst® A21, Amberlyst® A23, Diaion® WA10, Diaion® WA30, Dowex® 66, Dowex® 66RF, Dowex® Marathon® WBA, Dowex® Marathon® WBA-2, Dowex® Monosphere® 66, Dowex® Monosphere® 77, Dowex® WGR-2, Dowex® Upcore Mono WB-500, Duolite® A7, Duolite® A568, Lewatit® MonoPlus MP 64, Lewatit® MP-62, Lewatit® VP OC 1065, Toyopearl® DEAE-650M, or TSKgel®. In certain embodiments the anion exchange medium is a strong anion exchange resin. In certain embodiments, the anion exchange medium comprises quaternary ammonium functional groups. In certain embodiments, the anion exchange medium is Amberjet® 4200, Amberjet® 4600, Amberjet® 9000, Amberjet® 9800, Amberjet® UP4000, Amberlite® FPA40, Amberlite® FPA42, Amberlite® FPA90, Amberlite® FPA91, Amberlite® FPA98, Amberlite® IRA-400, Amberlite® IRA-402, Amberlite® IRA-405, Amberlite® IRA-410, Amberlite® IRA-458, Amberlite® IRA-458RF, Amberlite® IRA-478, Amberlite® IRA-743, Amberlite® IRA-900, Amberlite® IRA-900RF, Amberlite® IRA-910, Amberlite® IRA-958, Amberlite® IRN-78, Amberlite® IRN-9766, Amberlyst® A26, Ambersep® 400, Ambersep® 4400, Ambersep® 4550, Ambersep® 900, Ambersep® 920U, Ambersep® 920UHC, Ambersep® 920UXL, Ambersep® 940U, Diaion® HPA25, Dowex® 1X2, Dowex® 1X4, Dowex® 1X8, Dowex® 21K, Dowex® 22, Dowex® 2X8, Dowex® 550A, Dowex® Marathon®, Dowex® Marathon® A, Dowex® Marathon® A2, Dowex®

Marathon® 11, Dowex® Marathon® MSA-1, Dowex® Marathon® MSA-2, Dowex® Monosphere® 550A, Dowex® Monosphere® 550A UPW, Dowex® RPU, Dowex® SBR-C, Dowex® Upcore Mono A2-500, Dowex® Upcore Mono A-500, Dowex® Upcore Mono A-625, Dowex® Upcore Mono MA-600, Dowex® XZ 91419, Imac® HP555, Lewatit® MonoPlus M 500, Lewatit® MP-64, QAE Sephadex® A-50, QAE Sephadex® A-25, Toyopearl® QAE-550C, Toyopearl® SuperQ-650M, Chromafix®, or Chromabond® PS. In certain embodiments, the anion exchange medium is a polystyrene-bicarbonate resin. In order to facilitate exchange of the anion Q, a solution of a compound of Formula (II) is passed over anion exchange medium or through a column containing anion exchange medium which is infused with fluoride or $HF_2$ anions. In certain embodiments, between approximately 5 and 100 mg of anion exchange media is used. In certain embodiments, between approximately 10 and 50 mg of anion exchange media is used. In certain embodiments, approximately 30 mg of anion exchange media is used. In certain embodiments, between approximately 2 and 20 micromoles of a compound of Formula (II) is used. In certain embodiments, between approximately 5 and 10 micromoles of a compound of Formula (II) is used. In certain embodiments, approximately 8 micromoles of a compound of Formula (II) is used. In certain embodiments, the compound of Formula (II) is passed over anion exchange medium or through a column containing anion exchange medium using between 0.1 and 10 ml of solvent. In certain embodiments, the compound of Formula (II) is passed over anion exchange medium or through a column containing anion exchange medium using between 0.2 and 1 ml of solvent. In certain embodiments, the compound of Formula (II) is passed over anion exchange medium or through a column containing anion exchange medium using about 5 ml of solvent.

In another aspect, the present invention is directed to a method of producing a compound of Formula (II):

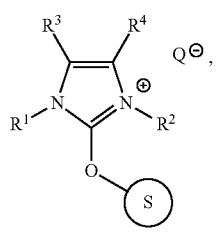

(II)

wherein
S is an organic substrate;
Q is an anion;
$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;
$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7_2$, and —$SR^7$;
$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and
$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7_2$, and —$SR^7$,
the method comprising contacting a compound of Formula (VI):

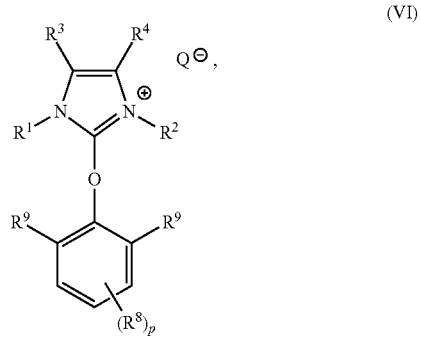

(VI)

wherein
Q is an anion;
$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;
$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7_2$, and —$SR^7$;
$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and
$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH$_2$, —NHR$^7$, —N(R$^7$)$_2$, —OH, —SH, —SO$_2$R$^7$, —SOR$^7$, —SO$_2$NR$^7_2$, and —SR$^7$;

each occurrence of R$^8$ is independently selected from the group consisting of C$_{1-6}$ alkyl, C$_{2-6}$ alkenyl, C$_{2-6}$ alkynyl, nitro, cyano, halo, C$_{1-6}$ haloalkyl, C$_{1-6}$ alkoxy, optionally substituted C$_{6-10}$ aryl, optionally substituted C$_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —N(R$^{8a}$)$_2$, —OR$^{8a}$, —CO$_2$R$^{8a}$, —SO$_2$R$^{8a}$, —SOR$^{8a}$, —SO$_2$N(R$^{8a}$)$_2$, and —SR$^{8a}$;

each occurrence of R$^9$ is independently selected from the group consisting of C$_{1-6}$ alkyl, C$_{2-6}$ alkenyl, C$_{2-6}$ alkynyl, nitro, cyano, halo, C$_{1-6}$ haloalkyl, C$_{1-6}$ alkoxy, optionally substituted C$_{6-10}$ aryl, optionally substituted C$_{6-10}$ aralkyl, optionally substituted 5-10 membered heteroaryl, optionally substituted 4-10 membered heterocyclyl, optionally substituted 3-10 membered carbocyclyl, and optionally substituted 4-10 membered heterocyclylalkyl, acyl, —N(R$^{9a}$)$_2$, —OR$^{9a}$, —CO$_2$R$^{9a}$, —SO$_2$R$^{9a}$, —SOR$^{9a}$, —SO$_2$N(R$^{9a}$)$_2$, and —SR$^{9a}$;

each occurrence of R$^{8a}$ or R$^{9a}$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two R$^{8a}$ or R$^{9a}$ groups are taken together with their intervening atoms to form an optionally substituted heterocyclic ring; and p is 0, 1, 2, or 3, with a hydroxyl group-containing organic substrate and exchanging

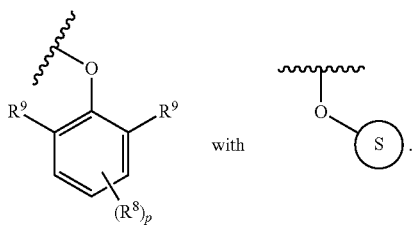

In certain embodiments of the method, R$^1$ and R$^2$ of Formula (II) and (IV) are independently C$_{6-10}$ aryl, optionally substituted with 0 to 5 occurrences of R$^5$. In certain embodiments of the method, R$^1$ and R$^2$ of Formula (II) and (IV) are independently 5-10 membered heteroaryl, optionally substituted with 0 to 5 occurrences of R$^5$. In certain embodiments of the method, R$^1$ and R$^2$ of Formula (II) and (IV) are independently 4-10 membered heterocyclyl, optionally substituted with 0 to 5 occurrences of R$^5$. In certain embodiments of the method, R$^1$ and R$^2$ of Formula (II) and (IV) are independently 3-10 membered carbocyclyl, optionally substituted with 0 to 5 occurrences of R$^5$.

In certain embodiments, the method further comprises the step of replacing a hydroxyl group of an organic compound with a fluorine atom to prepare a fluorinated organic compound. In certain embodiments, the fluorinated organic compound comprises $^{18}$F. In certain embodiments, the hydroxyl group-containing organic compound is aliphatic. In certain embodiments, the hydroxyl group-containing organic substrate is aryl. In certain embodiments, the hydroxyl group-containing organic substrate is vinyl. In certain embodiments, the hydroxyl group-containing organic substrate is heteroaryl. In certain embodiments, the hydroxyl group-containing organic substrate comprises a tautomer of a heteroaryl hydroxyl group. In certain embodiments, the hydroxyl group-containing organic substrate is heterocyclic. In certain embodiments, the hydroxyl group-containing organic substrate comprises a tautomer of a heterocyclic hydroxyl group. In certain embodiments, the method further comprises a source of fluorine. In certain embodiments, the fluorine source is a fluoride salt. In certain embodiments, the fluorine source is a sodium, potassium, or cesium fluoride salt. In certain embodiments, the fluorine source is the counter ion Q. In certain embodiments, the method comprises approximately 1-10 equivalents of a fluorine source. In certain embodiments, the method comprises approximately 1-5 equivalents of a fluorine source. In certain embodiments, the method comprises approximately 5-10 equivalents of a fluorine source. In certain embodiments, the method comprises approximately 3-5 equivalents of a fluorine source. In certain embodiments, the method comprises greater than 10 equivalents of a fluorine source. In certain embodiments, the fluorine source comprises $^{18}$F. In certain embodiments, the step of contacting is performed in the presence of an organic or inorganic base. In certain embodiments, the base is an inorganic base. In certain embodiments, the base is sodium, potassium, or cesium carbonate. In certain embodiments, the method comprises approximately 1-10 equivalents of a base. In certain embodiments, the method comprises approximately 1-5 equivalents of a base. In certain embodiments, the method comprises approximately 5-10 equivalents of a base. In certain embodiments, the method comprises approximately 3-5 equivalents of a base. In certain embodiments, the method comprises greater than 10 equivalents of a base. In certain embodiments, the step of contacting comprises heating the compound of Formula (II) and a fluorine source. In certain embodiments, the compound of Formula (II) and the fluorine source are heated to a temperature of approximately 80-140° C. In certain embodiments, the compound of Formula (II) and the fluorine source are heated to a temperature of approximately 100-120° C. In certain embodiments, the compound of Formula (II) and the fluorine source are heated to a temperature of about 110° C. In certain embodiments, the step of contacting lasts 5 minutes or less. In certain embodiments, the step of the step of contacting lasts 15 minutes or less. In certain embodiments, the step of the step of contacting lasts 30 minutes or less. In certain embodiments, the step of the step of contacting lasts 1 hour or less. In certain embodiments, the step of contacting lasts more than 1 hour. In certain embodiments, the step of fluorinating a compound of Formula (II) or exchanging the anion Q is carried out in a mixture of water and an organic solvent. In certain embodiments, the step of fluorinating a compound of Formula (II) or exchanging the anion Q is carried out in a mixture of water and dioxane. In certain embodiments, the method further comprises purifying the fluorinated organic compound. In certain embodiments, said method is incorporated into an automated process by which PET imaging agents are produced via reaction of a compound of Formula (II) and a source of $^{18}$F. In certain embodiments, the yield of the fluorinated organic compound from the organic compound is at least about 5%. In certain embodiments, the yield of the fluorinated organic compound from the organic compound is at least about 10%. In certain embodiments, the yield of the fluorinated organic compound from the organic compound is at least about 15%. In certain embodiments, the yield of the fluorinated organic compound from the organic compound is at least about 20%. In certain embodiments, the yield of the fluorinated organic compound from the organic compound is at least about 25%. In certain embodiments, the yield of the fluorinated organic compound from the organic compound is at least about 30%. In certain embodiments, the yield of the fluorinated organic compound from the organic compound is at least about 35%. In certain embodiments, the yield of the fluorinated organic compound from the organic compound is at least about 40%. In certain embodiments, the yield of the fluorinated organic compound from the organic compound is at least about 45%. In certain embodiments, the yield of the fluorinated organic compound from the organic compound is at least about 50%. In certain embodiments, the yield of the fluorinated organic compound from the organic compound is at least about 55%. In certain embodiments, the yield of the fluorinated organic compound from the organic compound is at least about 60%. In certain embodiments, the yield of the fluorinated organic compound from the organic compound is at least about 65%. In certain embodiments, the yield of the fluorinated organic compound from the organic compound is at least about 70%. In certain embodiments, the yield of the fluorinated organic compound from the organic compound is at least about 75%. In certain embodiments, the yield of the fluorinated organic compound from the organic compound is at least about 80%. In certain embodiments, the yield of the fluorinated organic compound from the organic compound is at least about 85%. In certain embodiments, the yield of the fluorinated organic compound from the organic compound is at least about 90%. In certain embodiments, the yield of the fluorinated organic compound from the organic compound is at least about 95%. In certain embodiments, the yield of the fluorinated organic compound from the organic compound is greater than 95%.

In certain embodiments, the method further comprises exchanging an anion Q of a compound of Formula (II) with a fluoride or $HF_2$ anion. In certain embodiments, the ion exchange reaction is carried out using an anion exchange resin or anion exchange chromatography. In certain embodiments the anion exchange medium is a weak anion exchange resin. In certain embodiments, the anion exchange medium comprises primary, secondary, or tertiary amine functional groups. In certain embodiments, the anion exchange medium is Amberlite® CR5550, Amberlite® FPA51, Amberlite® FPA53, Amberlite® FPA54, Amberlite® FPA55, Amberlite® IRA-67, Amberlite® IRA-67RF, Amberlite® IRA-70RF, Amberlite® IRA-96, Amberlite® IRA-96RF, Amberlite® IRA-96SB, Amberlite® IRA743, Amberlyst® A21, Amberlyst® A23, Diaion® WA10, Diaion® WA30, Dowex® 66, Dowex® 66RF, Dowex® Marathon® WBA, Dowex® Marathon® WBA-2, Dowex® Monosphere® 66, Dowex® Monosphere® 77, Dowex® WGR-2, Dowex® Upcore Mono WB-500, Duolite® A7, Duolite® A568, Lewatit® MonoPlus MP 64, Lewatit® MP-62, Lewatit® VP OC 1065, Toyopearl® DEAE-650M, or TSKgel®. In certain embodiments the anion exchange medium is a strong anion exchange resin. In certain embodiments, the anion exchange medium comprises quaternary ammonium functional groups. In certain embodiments, the anion exchange medium is Amberjet® 4200, Amberjet® 4600, Amberjet® 9000, Amberjet® 9800, Amberjet® UP4000, Amberlite® FPA40, Amberlite® FPA42, Amberlite® FPA90, Amberlite® FPA91, Amberlite® FPA98, Amberlite® IRA-400, Amberlite® IRA-402, Amberlite® IRA-405, Amberlite® IRA-410, Amberlite® IRA-458, Amberlite® IRA-458RF, Amberlite® IRA-478, Amberlite® IRA-743, Amberlite® IRA-900, Amberlite® IRA-900RF, Amberlite® IRA-910, Amberlite® IRA-958, Amberlite® IRN-78, Amberlite® IRN-9766, Amberlyst® A26, Ambersep® 400, Ambersep® 4400, Ambersep® 4550, Ambersep® 900, Ambersep® 920U, Ambersep® 920UHC, Ambersep® 920UXL, Ambersep® 940U, Diaion® HPA25, Dowex® 1X2, Dowex® 1X4, Dowex® 1X8, Dowex® 21K, Dowex® 22, Dowex® 2X8, Dowex® 550A, Dowex® Marathon®, Dowex® Marathon® A, Dowex® Marathon® A2, Dowex® Marathon® 11, Dowex® Marathon® MSA-1, Dowex® Marathon® MSA-2, Dowex® Monosphere® 550A, Dowex® Monosphere® 550A UPW, Dowex® RPU, Dowex® SBR-C, Dowex® Upcore Mono A2-500, Dowex® Upcore Mono A-500, Dowex® Upcore Mono A-625, Dowex® Upcore Mono MA-600, Dowex® XZ 91419, Imac® HP555, Lewatit® MonoPlus M 500, Lewatit® MP-64, QAE Sephadex® A-50, QAE Sephadex® A-25, Toyopearl® QAE-550C, Toyopearl® SuperQ-650M, Chromafix®, or Chromabond® PS. In certain embodiments, the anion exchange medium is a polystyrene-bicarbonate resin. In order to facilitate exchange of the anion Q, a solution of a compound of Formula (II) is passed over anion exchange medium or through a column containing anion exchange medium which is infused with fluoride or $HF_2$ anions. In certain embodiments, between approximately 5 and 100 mg of anion exchange media is used. In certain embodiments, between approximately 10 and 50 mg of anion exchange media is used. In certain embodiments, approximately 30 mg of anion exchange media is used. In certain embodiments, between approximately 2 and 20 micromoles of a compound of Formula (II) is used. In certain embodiments, between approximately 5 and 10 micromoles of a compound of Formula (II) is used. In certain embodiments, approximately 8 micromoles of a compound of Formula (II) is used. In certain embodiments, the compound of Formula (II) is passed over anion exchange medium or through a column containing anion exchange medium using between 0.1 and 10 ml of solvent. In certain embodiments, the compound of Formula (II) is passed over anion exchange medium or through a column containing anion exchange medium using between 0.2 and 1 ml of solvent. In certain embodiments, the compound of Formula (II) is passed over anion exchange medium or through a column containing anion exchange medium using about 5 ml of solvent.

An another aspect, the present invention is directed to a method of producing a compound of Formula (I), the method comprising reacting a compound of Formula (I-e):

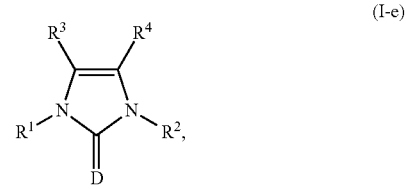

(I-e)

wherein

D is oxygen or sulfur;

$R^1$ and $R^2$ are independently selected from group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is optionally substituted with 0 to 5 occurrences of $R^5$;

$R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7_2$, and —$SR^7$;

$R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring;

$R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7_2$, and —$SR^7$;

v is 0-3;

m is 1-5;

with a Brønsted acid, a Lewis acid, or an acid anhydride to produce the compound of Formula (I).

In certain embodiments, $R^3$ of compounds of Formula (I), (I-a), (I-b), (II), (II-a), (II-b), (III), (III-a), (III-b), (IV), (IV-a), (IV-b), (V), (V-a), (V-b), (VI), (VI-a), or (VI-b) is hydrogen. In certain embodiments, $R^4$ of compounds of Formula (I), (I-a), (I-b), (II), (II-a), (II-b), (III), (III-a), (III-b), (IV), (IV-a), (IV-b), (V), (V-a), (V-b), (VI), (VI-a), or (VI-b) is hydrogen. In certain embodiments, both $R^3$ and $R^4$ of compounds of Formula (I), (I-a), (I-b), (II), (II-a), (II-b), (III), (III-a), (III-b), (IV), (IV-a), (IV-b), (V), (V-a), (V-b), (VI), (VI-a), or (VI-b) are hydrogen.

In compounds of Formula (I), (I-a), (I-b), (II), (II-a), (II-b), (III), (III-a), (III-b), (IV), (IV-a), (IV-b), (V), (V-a), (V-b), (VI), (VI-a), or (VI-b), $R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2NR^7_2$, and —$SR^7$. In certain embodiments, $R^3$ is hydrogen. In certain embodiments, $R^3$ is $C_6$ alkyl. In certain embodiments, $R^3$ is $C_{2-6}$ alkenyl. In certain embodiments, $R^3$ is $C_{2-6}$ alkynyl. In certain embodiments, $R^3$ is nitro. In certain embodiments, $R^3$ is cyano. In certain embodiments, $R^3$ is halo. In certain embodiments, $R^3$ is $C_{1-6}$ haloalkyl. In certain embodiments, $R^3$ is $C_{1-6}$ alkoxy. In certain embodiments, $R^3$ is optionally substituted $C_{6-10}$ aryl. In certain embodiments, $R^3$ is optionally substituted $C_{6-10}$ aralkyl. In certain embodiments, $R^3$ is optionally substituted 5-10 membered heteroaryl. In certain embodiments, $R^3$ is optionally substituted 4-10 membered heterocyclyl. In certain embodiments, $R^3$ is optionally substituted 3-10 membered carbocyclyl. In certain embodiments, $R^3$ is optionally substituted 4-10 membered heterocyclylalkyl. In certain embodiments, $R^3$ is acyl. In certain embodiments, $R^3$ is —$NH_2$. In certain embodiments, $R^3$ is —$NHR^7$. In certain embodiments, $R^3$ is —$N(R^7)_2$. In certain embodiments, $R^3$ is —OH. In certain embodiments, $R^3$ is —SH. In certain embodiments, $R^3$ is —$SO_2R^7$. In certain embodiments, $R^3$ is —$SOR^7$. In certain embodiments, $R^3$ is —$SO_2NR^7_2$. In certain embodiments, $R^3$ is —$SR^7$. In certain embodiments, $R^4$ is hydrogen. In certain embodiments, $R^4$ is $C_{1-6}$ alkyl. In certain embodiments, $R^4$ is $C_{2-6}$ alkenyl. In certain embodiments, $R^4$ is $C_{2-6}$ alkynyl. In certain embodiments, $R^4$ is nitro. In certain embodiments, $R^4$ is cyano. In certain embodiments, $R^4$ is halo. In certain embodiments, $R^4$ is $C_{1-6}$ haloalkyl. In certain embodiments, $R^4$ is $C_{1-6}$ alkoxy. In certain embodiments, $R^4$ is optionally substituted $C_{6-10}$ aryl. In certain embodiments, $R^4$ is optionally substituted $C_{6-10}$ aralkyl. In certain embodiments, $R^4$ is optionally substituted 5-10 membered heteroaryl. In certain embodiments, $R^4$ is optionally substituted 4-10 membered heterocyclyl. In certain embodiments, $R^4$ is optionally substituted 3-10 membered carbocyclyl. In certain embodiments, $R^4$ is optionally substituted 4-10 membered heterocyclylalkyl. In certain embodiments, $R^4$ is acyl. In certain embodiments, $R^4$ is —$NH_2$. In certain embodiments, $R^4$ is —$NHR^7$. In certain embodiments, $R^4$ is —$N(R^7)_2$. In certain embodiments, $R^4$ is —OH. In certain embodiments, $R^4$ is —SH. In certain embodiments, $R^4$ is —$SO_2R^7$. In certain embodiments, $R^4$ is —$SOR^7$. In certain embodiments, $R^4$ is —$SO_2NR^7_2$. In certain embodiments, $R^4$ is —$SR^7$.

In compounds of Formula (I), (I-a), (II), (II-a), (III), (III-a), (IV), (IV-a), (V), (V-a), (VI), or (VI-a), $R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7_2$, and —$SR^7$. In certain embodiments, $R^5$ is halo. In certain embodiments, $R^5$ is $C_{1-6}$ alkyl. In certain embodiments, $R^5$ is $C_{2-6}$ alkenyl. In certain embodiments, $R^5$ is $C_{2-6}$ alkynyl. In certain embodiments, $R^5$ is $C_{1-6}$ haloalkyl. In certain embodiments, $R^5$ is $C_{1-6}$ alkoxy. In certain embodiments, $R^5$ is optionally substituted $C_{6-10}$ aryl. In certain embodiments, $R^5$ is optionally substituted 5-10 membered heteroaryl. In certain embodiments, $R^5$ is optionally substituted 4-10 membered heterocyclyl. In certain embodiments, $R^5$ is optionally substituted 3-10 membered carbocyclyl. In certain embodiments, $R^5$ is nitro. In certain embodiments, $R^5$ is cyano. In certain embodiments, $R^5$ is acyl. In certain embodiments, $R^5$ is —$NH_2$. In certain embodiments, $R^5$ is —$NHR^7$. In certain embodiments, $R^5$ is —OH. In certain embodiments, $R^5$ is —SH. In certain embodiments, $R^5$ is —$SO_2R^7$. In certain embodiments, $R^5$ is —$SOR^7$. In certain embodiments, $R^5$ is —$SO_2NR^7_2$. In certain embodiments, $R^5$ is —$SR^7$.

In compounds of Formula (I), (I-a), (I-b), (II), (II-a), (II-b), (III), (III-a), (III-b), (IV), (IV-a), (IV-b), (V), (V-a), (V-b), (VI), (VI-a), or (VI-b), $R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring. In certain embodiments, $R^7$ is hydrogen. In certain embodiments, $R^7$ is optionally substituted aliphatic. In certain embodiments, $R^7$ is optionally substituted carbocyclyl. In certain embodiments, $R^7$ is optionally substituted heterocyclyl. In certain embodiments, $R^7$ is optionally substituted aryl. In certain embodiments, $R^7$ is optionally substituted heteroaryl. In certain embodiments, two $R^7$ groups are taken together with their intervening atoms to form an optionally substituted heterocyclic ring.

In compounds of Formula (II-f), (VI), (VI-a), (VI-b), (VI-c), (VI-d), (VI-e), or (VI-f), each occurrence of $R^8$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-N(R^{8a})_2$, $-OR^{8a}$, $-CO_2R^{8a}$, $-SO_2R^{8a}$, $-SOR^{8a}$, $-SO_2N(R^{8a})_2$, and $-SR^{8a}$. In certain embodiments, $R^8$ is $C_{1-6}$ alkyl. In certain embodiments, $R^8$ is $C_{2-6}$ alkenyl. In certain embodiments, $R^8$ is $C_{2-6}$ alkynyl. In certain embodiments, $R^8$ is nitro. In certain embodiments, $R^8$ is cyano. In certain embodiments, $R^8$ is halo. In certain embodiments, $R^8$ is $C_{1-6}$ haloalkyl. In certain embodiments, $R^8$ is $C_{1-6}$ alkoxy. In certain embodiments, $R^8$ is optionally substituted $C_{6-10}$ aryl. In certain embodiments, $R^8$ is optionally substituted $C_{6-10}$ aralkyl. In certain embodiments, $R^8$ is optionally substituted 5-10 membered heteroaryl. In certain embodiments, $R^8$ is optionally substituted 4-10 membered heterocyclyl. In certain embodiments, $R^8$ is optionally substituted 3-10 membered carbocyclyl. In certain embodiments, $R^8$ is optionally substituted 4-10 membered heterocyclylalkyl. In certain embodiments, $R^8$ is acyl. In certain embodiments, $R^8$ is $-N(R^{8a})_2$. In certain embodiments, $R^8$ is $-NH_2$. In certain embodiments, $R^8$ is $-OR^{8a}$. In certain embodiments, $R^8$ is $-OH$. In certain embodiments, $R^8$ is $-CO_2R^{8a}$. In certain embodiments, $R^8$ is $-CO_2H$. In certain embodiments, $R^8$ is $-SO_2R^{8a}$. In certain embodiments, $R^8$ is $-SO_2H$. In certain embodiments, $R^8$ is $-SOR^{8a}$. In certain embodiments, $R^8$ is $-SOH$. In certain embodiments, $R^8$ is $-SO_2N(R^{8a})_2$. In certain embodiments, $R^8$ is $-SO_2NH_2$. In certain embodiments, $R^8$ is $-SR^{8a}$. In certain embodiments, $R^8$ is $-SH$.

In compounds of Formula (II-f), (VI), (VI-a), (VI-b), (VI-c), (VI-d), (VI-e), or (VI-f), each occurrence of $R^9$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-N(R^{9a})_2$, $-OR^{9a}$, $-CO_2R^{9a}$, $-SO_2R^{9a}$, $-SOR^{9a}$, $-SO_2N(R^{9a})_2$, and $-SR^{9a}$. In certain embodiments, $R^9$ is $C_{1-6}$ alkyl. In certain embodiments, $R^9$ is $C_{2-6}$ alkenyl. In certain embodiments, $R^9$ is $C_{2-6}$ alkynyl. In certain embodiments, $R^9$ is nitro. In certain embodiments, $R^9$ is cyano. In certain embodiments, $R^9$ is halo. In certain embodiments, $R^9$ is $C_{1-6}$ haloalkyl. In certain embodiments, $R^9$ is $C_{1-6}$ alkoxy. In certain embodiments, $R^9$ is optionally substituted $C_{6-10}$ aryl. In certain embodiments, $R^9$ is optionally substituted $C_{6-10}$ aralkyl. In certain embodiments, $R^9$ is optionally substituted 5-10 membered heteroaryl. In certain embodiments, $R^9$ is optionally substituted 4-10 membered heterocyclyl. In certain embodiments, $R^9$ is optionally substituted 3-10 membered carbocyclyl. In certain embodiments, $R^9$ is optionally substituted 4-10 membered heterocyclylalkyl. In certain embodiments, $R^9$ is acyl. In certain embodiments, $R^9$ is $-N(R^{9a})_2$. In certain embodiments, $R^9$ is $-NH_2$. In certain embodiments, $R^9$ is $-OR^{9a}$. In certain embodiments, $R^9$ is $-OH$. In certain embodiments, $R^9$ is $-CO_2R^{9a}$. In certain embodiments, $R^9$ is $-CO_2H$. In certain embodiments, $R^9$ is $-SO_2R^{9a}$. In certain embodiments, $R^9$ is $-SO_2H$. In certain embodiments, $R^9$ is $-SOR^{9a}$. In certain embodiments, $R^9$ is $-SOH$. In certain embodiments, $R^9$ is $-SO_2N(R^{9a})_2$. In certain embodiments, $R^9$ is $-SO_2NH_2$. In certain embodiments, $R^9$ is $-SR^{9a}$. In certain embodiments, $R^9$ is $-SH$.

In compounds of Formula (II-f), (VI), (VI-a), (VI-b), (VI-c), (VI-d), (VI-e), or (VI-f), p is 0, 1, 2, or 3. In certain embodiments, p is 0. In certain embodiments, p is 1. In certain embodiments, p is 2. In certain embodiments, p is 3.

In methods involving structures of Formula (I), (I-e), (II), or (VI), $R^3$ and $R^4$ are independently selected from the group consisting of hydrogen, $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-NH_2$, $-NHR^7$, $-N(R^7)_2$, $-OH$, $-SH$, $-SO_2R^7$, $-SOR^7$, $-SO_2NR^7_2$, and $-SR^7$. In certain embodiments, $R^3$ is hydrogen. In certain embodiments, $R^3$ is $C_{1-6}$ alkyl. In certain embodiments, $R^3$ is $C_{2-6}$ alkenyl. In certain embodiments, $R^3$ is $C_{2-6}$ alkynyl. In certain embodiments, $R^3$ is nitro. In certain embodiments, $R^3$ is cyano. In certain embodiments, $R^3$ is halo. In certain embodiments, $R^3$ is $C_{1-6}$ haloalkyl. In certain embodiments, $R^3$ is $C_{1-6}$ alkoxy. In certain embodiments, $R^3$ is optionally substituted $C_{6-10}$ aryl. In certain embodiments, $R^3$ is optionally substituted $C_{6-10}$ aralkyl. In certain embodiments, $R^3$ is optionally substituted 5-10 membered heteroaryl. In certain embodiments, $R^3$ is optionally substituted 4-10 membered heterocyclyl. In certain embodiments, $R^3$ is optionally substituted 3-10 membered carbocyclyl. In certain embodiments, $R^3$ is optionally substituted 4-10 membered heterocyclylalkyl. In certain embodiments, $R^3$ is acyl. In certain embodiments, $R^3$ is $-NH_2$. In certain embodiments, $R^3$ is $-NHR^7$. In certain embodiments, $R^3$ is $-N(R^7)_2$. In certain embodiments, $R^3$ is $-OH$. In certain embodiments, $R^3$ is $-SH$. In certain embodiments, $R^3$ is $-SO_2R^7$. In certain embodiments, $R^3$ is $-SOR^7$. In certain embodiments, $R^3$ is $-SO_2NR^7_2$. In certain embodiments, $R^3$ is $-SR^7$. In certain embodiments, $R^4$ is hydrogen. In certain embodiments, $R^4$ is $C_{1-6}$ alkyl. In certain embodiments, $R^4$ is $C_{2-6}$ alkenyl. In certain embodiments, $R^4$ is $C_{2-6}$ alkynyl. In certain embodiments, $R^4$ is nitro. In certain embodiments, $R^4$ is cyano. In certain embodiments, $R^4$ is halo. In certain embodiments, $R^4$ is $C_{1-6}$ haloalkyl. In certain embodiments, $R^4$ is $C_{1-6}$ alkoxy. In certain embodiments, $R^4$ is optionally substituted $C_{6-10}$ aryl. In certain embodiments, $R^4$ is optionally substituted $C_{6-10}$ aralkyl. In certain embodiments, $R^4$ is optionally substituted 5-10 membered heteroaryl. In certain embodiments, $R^4$ is optionally substituted 4-10 membered heterocyclyl. In certain embodiments, $R^4$ is optionally substituted 3-10 membered carbocyclyl. In certain embodiments, $R^4$ is optionally substituted 4-10 membered heterocyclylalkyl. In certain embodiments, $R^4$ is acyl. In certain embodiments, $R^4$ is $-NH_2$. In certain embodiments, $R^4$ is $-NHR^7$. In certain embodiments, $R^4$ is $-N(R^7)_2$. In certain embodiments, $R^4$ is $-OH$. In certain embodiments, $R^4$ is $-SH$. In certain embodiments, $R^4$ is $-SO_2R^7$. In certain embodiments, $R^4$ is $-SOR^7$. In certain embodiments, $R^4$ is $-SO_2NR^7_2$. In certain embodiments, $R^4$ is $-SR^7$.

In methods involving structures of Formula (I), (I-e), (II), or (VI), $R^5$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2NR^7_2$, and —$SR^7$. In certain embodiments, $R^5$ is halo. In certain embodiments, $R^5$ is $C_{1-6}$ alkyl. In certain embodiments, $R^5$ is $C_{2-6}$ alkenyl. In certain embodiments, $R^5$ is $C_{2-6}$ alkynyl. In certain embodiments, $R^5$ is $C_{1-6}$ haloalkyl. In certain embodiments, $R^5$ is $C_{1-6}$ alkoxy. In certain embodiments, $R^5$ is optionally substituted $C_{6-10}$ aryl. In certain embodiments, $R^5$ is optionally substituted 5-10 membered heteroaryl. In certain embodiments, $R^5$ is optionally substituted 4-10 membered heterocyclyl. In certain embodiments, $R^5$ is optionally substituted 3-10 membered carbocyclyl. In certain embodiments, $R^5$ is nitro. In certain embodiments, $R^5$ is cyano. In certain embodiments, $R^5$ is acyl. In certain embodiments, $R^5$ is —$NH_2$. In certain embodiments, $R^5$ is —$NHR^7$. In certain embodiments, $R^5$ is —OH. In certain embodiments, $R^5$ is —SH. In certain embodiments, $R^5$ is —$SO_2R^7$. In certain embodiments, $R^5$ is —$SOR^7$. In certain embodiments, $R^5$ is —$SO_2NR^7_2$. In certain embodiments, $R^5$ is —$SR^7$.

In methods involving structures of Formula (I), (I-e), (II), or (VI), $R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring. In certain embodiments, $R^7$ is hydrogen. In certain embodiments, $R^7$ is optionally substituted aliphatic. In certain embodiments, $R^7$ is optionally substituted carbocyclyl. In certain embodiments, $R^7$ is optionally substituted heterocyclyl. In certain embodiments, $R^7$ is optionally substituted aryl. In certain embodiments, $R^7$ is optionally substituted heteroaryl. In certain embodiments, two $R^7$ groups are taken together with their intervening atoms to form an optionally substituted heterocyclic ring.

In methods involving a compound of Formula (VI), each occurrence of $R^8$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$N(R^{8a})_2$, —$OR^{8a}$, —$CO_2R^{8a}$, —$SO_2R^{8a}$, —$SOR^{8a}$, —$SO_2N(R^{8a})_2$, and —$SR^{8a}$. In certain embodiments, $R^8$ is $C_{1-6}$ alkyl. In certain embodiments, $R^8$ is $C_{2-6}$ alkenyl. In certain embodiments, $R^8$ is $C_{2-6}$ alkynyl. In certain embodiments, $R^8$ is nitro. In certain embodiments, $R^8$ is cyano. In certain embodiments, $R^8$ is halo. In certain embodiments, $R^8$ is $C_{1-6}$ haloalkyl. In certain embodiments, $R^8$ is $C_{1-6}$ alkoxy. In certain embodiments, $R^8$ is optionally substituted $C_{6-10}$ aryl. In certain embodiments, $R^8$ is optionally substituted $C_{6-10}$ aralkyl. In certain embodiments, $R^8$ is optionally substituted 5-10 membered heteroaryl. In certain embodiments, $R^8$ is optionally substituted 4-10 membered heterocyclyl. In certain embodiments, $R^8$ is optionally substituted 3-10 membered carbocyclyl. In certain embodiments, $R^8$ is optionally substituted 4-10 membered heterocyclylalkyl. In certain embodiments, $R^8$ is acyl. In certain embodiments, $R^8$ is —$N(R^{8a})_2$. In certain embodiments, $R^8$ is —$NH_2$. In certain embodiments, $R^8$ is —$OR^{8a}$. In certain embodiments, $R^8$ is —OH. In certain embodiments, $R^8$ is —$CO_2R^{8a}$. In certain embodiments, $R^8$ is —$CO_2H$. In certain embodiments, $R^8$ is —$SO_2R^{8a}$. In certain embodiments, $R^8$ is —$SO_2H$. In certain embodiments, $R^8$ is —$SOR^{8a}$. In certain embodiments, $R^8$ is —SOH. In certain embodiments, $R^8$ is —$SO_2N(R^{8a})_2$. In certain embodiments, $R^8$ is —$SO_2NH_2$. In certain embodiments, $R^8$ is —$SR^{8a}$. In certain embodiments, $R^8$ is —SH.

In methods involving a compound of Formula (VI), each occurrence of $R^9$ is independently selected from the group consisting of $C_{1-6}$ alkyl, $C_{2-6}$ alkenyl, $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$N(R^{9a})_2$, —$OR^{9a}$, —$CO_2R^{9a}$, —$SO_2R^{9a}$, —$SOR^{9a}$, —$SO_2N(R^{9a})_2$, and —$SR^{9a}$. In certain embodiments, $R^9$ is $C_{1-6}$ alkyl. In certain embodiments, $R^9$ is $C_{2-6}$ alkenyl. In certain embodiments, $R^9$ is $C_{2-6}$ alkynyl. In certain embodiments, $R^9$ is nitro. In certain embodiments, $R^9$ is cyano. In certain embodiments, $R^9$ is halo. In certain embodiments, $R^9$ is $C_{1-6}$ haloalkyl. In certain embodiments, $R^9$ is $C_{1-6}$ alkoxy. In certain embodiments, $R^9$ is optionally substituted $C_{6-10}$ aryl. In certain embodiments, $R^9$ is optionally substituted $C_{6-10}$ aralkyl. In certain embodiments, $R^9$ is optionally substituted 5-10 membered heteroaryl. In certain embodiments, $R^9$ is optionally substituted 4-10 membered heterocyclyl. In certain embodiments, $R^9$ is optionally substituted 3-10 membered carbocyclyl. In certain embodiments, $R^9$ is optionally substituted 4-10 membered heterocyclylalkyl. In certain embodiments, $R^9$ is acyl. In certain embodiments, $R^9$ is —$N(R^{9a})_2$. In certain embodiments, $R^9$ is —$NH_2$. In certain embodiments, $R^9$ is —$OR^{9a}$. In certain embodiments, $R^9$ is —OH. In certain embodiments, $R^9$ is —$CO_2R^{9a}$. In certain embodiments, $R^9$ is —$CO_2H$. In certain embodiments, $R^9$ is —$SO_2R^{9a}$. In certain embodiments, $R^9$ is —$SO_2H$. In certain embodiments, $R^9$ is —$SOR^{9a}$. In certain embodiments, $R^9$ is —SOH. In certain embodiments, $R^9$ is —$SO_2N(R^{9a})_2$. In certain embodiments, $R^9$ is —$SO_2NH_2$. In certain embodiments, $R^9$ is —$SR^{9a}$. In certain embodiments, $R^9$ is —SH.

In methods involving a compound of Formula (VI), p is 0, 1, 2, or 3. In certain embodiments, p is 0. In certain embodiments, p is 1. In certain embodiments, p is 2. In certain embodiments, p is 3.

In certain embodiments, the method further comprises reacting the compound of Formula (I) or Formula (VI) with a hydroxyl group-containing organic substrate or a tautomer thereof under conditions sufficient to fluorinate the organic compound, thereby providing a fluorinated organic compound. In certain embodiments, the fluorinated organic compound comprises $^{18}F$ or $^{19}F$.

In another aspect, the present invention is directed to a reaction mixture comprising a compound of Formula (I), (II), (III), (IV), (V), or (VI) and a fluorine source. In certain embodiments, the reaction mixture comprises a compound of Formula (I-e), an acid, a base, an organic compound and a fluorine source.

In another aspect, the present invention is directed to a kit comprising a compound of Formula (I), (II), (III), (IV), (V), (VI), or (I-e) and a container. In certain embodiments, the kit further comprises instructions for use of the compound of Formula (I), (II), (III), (IV), (V), (VI), or (I-e). In certain embodiments, the kit further comprises a base and a fluorine source.

Organic Compounds

Compounds (e.g., a compound of Formula (I), (II), or (VI)) useful in a method of fluorinating a hydroxyl group-containing organic compound or substrate or tautomer thereof are described herein. A hydroxyl group-containing organic compound or substrate or tautomer thereof is represented herein as

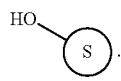

Following reaction with the hydroxyl group, the hydroxyl group-containing organic compound or substrate or tautomer thereof is represented herein as

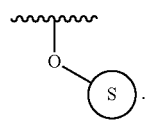

An organic compound or substrate is an organic molecule of any molecular weight. In certain embodiments, the molecule is a small organic molecule. In certain embodiments, the small organic molecule includes any molecule having a molecular weight of less than 2000 g/mol. In certain embodiments, the small organic molecule includes any molecule having a molecular weight of less than 1900 g/mol. In certain embodiments, the small organic molecule includes any molecule having a molecular weight of less than 1800 g/mol. In certain embodiments, the small organic molecule includes any molecule having a molecular weight of less than 1700 g/mol. In certain embodiments, the small organic molecule includes any molecule having a molecular weight of less than 1600 g/mol. In certain embodiments, the small organic molecule includes any molecule having a molecular weight of less than 1500 g/mol. In certain embodiments, the small organic molecule includes any molecule having a molecular weight of less than 1400 g/mol. In certain embodiments, the small organic molecule includes any molecule having a molecular weight of less than 1300 g/mol. In certain embodiments, the small organic molecule includes any molecule having a molecular weight of less than 1200 g/mol. In certain embodiments, the small organic molecule includes any molecule having a molecular weight of less than 1100 g/mol. In certain embodiments, the small organic molecule includes any molecule having a molecular weight of less than 1000 g/mol. In certain embodiments, the small organic molecule includes any molecule having a molecular weight of less than 900 g/mol. In certain embodiments, the small organic molecule includes any molecule having a molecular weight of less than 800 g/mol. In certain embodiments, the small organic molecule includes any molecule having a molecular weight of less than 700 g/mol. In certain embodiments, the small organic molecule includes any molecule having a molecular weight of less than 600 g/mol. In certain embodiments, the small organic molecule includes any molecule having a molecular weight of less than 500 g/mol. In certain embodiments, the small organic molecule includes any molecule having a molecular weight of less than 400 g/mol. In certain embodiments, the small organic molecule includes any molecule having a molecular weight of less than 300 g/mol. In certain embodiments, the small organic molecule includes any molecule having a molecular weight of less than 200 g/mol. In certain embodiments, the small organic molecule includes any molecule having a molecular weight of less than 100 g/mol. In certain embodiments, the molecule is a large organic molecule. In certain embodiments, the large organic molecule is between 1000 g/mol to 5000 g/mol. In certain embodiments, the large organic molecule is between 1000 g/mol to 3000 g/mol. In certain embodiments, the large organic molecule is between 1000 g/mol to 2000 g/mol. In certain embodiments, the large organic molecule is between 1000 g/mol to 1500 g/mol. Organic compounds include aliphatic, alkyl, alkenyl, carbocyclic, aryl, heteroaryl and heterocyclyl containing compounds containing a wide variety of substitutents. In certain embodiments, the hydroxyl-group containing organic compound is (S)-2-amino-3-(3,4-dihydroxyphenyl)propanoic acid (L-DOPA), (R)-2-amino-3-(3,4-dihydroxyphenyl)propanoic acid (D-DOPA), or a mixture thereof. In certain embodiments, the hydroxyl-group containing organic compound is a protected L-DOPA, D-DOPA, or a mixture thereof. In certain embodiments, the hydroxyl-group containing organic compound is L-DOPA, D-DOPA, or a mixture thereof wherein one of the hydroxyl groups are protected with an oxygen protecting group. In certain embodiments, the hydroxyl-group containing organic compound is L-DOPA, D-DOPA, or a mixture thereof wherein both of the hydroxyl groups are protected with an oxygen protecting group. In certain embodiments, the hydroxyl-group containing organic compound is L-DOPA, D-DOPA, or a mixture thereof wherein the amine group is protected with a nitrogen protecting group.

In certain embodiments, the organic compound contains a chiral center. In certain embodiments, the organic compound is further substituted with one or more functional groups (e.g., alcohols, aldehydes, ketones, esters, alkenes, alkoxy groups, cyano groups, amines, amides, and N-oxides). In certain embodiments, the functional groups are unprotected. In certain embodiments, the organic compound is a precursor of a pharmaceutical agent.

Fluorine or Fluoride Sources

The methods described herein generally involve a fluorine source. The terms "fluorine source" and "fluoride source" are used interchangeably herein. In certain embodiments, the fluorine source is a nucleophilic fluorine source (e.g., a fluoride, F). In certain embodiments, the fluorine source is commercially available. In certain embodiments, the fluorine source is also an inorganic fluorine source. Exemplary fluorine sources include sodium fluoride (NaF), cesium fluoride (CsF), potassium fluoride (KF), ammonium fluoride ($NH_4F$), calcium fluoride ($CaF_2$), lithium fluoride (LiF), aluminum fluoride ($AlF_3$), barium fluoride ($BaF_2$), silver fluoride (AgF and $AgF_2$), tetramethylammonium fluoride ($Me_4NF$), magnesium fluoride ($MgF_2$), zinc fluoride ($ZnF_2$), copper fluoride (CuF and $CuF_2$), TBAF ($^nBu_4NF$), cerium fluoride ($CeF_3$), tin fluoride ($SnF_2$), scandium fluoride ($ScF_3$), and indium fluoride ($InF_3$). In certain embodiments, the fluorine source is the counter ion Q.

The fluorine source may be enriched with a particular isotope of fluorine. In certain embodiments, the fluorine source is labeled with $^{19}F$. In certain embodiments, use of a $^{19}F$-labeled fluorine source in the inventive method provides a fluorinated $^{19}F$-labeled organic compound.

In certain embodiments, the fluorine source is labeled with $^{18}F$ (i.e., provides a $^{18}F$ fluorine to the reaction mixture). In certain embodiments, use of a $^{18}F$-labeled fluorine source in the inventive method provides a fluorinated $^{18}F$-labeled organic compound.

However, in certain embodiments, the fluorine source is labeled with a mixture of $^{18}F$ and $^{19}F$. In certain embodiments, use of a mixture of $^{19}F$ and $^{18}F$ fluorine sources in the inventive method provides a mixture of fluorinated $^{19}$F-labeled organic compound and fluorinated $^{18}$F-labeled organic compound.

Reaction Conditions

Described herein are methods of producing a fluorinating reagent and methods of fluorinating hydroxyl group-containing organic compounds (e.g., a phenol, hydroxypyridine, etc.) or tautomers thereof (e.g., pyridone) using a fluorinating agent (e.g., a compound of Formula (I)). In certain embodiments, the reaction further comprises a solvent. Exemplary solvents include non-polar solvents (e.g., toluene, dioxane, or benzene). In certain embodiments, the reaction is performed under ambient temperature, pressure and atmosphere. In certain embodiments, the reaction is performed in an inert atmosphere (e.g., an atmosphere that is substantially free of dioxygen or water). In certain embodiments, the reaction is performed under anhydrous conditions (e.g., in a solvent that is substantially free of water). In certain embodiments, the reaction is heated. In certain embodiments, the reaction is heated to about 110° C. In certain embodiments, the reaction is cooled. In certain embodiments, the reaction is performed at room temperature (e.g., about 20-25° C.).

In certain embodiments, the reaction proceeds in a single step. In a one-step procedure, an organic compound comprising a substrate and a fluorine source, and optionally an additional reagent such as a base (e.g., NaOH, KOH, BaO, MgO, NaHCO$_3$, KHCO$_3$, Na$_2$CO$_3$, Ba(OH)$_2$, 2,6-lutidine, or K$_2$CO$_3$) or a salt (e.g., cesium fluoride), to yield a fluorinated organic compound.

In certain embodiments, the reaction proceeds in two steps. In a two-step procedure, the organic compound comprising substrate may be first reacted with a compound of Formula (I) in the presence of an optional additional reagent, such as a base (e.g., NaOH, KOH, BaO, MgO, NaHCO$_3$, KHCO$_3$, Na$_2$CO$_3$, Ba(OH)$_2$, 2,6-lutidine, or K$_2$CO$_3$). In certain embodiments, an intermediate product of Formula (II), Formula (III), Formula (IV), or Formula (V) is isolated from the first reaction. The intermediate product may be further reacted with a fluorinating agent in the second step. In these embodiments, isolation enables the investigator to evaluate numerous reaction conditions for subsequent fluorination. In certain embodiments, each step further comprises a solvent, and the solvents may be the same or may be different. For example, the first step may take place in acetonitrile, while the second step may take place in acetone. In certain embodiments, each step is performed at a different temperature. For example, the first step may involve cooling (e.g., the reaction mixture at 0° C.), while the second step may be performed at ambient temperature.

In certain embodiments, a compound of the present invention, a compound of the methods described herein, or the hydroxyl group-containing organic molecule is immobilized on a solid support. In certain embodiments, a compound of Formula (I) is immobilized on a solid support. In certain embodiments, a compound of Formula (I-a) is immobilized on a solid support. In certain embodiments, a compound of Formula (I-b) is immobilized on a solid support. In certain embodiments, a compound of Formula (I-c) is immobilized on a solid support. In certain embodiments, a compound of Formula (I-d) is immobilized on a solid support. In certain embodiments, a compound of Formula (I-e) is immobilized on a solid support. In certain embodiments, a compound of Formula (II) is immobilized on a solid support. In certain embodiments, a compound of Formula (II-a) is immobilized on a solid support. In certain embodiments, a compound of Formula (II-b) is immobilized on a solid support. In certain embodiments, a compound of Formula (II-c) is immobilized on a solid support. In certain embodiments, a compound of Formula (II-d) is immobilized on a solid support. In certain embodiments, a compound of Formula (II-e) is immobilized on a solid support. In certain embodiments, a compound of Formula (II-f) is immobilized on a solid support. In certain embodiments, a compound of Formula (III) is immobilized on a solid support. In certain embodiments, a compound of Formula (III-a) is immobilized on a solid support. In certain embodiments, a compound of Formula (III-b) is immobilized on a solid support. In certain embodiments, a compound of Formula (III-c) is immobilized on a solid support. In certain embodiments, a compound of Formula (IV) is immobilized on a solid support. In certain embodiments, a compound of Formula (IV-a) is immobilized on a solid support. In certain embodiments, a compound of Formula (IV-b) is immobilized on a solid support. In certain embodiments, a compound of Formula (IV-c) is immobilized on a solid support. In certain embodiments, a compound of Formula (V) is immobilized on a solid support. In certain embodiments, a compound of Formula (V-a) is immobilized on a solid support. In certain embodiments, a compound of Formula (V-b) is immobilized on a solid support. In certain embodiments, a compound of Formula (V-c) is immobilized on a solid support. In certain embodiments, a compound of Formula (VI) is immobilized on a solid support. In certain embodiments, a compound of Formula (VI-a) is immobilized on a solid support. In certain embodiments, a compound of Formula (VI-b) is immobilized on a solid support. In certain embodiments, a compound of Formula (VI-c) is immobilized on a solid support. In certain embodiments, a compound of Formula (VI-d) is immobilized on a solid support. In certain embodiments, a compound of Formula (VI-e) is immobilized on a solid support. In certain embodiments, a compound of Formula (VI-f) is immobilized on a solid support.

In certain embodiments, the fluorination takes place at a late stage in the synthesis of a fluorinated organic compound. In certain embodiments, the fluorination is the last step in the synthesis of the fluorinated organic compound. In certain embodiments, fluorination at the last step in the synthesis of the fluorinated organic compound comprises preparation of a PET probe.

In certain embodiments, subsequent to the reaction, the fluorinated organic compound is purified from the reaction mixture. In certain embodiments, the fluorinated organic compound is purified by column chromatography on silica gel. In certain embodiments, the fluorinated organic compound is purified by preparative thin-layer chromatography. In certain embodiments, the fluorinated organic compound is purified by reverse or normal phase HPLC. Methods of purification via these techniques are described in Snyder, *Introduction to Modern Liquid Chromatography* (John Wiley & Sons, NJ, 2010) and McMaster, *HPLC: A Practical User's Guide* (John Wiley & Sons, NJ, 2007).

Reaction Products

Described herein are methods of making fluorinated organic compounds. In certain embodiments, the fluorinated organic compounds are generated from their corresponding precursors in yields of at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100%.

In certain embodiments, described herein are methods of fluorinating organic compounds with $^{18}$F. In certain embodiments, the $^{18}$F-labeled organic compounds are generated from their corresponding precursors in radiochemical yields of at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100%.

The reaction conditions described herein are tolerant of many functional groups as well as chiral centers. In certain embodiments, the fluorinated organic compound is further substituted by one or more functional groups, such as aldehydes, ketones, esters, alkenes, alkoxy groups, cyano groups, amines, amides and N-oxides. In certain embodiments, the fluorinated organic compound contains a chiral center that is derived from the starting material. The stereochemistry at the chiral center may remain substantially unchanged (e.g., little to no racemization or epimerization of the chiral center occurs during the reaction). In the case of chiral aliphatic hydroxyls, the stereochemistry at the chiral center may be inverted. In certain embodiments, inversion is stereospecific. In certain embodiments, enantiomeric purity may fall by less than 5%. In certain embodiments, enantiomeric purity may fall by 5-10%. In certain embodiments, enantiomeric purity may fall by 10-20%. In certain embodiments, enantiomeric purity may fall by 20-30%.

In certain embodiments, the fluorinated organic compound is $^{19}$F labeled. In certain embodiments, the labeled organic compound is an imaging agent, such as an MRI imaging agents. In certain embodiments, the labeled organic compound may be used as a probe, such as a biological NMR probes for use in in vivo NMR spectroscopy.

In certain embodiments, the fluorinated organic compound is $^{18}$F labeled. In certain embodiments, the $^{18}$F-labeled organic compound is an imaging agent, such as a PET imaging agent.

In certain embodiments, the fluorinated organic compound is a compound having biological activity. In certain embodiments, the fluorinated organic compound is a compound with pharmacologic activity (i.e., binds to a receptor or enzyme). Exemplary fluorinated organic compounds include fluoro-estrone, fluoro-menthol, fluoro-cholesterol, and fluoro-testosterone. In certain embodiments, the fluorinated organic compound is described in previous applications by the inventors PCT/US2009/065339, published as WO 10/059943, PCT/US2010/020540, published as WO 10/081034, PCT/US2010/020544, published as WO/081036, PCT/US2010/041561, published as WO 11/006088, and U.S. application, U.S. Ser. No. 61/721,131, filed Nov. 1, 2012, and these documents are incorporated herein by reference.

Kits

The fluorination reagent used in the inventive methods described herein may be provided in a kit. The kit includes (a) the fluorination reagent useful in the inventive method described herein (e.g., a compound of Formulas (I), (II), or (VI)), and, optionally (b) informational material. The informational material can be descriptive, instructional, marketing or other material that relates to the methods described herein and/or the use of the compounds for the methods described herein.

The informational material of the kits is not limited in its form. In one embodiment, the informational material can include information about production of the fluorination reagent, molecular weight of the fluorination reagent, concentration, date of expiration, batch or production site information, and so forth. In one embodiment, the informational material relates to methods for using the fluorination reagent.

In certain embodiments, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a fluorination reagent described herein and/or its use in the methods described herein. Of course, the informational material can also be provided in any combination of formats.

In certain embodiments, the components of the kit are stored under inert conditions (e.g., under nitrogen or another inert gas such as argon). In certain embodiments, the components of the kit are stored under anhydrous conditions (e.g., with a desiccant). In certain embodiments, the components are stored in a light blocking container such as an amber vial.

The fluorination reagent described herein can be provided in any form, e.g., liquid, dried, or lyophilized form. It is preferred that the fluorination reagent described herein be substantially pure and/or sterile. When the fluorination reagent described herein is provided as a dried form, reconstitution generally is by the addition of a suitable solvent.

The kit can include one or more containers for the composition containing the fluorination reagent described herein. In certain embodiments, the kit contains separate containers, dividers or compartments for the composition and informational material. For example, the composition can be contained in a bottle, vial, or ampule, and the informational material can be contained in a plastic sleeve or packet. In other embodiments, the separate elements of the kit are contained within a single, undivided container. For example, the composition is contained in a bottle, vial or ampule that has attached thereto the informational material in the form of a label. The containers of the kits can be air tight, waterproof (e.g., impermeable to changes in moisture or evaporation), and/or light-tight.

Current reagents of Formula (I), (II), or (VI) will enable the automation of all transformations described above. The described methods are readily adaptable to the most widely available automated equipment. This will enable broad application to PET facilities throughout the community without infrastructure investments. In certain embodiments, $^{18}$F labeling with the inventive method is carried out in line with an robotic reagent dispensing and weighing system such as a Tecan MCA96. In certain embodiments, $^{18}$F labeling with the inventive method is performed in a parallel reactor system such as a Mettler Bohdan Miniblock. In certain embodiments, $^{18}$F labeling with the inventive method is performed in line with an automatic purification and analytical system such as a Waters AutoPurification HPLC/MS.

EXAMPLES

Materials and Methods

Solvents other than methanol were dried by passage through alumina. Except as indicated otherwise, reactions were magnetically stirred and monitored by thin layer chromatography (TLC) using EMD TLC plates pre-coated with 250 μm thickness silica gel 60 F254 plates and visualized by fluorescence quenching under UV light. In addition, TLC plates were stained using ceric ammonium molybdate or potassium permanganate stain. Flash chromatography was performed on Dynamic Adsorbents Silica Gel 40-63 μm particle size or Whatman Silica Gel 60 μm particle size using a forced flow of eluent at 0.3-0.5 bar pressure. Concentration under reduced pressure was performed by rotary evaporation at 25-30° C. at appropriate pressure. Purified compounds were further dried under high vacuum (0.01-0.05 Torr). NMR spectra were recorded on a Varian Mercury 400 (400 MHz for $^1$H, 100 MHz for $^{13}$C, 375 MHz for $^{19}$F, and 126 MHz for $^{31}$P acquisitions), Unity/Inova 500 (500 MHz for $^1$H, 125 MHz for $^{13}$C acquisitions), or Unity/Inova 600 (600 MHz for $^1$H acquisitions) spectrometer. $^{13}$C NMR spectra are recorded 1H decoupled. $^{19}$F NMR spectra are recorded 1H coupled. Chemical shifts are reported in ppm with the solvent resonance as the internal standard. Data is reported as follows: s=singlet, d=doublet, t=triplet, q=quartet, h=heptet, m=multiplet, br=broad; coupling constants in Hz; integration. High-resolution mass spectra were obtained on Jeol AX-505 or SX-102 spectrometers at the Harvard University Mass Spectrometry Facilities. Sodium hydroxide was purchased from Mallinckrodt Chemicals, Molecular sieves 3 Å were purchased from EMD Chemicals and finely grinded and dried at 130° C. overnight prior to use. NMR spectroscopic data of known compounds correspond to the data given in the appropriate references. Pyridine and triethylamine were distilled over calcium hydride. NMR spectroscopic data of known compounds correspond to the data given in the appropriate references.

Example 1. Preparation of I-c

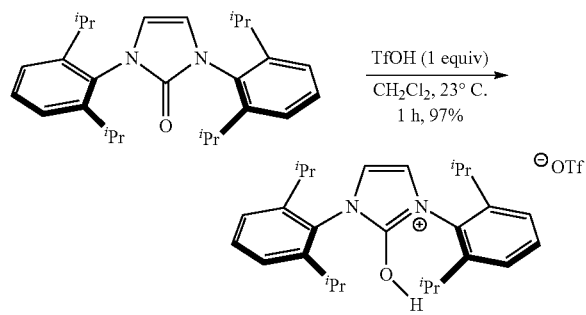

To 1,3-bis(2,6-diisopropylphenyl)-1,3-dihydro-2H-imidazol-2-one (2.00 g, 4.93 mmol, 1.00 equiv) in dichloromethane (10 mL) at 23° C. was added triflic acid (435 µL, 4.93 mmol, 1.00 equiv). The reaction mixture was stirred for 1 hour before 50 ml hexanes were added to afford a white precipitate. The solids were collected by filtration and washed with hexanes (10 mL) and then dried under vacuum to afford 2.68 g of the title compound as a white solid (97% yield). X-ray quality crystals were grown by storing a concentrated solution of (I-c) in CDCl$_3$ at 23° C. giving colorless crystals after 24 hours.

mp: 180° C. (decomp). NMR spectroscopy: 1H-NMR (400 MHz, CDCl$_3$, 23° C., δ): 8.22 (broad, 1H), 7.52 (t, J=7.8 Hz, 2H), 7.33 (d, J=7.8 Hz, 4H), 6.73 (s, 2H), 2.66 (sept, J=7.0 Hz, 4H), 1.27 (d, J=4.3 Hz, 24H), 1.25 (d, J=3.9 Hz, 12H). 13C-NMR (125 MHz, CDCl$_3$, 23° C., δ): 149.0, 145.8, 131.4, 127.9, 124.9, 124.4, 117.5, 28.9, 23.5, 23.2. 19F-NMR (375 MHz, CDCl$_3$, 23° C., δ): −74.4 (s). FT-IR Spectroscopy (solid, cm−1): 3453, 2963, 2931, 2871, 1676, 1622, 1515, 1458, 1302, 1175. Anal: calcd for C28H37F3N2O4S: C, 60.63; H, 6.72; N, 5.05; F, 10.28. found: C, 60.60; H, 6.56; N, 5.01; F, 9.92.

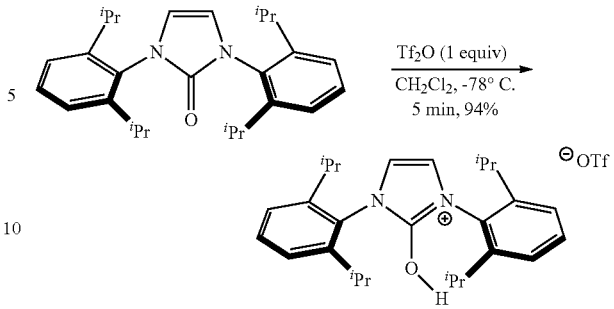

To 1,3-bis(2,6-diisopropylphenyl)-1,3-dihydro-2H-imidazol-2-one (10.0 g, 24.7 mmol, 1.00 equiv) in dichloromethane (35 mL) at −78° C. was added triflic anhydride (4.2 mL, 24.7 mmol, 1.00 equiv). The reaction mixture was stirred for 5 min before 200 ml hexanes were added to afford a white precipitate. The solids were collected by filtration and washed with hexanes (20 mL) and then dried under vacuum to afford 12.8 g of the title compound as a white solid (94% yield).

Example 2. X-Ray Structure of I-c

Figure 4:
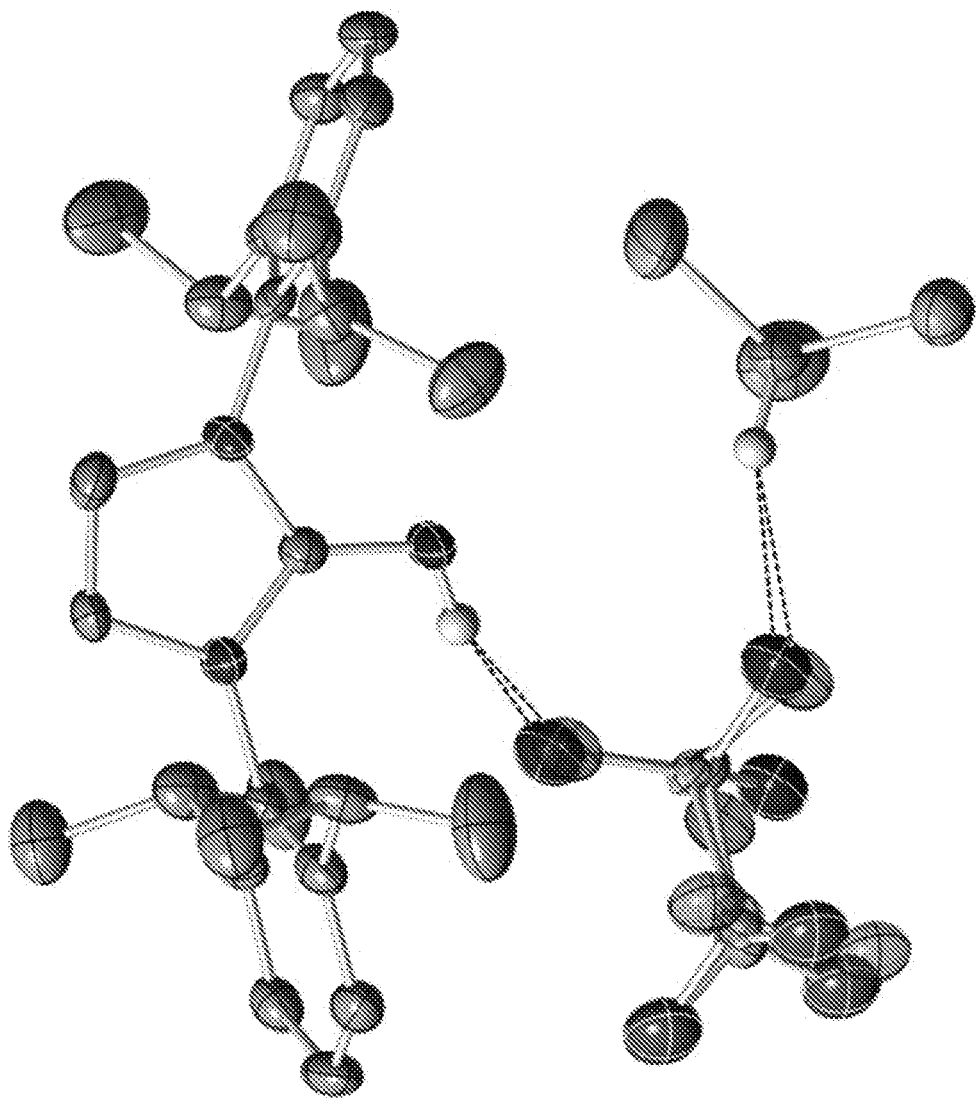
FIG. 4 shows the X-ray structure of (I-c) and a molecule of dichloromethane. Thermal ellipsoids are drawn at the 50% probability level; H atoms (except those involved in H-bonding) are omitted for clarity, and the disorder model is depicted using transparent ellipsoids.
Figure 5:
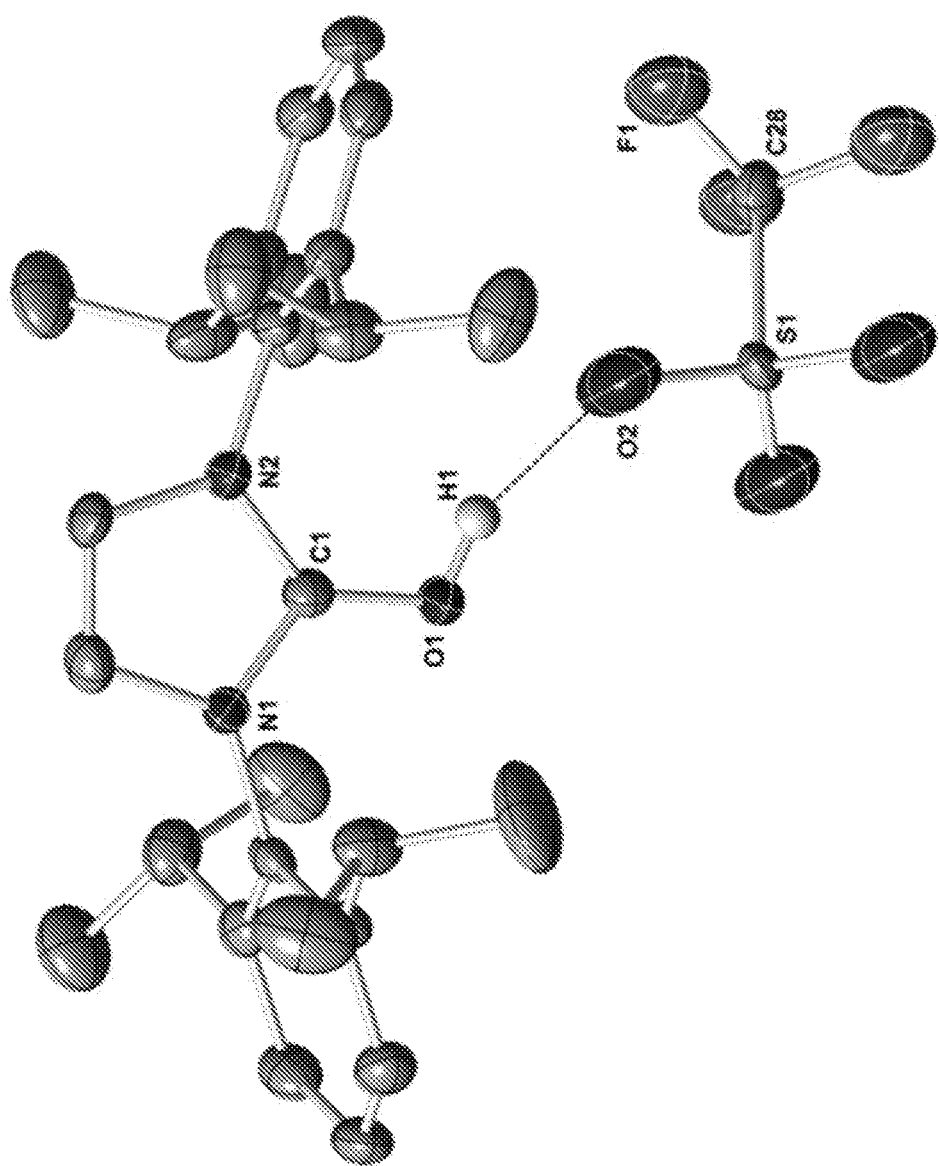
FIG. 5 shows the X-ray structure of (I-c) and a molecule of dichloromethane with selected atom labeling scheme. Thermal ellipsoids are drawn at the 50% probability level; Solvent, disorder, and H atoms (except those involved in H-bonding) are omitted for clarity.

I-c was crystallized as colorless plates by slow evaporation of a concentrated CDCl$_3$ solution. A 0.4×0.3×0.1 mm crystal was selected and mounted on a nylon loop using Paratone-N oil, and transferred to a Bruker APEX II CCD diffractometer (MoK radiation, λ=0.71073 Å) equipped with an Oxford Cryosystems nitrogen flow apparatus. The sample was held at 150 K during the data collection. The collection method involved 0.5° scans in ω at 28° in 2θ. Data integration down to 0.82 Å resolution was carried out using SAINT V7.46 A (Bruker diffractometer, 2009) with reflection spot size optimisation. Absorption corrections were made with the program SADABS (Bruker diffractometer, 2009). The structure was solved by the direct methods procedure and refined by least-squares methods against F$^2$ using SHELXS-97 and SHELXL-97 (Sheldrick, 2008). Non-hydrogen atoms were refined anisotropically, and hydrogen atoms were allowed to ride on the respective atoms. Restraints on bond lengths and constraints of the atomic displacement parameters on each pair of disorder fragments (SADI and EADP instructions of SHELXL97), as necessary, have been applied for the disorder refinement. Crystal data, details of data collection and refinement, and selected geometric parameters are given in the tables below. Graphics were produced using the CystalMaker 8.6 software program (©1994-2012 CrystalMaker Software Ltd.) (see FIGS. 4 and 5 for X-ray structure images).

Example 3. General $^{18}$F Radiolabeling Procedure with I-c

No-carrier-added [$^{18}$F]fluoride was produced from water 97% enriched in $^{18}$O (Sigma-Aldrich®) by the nuclear reaction $^{18}$O(p,n)$^{18}$F using a Siemens Eclipse HP cyclotron and a silver-bodied target at MGH Athinoula A. Martinos Center for Biomedical Imaging. The produced [$^{18}$F]fluoride in water was transferred from the cyclotron target by helium push. In the analysis of the $^{18}$F-labeled compounds, isotopically unmodified reference substances were used for identification. Radioactivity was measured in a Capintec, Inc. CRC-25PET ion chamber. *Solvents and reagents for radiochemical experiments*: Acetonitrile, extra dry, (AcroSeal®)

and dichloroethane, extra dry, (AcroSeal®) was purchased from Acros® and used as received. Water was obtained from a Millipore Milli-Q Integral Water Purification System. 18-crown-6 was sublimed. Potassium carbonate (≥99.99%) was purchased from Sigma-Aldrich® and used as received.

[$^{18}$F]Fluoride solution obtained from a cyclotron was loaded onto a Macherey-Nagel SPE Chromafix 30-PS-HCO$_3$ cartridge that had been previously washed with 2.0 mL of 5.0 mg/mL K$_2$CO$_3$ in Millipore Milli-Q water and then 20 mL of Millipore Milli-Q water. After loading, the cartridge was washed with 2 mL of Millipore Milli-Q water. [$^{18}$F]Fluoride was eluted with 0.5 mL of a 5.0 mg/mL K$_2$CO$_3$ in Millipore Milli-Q water solution. The solution was diluted with 2.0 mL of acetonitrile providing 2.5 mL of 4:1 MeCN:H$_2$O solution containing 1.0 mg/mL K$_2$CO$_3$. This solution was then put in a conical vial and 0.50 mL of a stock solution containing 18-crown-6 (13 mg/mL MeCN) was then added. The solution was evaporated at 108° C. with a constant nitrogen gas stream. At dryness, 0.5 mL of acetonitrile was added and evaporated at 108° C. with a constant nitrogen gas stream. Another 0.5 mL of acetonitrile was added and evaporated at 108° C. with a constant nitrogen gas stream to leave a white precipitate around the bottom and sides of the vial. The vial was purged with nitrogen, and sealed with a cap fitted with a septum. 0.3 mL of a solution of (I-c) (5 mg, 9.0×10$^{-3}$ mmol) and the phenol of interest (10 mg) was added and the conical vial was sonicated for 5 seconds before it was heated for 15 minutes.

After the reaction mixture was allowed to cool to 23° C., a capillary tube was used to spot the solution on a silica gel TLC plate. The TLC plate was eluted and the TLC plate was scanned with a Bioscan AR-2000 Radio TLC Imaging Scanner to determine [$^{18}$F]fluoride incorporation into the aryl fluoride product. Radiolabeled products were indentified through co-injection with an authentic standard on radio-HPLC.

Example 4. Radiolabeling of Estrone Using I-c

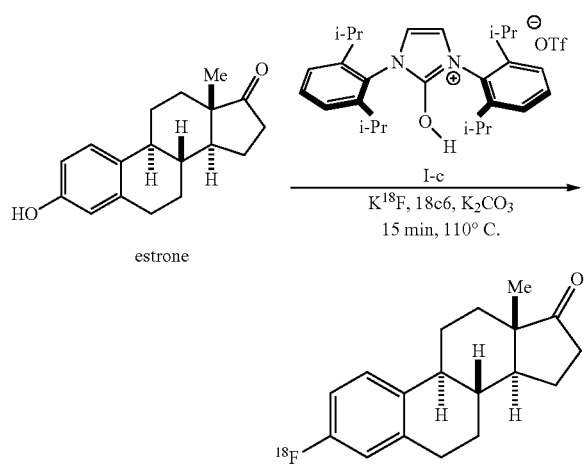

Figure 6A:
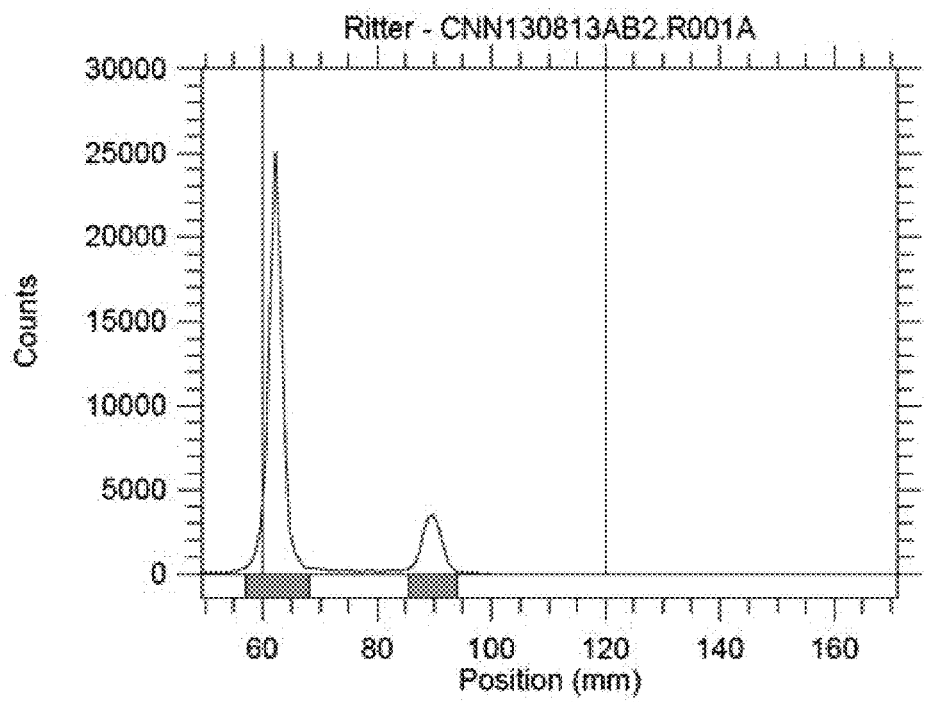
FIG. 6A shows the radio TLC scan for the isotopic labeling experiment with estrone. The position at 60 mm corresponds to the baseline of the TLC plate ($^{18}$F-fluoride), the position at 90 mm corresponds to $^{18}$F-estrone (RCY=13%).

Following azeotropic drying of $^{18}$F-fluoride (see general experimental section), 5 mg (I-c) and 10 mg estrone dissolved in dichloroethane (0.3 ml) were added and the reaction mixture was heated to 110° C. for 15 minutes. After the reaction mixture was allowed to cool to 23° C., a capillary tube was used to spot the solution on a silica gel TLC plate and was eluted with a 4:1 (v:v) hexanes:ethyl acetate (see FIG. 6A).

Example 5. Radiolabeling of Testosterone Using (I-c)

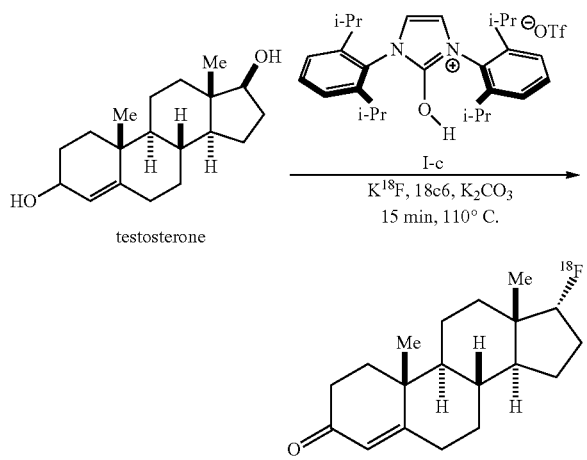

Figure 6B:
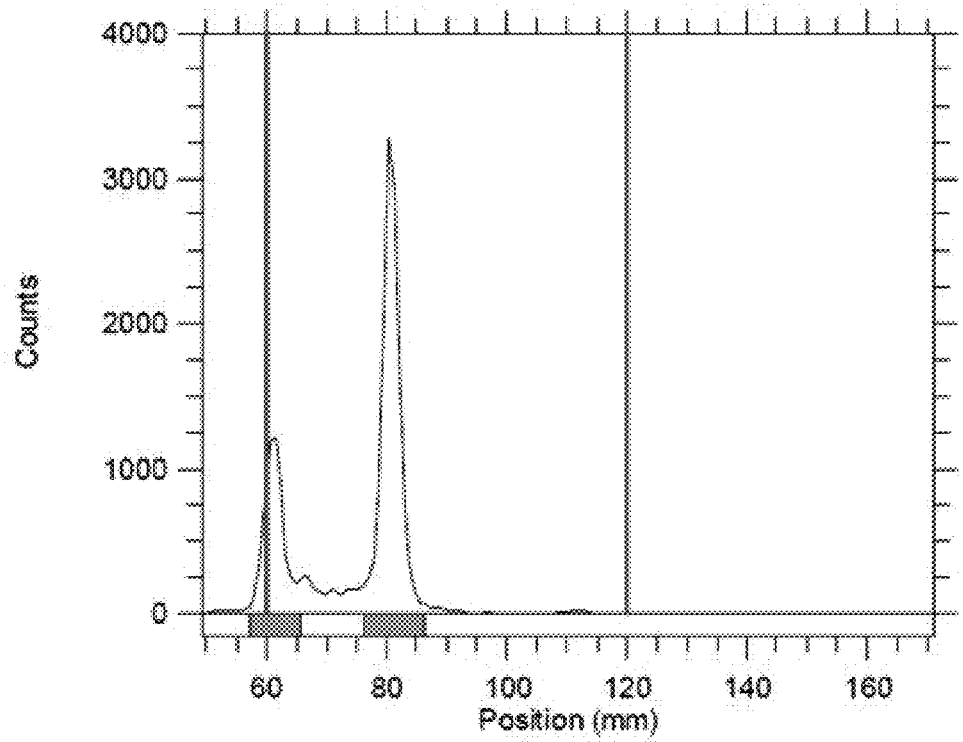
FIG. 6B shows the radio TLC scan for the isotopic labeling experiment with testosterone. The position at 60 mm corresponds to the baseline of the TLC plate ($^{18}$F-fluoride), the position at 82 mm corresponds to $^{18}$F-testosterone.

Following azeotropic drying of $^{18}$F-fluoride (see general experimental section), 5 mg (I-c) and 10 mg testosterone dissolved in dichloroethane (0.3 ml) were added and the reaction mixture was heated to 110° C. for 15 minutes. After the reaction mixture was allowed to cool to 23° C., a capillary tube was used to spot the solution on a silica gel TLC plate and was eluted with a 4:1 (v:v) hexanes:ethyl acetate (see FIG. 6B).

Example 5. Radiolabeling of Menthol Using I-c

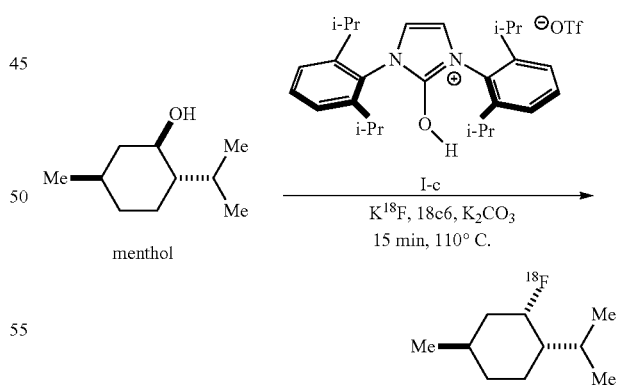

Figure 6C:
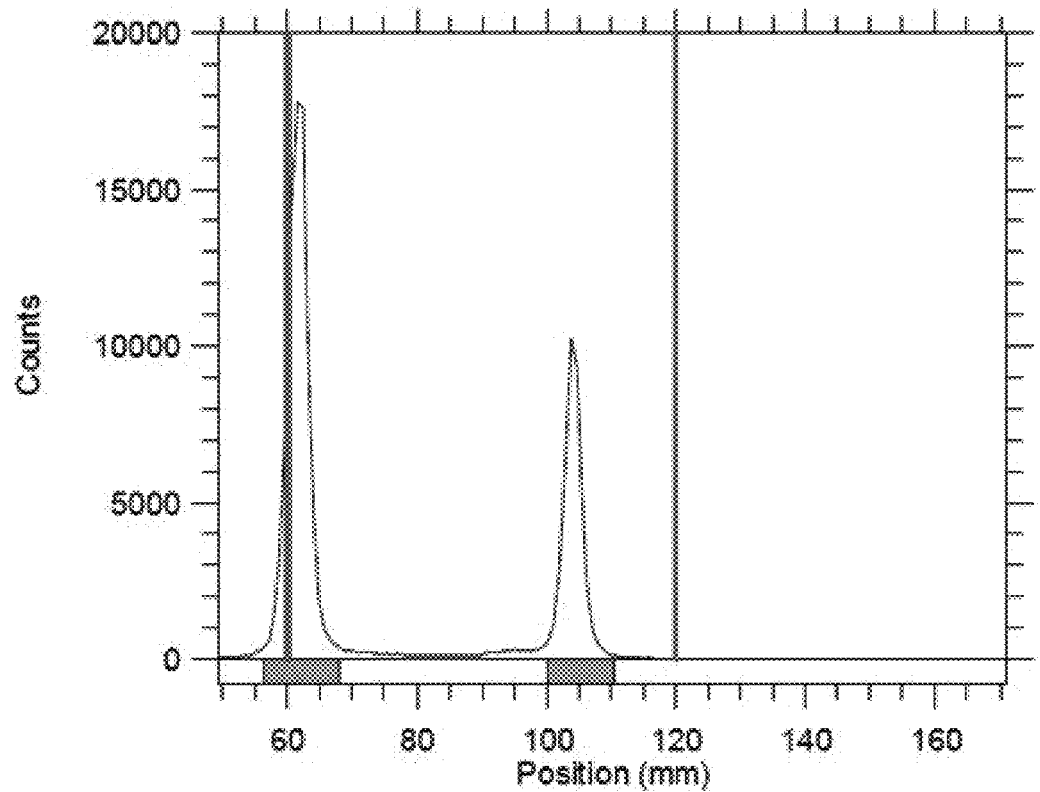
FIG. 6C shows the radio TLC scan for the isotopic labeling experiment with menthol. The position at 60 mm corresponds to the baseline of the TLC plate ($^{18}$F-Fluoride), the position at 105 mm corresponds to $^{18}$F-menthol.
Figures 7A, 7B:
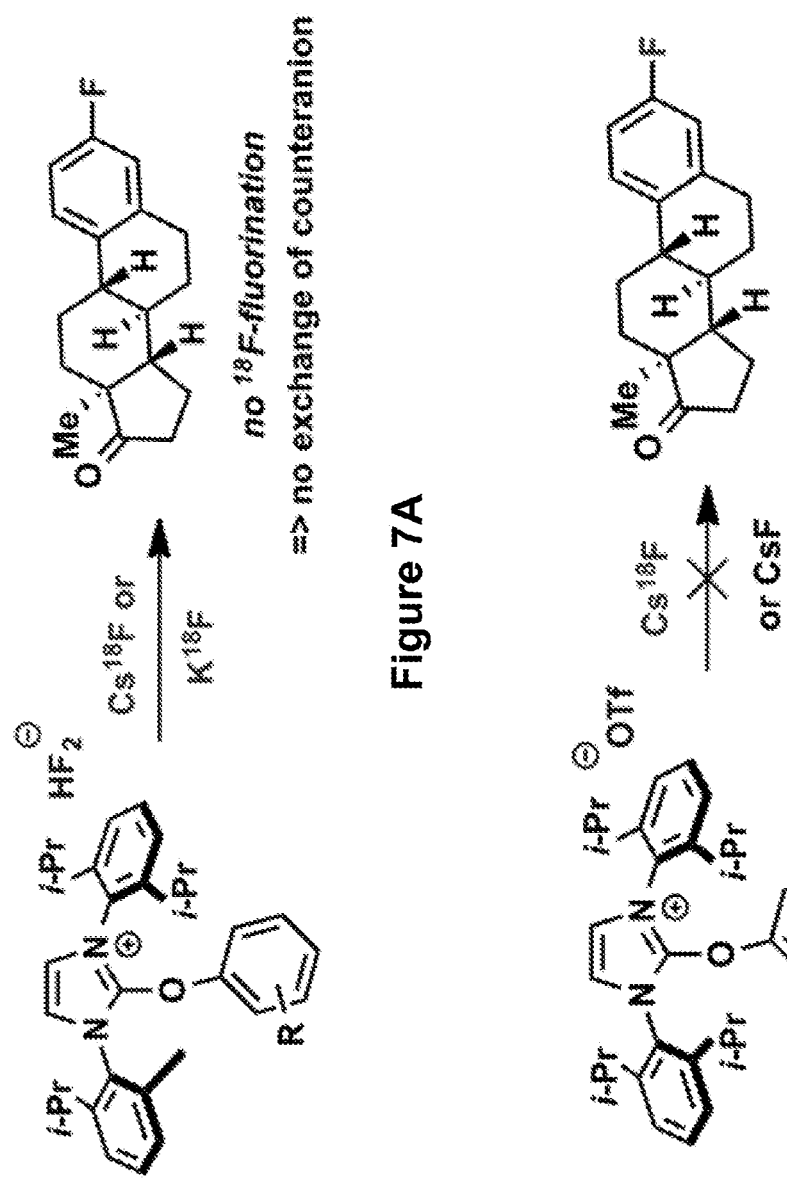
FIG. 7A shows that anion methathesis of the uronium does not occur under typical reaction conditions. Instead, extraneous fluoride converts the bifluoride counteranion to a fluoride counteranion, which proceeds attack the aromatic ring.
FIG. 7B shows that uronium triflate is unreactive in the presence of fluoride, since triflate, unlike bifluoride, cannot be converted into a fluoride counteranion.

Following azeotropic drying of $^{18}$F-fluoride (see general experimental section), 5 mg (I-c) and 10 mg menthol dissolved in dichloroethane (0.3 ml) were added and the reaction mixture was heated to 110° C. for 15 minutes. After the reaction mixture was allowed to cool to 23° C., a capillary tube was used to spot the solution on a silica gel TLC plate and was eluted with a 4:1 (v:v) hexanes:ethyl acetate (see FIG. 6C).

Other Substrates for Fluorination with I-c. Decay-Corrected Radiochemical Conversion for the Radiofluorination with I-c Currently Range from 4% to 26%.

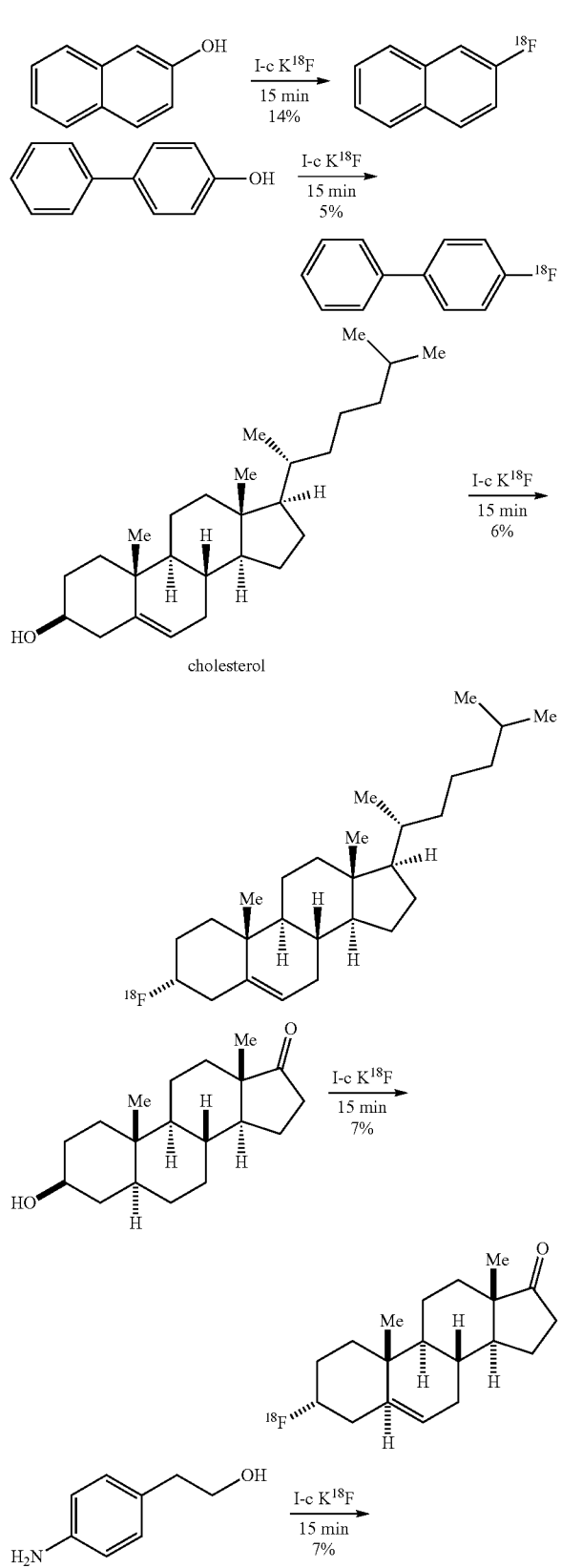

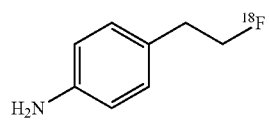

Synthesis of Thiol Containing Derivatives of Formula (I).

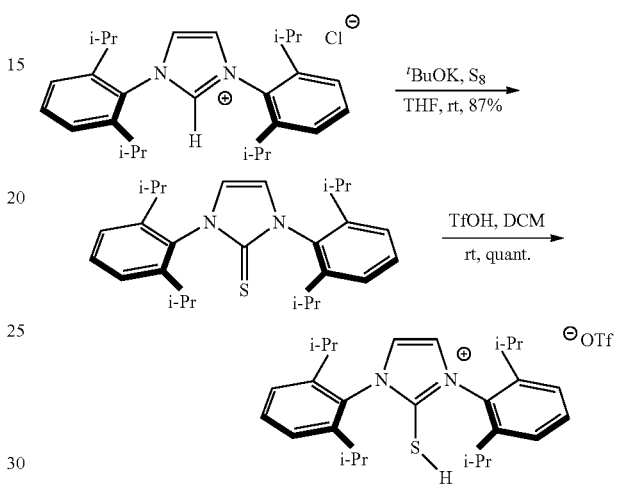

Example 6. Use of Anion Exchange on Chloro Uronium Intermediates for Fluorination of Organic Substrates $^{18}$F-fluoride is prepared as a solution in water, which is subsequently trapped on an ion exchange cartridge and typically eluted with an inorganic base to prepare the $^{18}$F salt of choice as an aqueous solution, which is usually azeotropically dried in the presence of a chelating agent. In order to introduce $^{18}$F as the counteranion of the uronium intermediate, a solution of uronium precursor in an aqueous dioxane solution is used for elution of the activity in a reaction vial, which is capped and heated to 110° C. for 5 min. The radiolabeling procedure is insensitive to air and moisture and the radiolabeled product can be conveniently separated from the reaction precursor. A wide variety of functional groups is tolerated and arenes bearing electron-donating or electron-withdrawing substituents as well as heterocycles undergo radiofluorination in high radiochemical conversion.

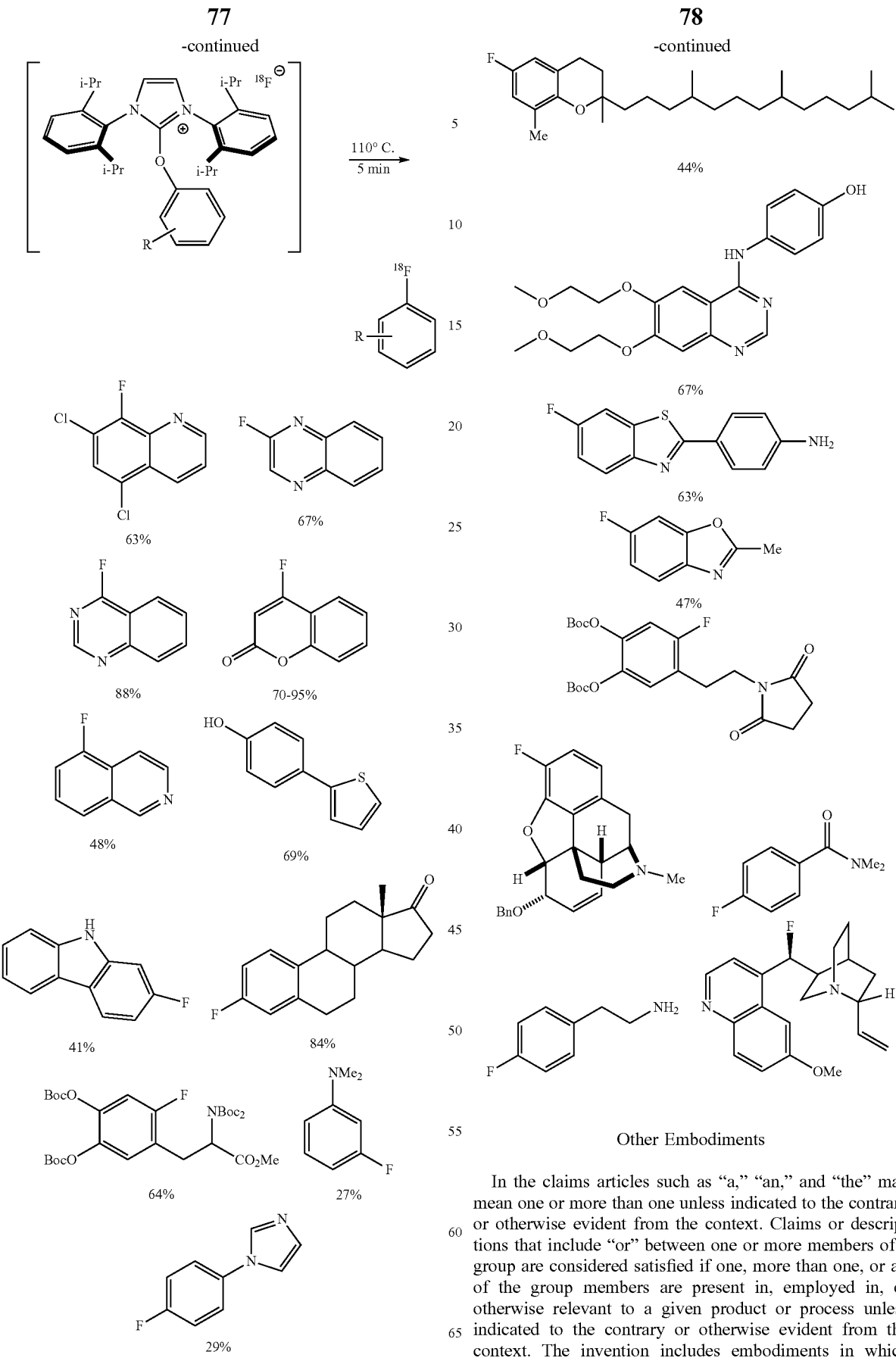

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

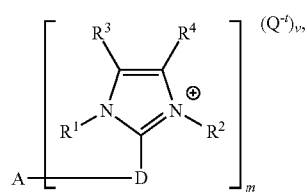

(I)

wherein
D is oxygen;
A is hydrogen, LiX, $MgX_2$, $ScX_3$, $ScR^6{}_3YX_3$, $YR^6{}_3$, $BR^6{}_3$, $BX_3$, $TiX_4$, $TiR^6{}_4$, $ZrX_4$, $ZrR^6{}_4$, $FeX_3$, $FeR^6{}_3$, $ZnX_2$, $ZnR^6{}_2$, $AlX_3$, $AlR^6{}_3$, $InX_3$, $InR^6{}_3$, $SiX_4$, $SiR^6{}_4$, $SnX_2$, $SnR^6{}_2$, $SnX_4$, $SnR^6{}_4$, $BiX_3$, or $BiR^6{}_3$;
each occurrence of $R^6$ is independently $C_{1-6}$ alkyl, —$OR^7$, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, or 3-10 membered carbocyclylalkyl, wherein each of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl is independently optionally substituted with 0 to 5 occurrences of $R^5$;
each occurrence of X is independently halogen or $Q^{-t}$;
$Q^{-t}$ is an anion;
$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is independently optionally substituted with 0 to 5 occurrences of $R^5$;
$R^3$ and $R^4$ are independently selected from the group consisting of hydrogen, unsubstituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —$NH_2$, —$NHR^7$, —$N(R^7)_2$, —OH, —SH, —$SO_2R^7$, —$SOR^7$, —$SO_2N(R^7)_2$, and —$SR^7$;
each occurrence of $R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring;
each occurrence of $R^5$ is independently selected from the group consisting of halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —$NH_2$, —$NHR^7$, —$N(R^7)_2$, —OH, —SH, —$SO_2R^7$, —$SOR^7$, —$SO_2N(R^7)_2$, and —$SR^7$;
t is the anion charge number and is 1, 2, or 3;
v is 0, 1, 2, or 3; and
m is 1, 2, 3, 4, or 5;
provided that the compound is electrically neutral.

2. The compound of claim 1, wherein $R^1$ and $R^2$ are independently $C_{6-10}$ aryl, optionally substituted with 0 to 5 occurrences of $R^5$.

3. The compound of claim 1, wherein the compound is of Formula (I-a):

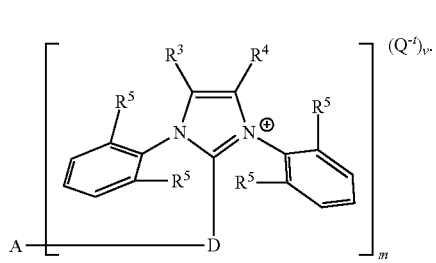
(I-a)

4. The compound of claim 1, wherein the compound is of Formula (I-b):

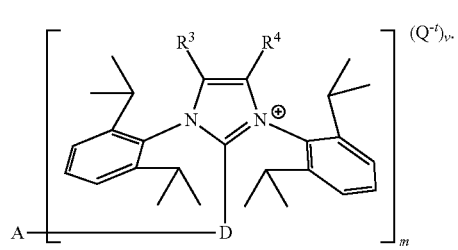
(I-b)

5. The compound of claim 3, wherein A is hydrogen, m is 1, t is 1, and v is 1.

6. The compound of claim 1, wherein both $R^3$ and $R^4$ are hydrogen.

7. The compound of claim 1, wherein the compound is of Formula (I-c):

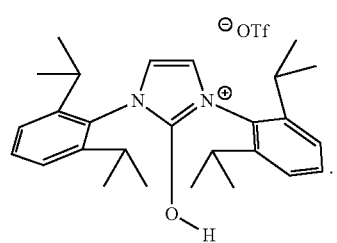
(I-c)

8. The compound of claim 1, wherein $Q^{-t}$ is a halide, trifluoroacetate, trichloroacetate, $NO_2^-$, $NO_3^-$, $H_2PO_4^-$, $PF_6^-$, $HF^{2-}$, $HSO_4^-$, $SbF_6^-$, $ClO_4^-$, $SO_4^{-2}$, $(R^6)SO_3^-$, $OTf^-$, $OTs^-$, $ONf^-$, $ONs^-$, $BF_4^-$, or $B(R^6)_4^-$.

9. The compound of claim 1, wherein A is LiX, $MgX_2$, $ScX_3$, $ScR^6_3YR^6_3$, $BR^6_3$, $BX_3$, $TiX_4$, $TiR^6_4$, $ZrX_4$, $ZrR^6_4$, $FeX_3$, $FeR^6_3$, $ZnX_2$, $ZnR^6_2$, $AlX_3$, $AlR^6_3$, $InX_3$, $InR^6_3$, $SiX_4$, $SiR^6_4$, $SnX_2$, $SnR^6_2$, $SnX_4$, $SnR^6_4$, $BiX_3$, or $BiR^6_3$.

10. A compound of Formula (II) or (II'):

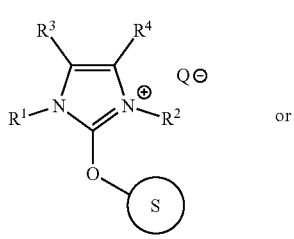
(II)

or

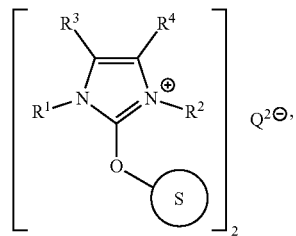
(II')

wherein:
S is an organic substrate;
$Q^{\ominus}$ is $Cl^-$, $Br^-$, or $NO_3^-$;
$Q^{2\ominus}$ is $SO_4^{2-}$;
$R^1$ and $R^2$ are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is independently optionally substituted with 0 to 5 occurrences of $R^5$;
$R^3$ and $R^4$ are independently selected from the group consisting of hydrogen, optionally substituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-NH_2$, $-NHR^7$, $-N(R^7)_2$, $-OH$, $-SH$, $-SO_2R^7$, $-SOR^7$, $-SO_2N(R^7)_2$, and $-SR^7$;
each occurrence of $R^7$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^7$ groups are taken together with their intervening atoms to form an optionally substituted heterocyclic ring; and
each occurrence of $R^5$ is independently selected from the group consisting of halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, $-NH_2$, $-NHR^7$, $-N(R^7)_2$, $-OH$, $-SH$, $-SO_2R^7$, $-SOR^7$, $-SO_2N(R^7)_2$, and $-SR^7$.

11. A compound of Formula (V):

(V)

wherein:
S is an organic substrate;
R¹ and R² are independently selected from the group consisting of $C_{1-6}$ alkyl, $C_{6-10}$ aryl, $C_{6-10}$ aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each of which is independently optionally substituted with 0 to 5 occurrences of $R^5$;
R³ and R⁴ are independently selected from the group consisting of hydrogen, optionally substituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —NH₂, —NHR⁷, —N(R⁷)₂, —OH, —SH, —SO₂R⁷, —SOR⁷, —SO₂N(R⁷)₂, and —SR⁷;
each occurrence of R⁷ is independently selected from the group consisting of hydrogen, acyl, optionally substituted aliphatic, optionally substituted carbocyclyl, optionally substituted heterocyclyl, optionally substituted aryl, and optionally substituted heteroaryl, or two R⁷ groups are taken together with their intervening atoms to form an optionally substituted heterocyclic ring; and
R⁵ is independently selected from the group consisting of halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, optionally substituted $C_{6-10}$ aryl, optionally substituted 5-10 membered heteroaryl, optionally substituted 4-10 membered heterocyclyl, optionally substituted 3-10 membered carbocyclyl, nitro, cyano, acyl, —NH₂, —NHR⁷, —N(R⁷)₂, —OH, —SH, —SO₂R⁷, —SOR⁷, —SO₂N(R⁷)₂, and —SR⁷.

12. The compound of claim 10, wherein the compound is of Formula (VI):

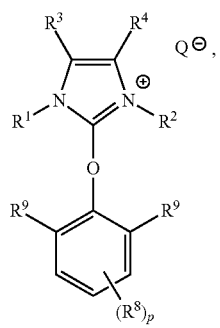

(VI)

wherein:
each occurrence of R⁸ is independently selected from the group consisting of optionally substituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —N(R⁸ᵃ)₂, —OR⁸ᵃ, —CO₂R⁸ᵃ, —SO₂R⁸ᵃ, —SOR⁸ᵃ, —SO₂N(R⁸ᵃ)₂, and —SR⁸ᵃ;

each occurrence of R⁹ is independently selected from the group consisting of optionally substituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, —N(R⁹ᵃ)₂, —OR⁹ᵃ, —CO₂R⁹ᵃ, —SO₂R⁹ᵃ, —SOR⁹ᵃ, —SO₂N(R⁹ᵃ)₂, and —SR⁹ᵃ;

each occurrence of R⁸ᵃ or R⁹ᵃ is independently selected from the group consisting of hydrogen, acyl, optionally substituted aliphatic, optionally substituted carbocyclyl, optionally substituted heterocyclyl, optionally substituted aryl, and optionally substituted heteroaryl, or two R⁸ᵃ or R⁹ᵃ groups are taken together with their intervening atoms to form an optionally substituted heterocyclic ring; and p is 0, 1, 2, or 3.

13. A reaction mixture comprising a compound of Formula (I) of claim 1 and a fluorine source.

14. The compound of claim 10, wherein S is optionally substituted aryl or optionally substituted heteroaryl.

15. The compound of claim 10, wherein compound is of Formula (II):

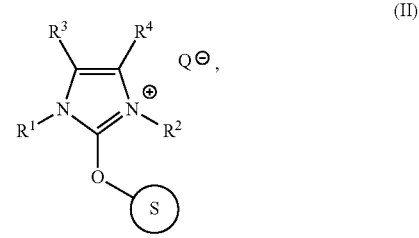

(II)

wherein $Q^{\ominus}$ is Cl⁻.

16. The compound of claim 10, wherein R¹ and R² are independently $C_{6-10}$ aryl, optionally substituted with 0 to 5 occurrences of $R^5$.

17. The compound of claim 10, wherein R³ and R⁴ are hydrogen.

18. The compound of claim 10, wherein the compound is of Formula (II-a):

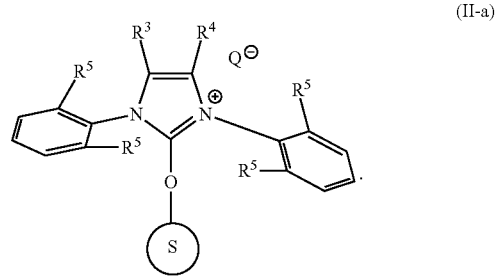

(II-a)

19. The compound of claim 10, wherein the compound is of Formula (II-b):

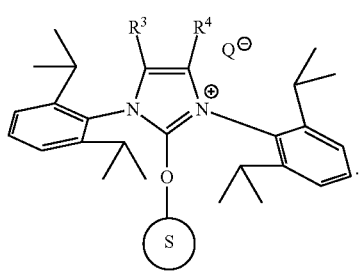
(II-b)

20. The compound of claim 10, wherein the compound is of Formula (II-h):

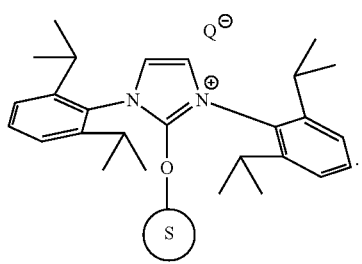
(II-h)

21. The compound of claim 10, wherein the compound is of Formula (II-e):

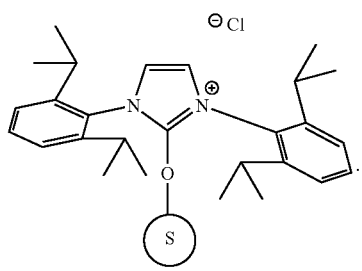
(II-e)

22. The compound of claim 10, wherein:
the compound is of Formula (II-e):

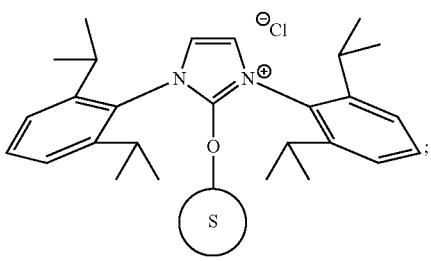
(II-e)

and
S is optionally substituted aryl or optionally substituted heteroaryl.

23. The compound of claim 10, wherein:
the compound is of Formula (II-e):

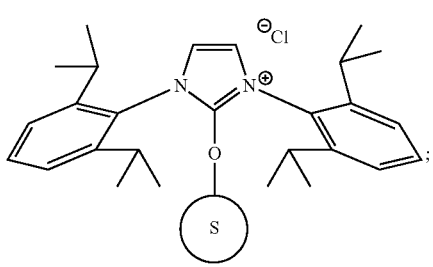
(II-e)

and
S is:

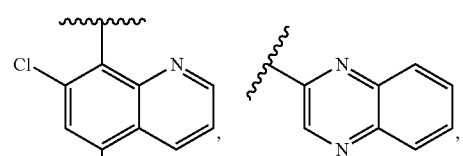

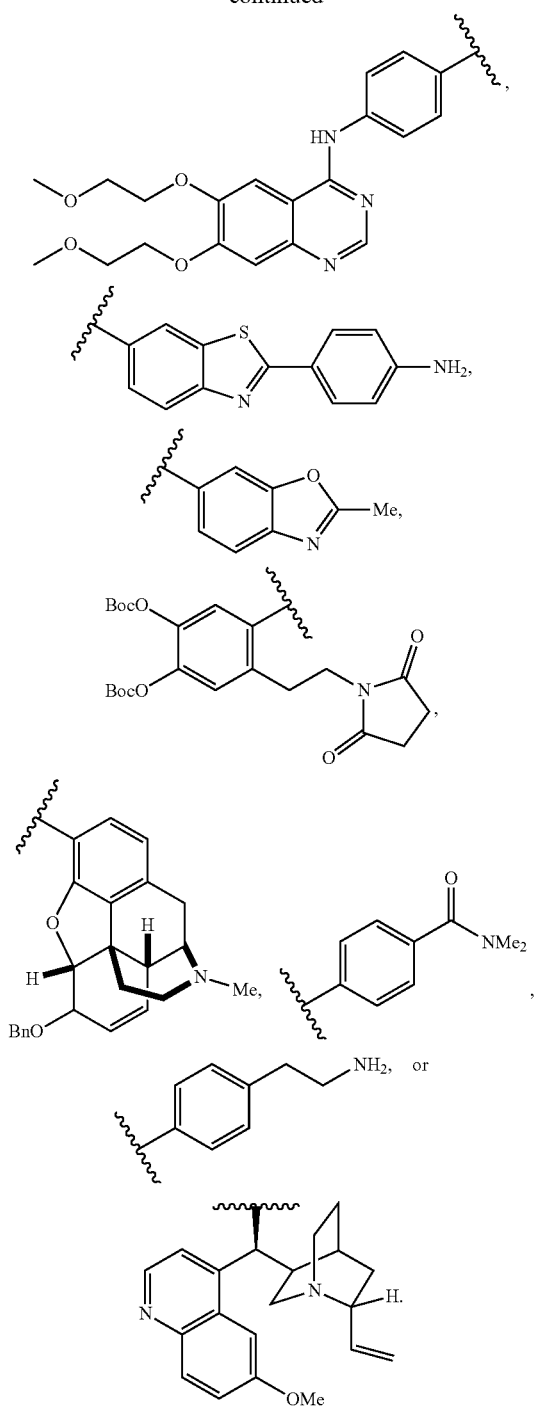

24. The compound of claim 11, wherein S is optionally substituted aryl or optionally substituted heteroaryl.

25. The compound of claim 11, wherein $R^1$ and $R^2$ are independently $C_{6-10}$ aryl, optionally substituted with 0 to 5 occurrences of $R^5$.

26. The compound of claim 11, wherein $R^3$ and $R^4$ are hydrogen.

27. A method of replacing a hydroxyl group on an organic compound with a fluorine atom, the method comprising contacting a compound of Formula (I) of claim 1:

$$\left[ \underset{A\text{—}[\phantom{xx}}{\overset{R^3 \quad R^4}{\underset{R^1}{\text{N}}\underset{}{\overset{\oplus}{\underset{}{\text{N}}}}\text{—}R^2}}\text{—}D]_m \right] (Q^{-t})_v, \quad \text{(I)}$$

with an organic compound under conditions sufficient to replace the hydroxyl group of the organic compound with a fluorine atom, wherein D, A, $Q^{-t}$, $R^1$, $R^2$, $R^3$, $R^4$, t, v, and m are as defined in claim 1.

28. A method of replacing a hydroxyl group on an organic compound with a fluorine atom, the method comprising exchanging $Q^\ominus$ of a compound of Formula (II) of claim 10 or exchanging $Q^{2\ominus}$ of Formula (II') of claim 10:

$$\underset{R^1}{\overset{R^3 \quad R^4}{\text{N}\underset{}{\overset{\oplus}{\text{N}}}\text{—}R^2}}\underset{\text{O—S}}{} \quad Q^\ominus \quad \text{or} \quad \text{(II)}$$

$$\left[\underset{R^1}{\overset{R^3 \quad R^4}{\text{N}\underset{}{\overset{\oplus}{\text{N}}}\text{—}R^2}}\underset{\text{O—S}}{}\right]_2 Q^{2\ominus}, \quad \text{(II')}$$

with a fluoride or $HF_2$ anion, wherein S, $Q^\ominus$, $Q^{2\ominus}$, $R^1$, $R^2$, $R^3$, and $R^4$ are as defined in claim 10.

29. A method of producing a compound of Formula (II) or (II') of claim 10:

$$\underset{R^1}{\overset{R^3 \quad R^4}{\text{N}\underset{}{\overset{\oplus}{\text{N}}}\text{—}R^2}}\underset{\text{O—S}}{} \quad Q^\ominus \quad \text{or} \quad \text{(II)}$$

$$\left[\underset{R^1}{\overset{R^3 \quad R^4}{\text{N}\underset{}{\overset{\oplus}{\text{N}}}\text{—}R^2}}\underset{\text{O—S}}{}\right]_2 Q^{2\ominus}, \quad \text{(II')}$$

the method comprising contacting a compound of Formula (VI) or (VI'):

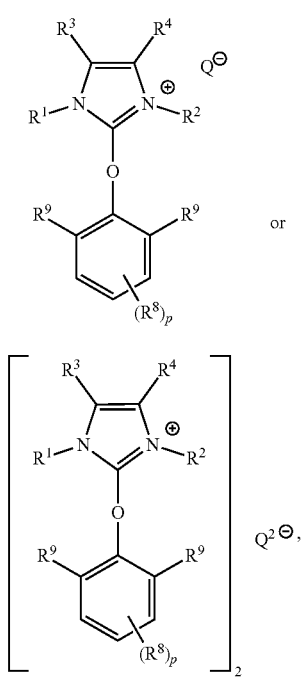

with a hydroxyl group-containing organic substrate and exchanging

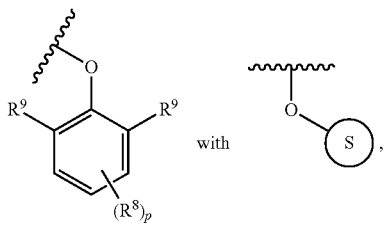

wherein:
S, $Q^\ominus$, $Q^{2\ominus}$, $R^1$, $R^2$, $R^3$, and $R^4$ are as defined in claim 10;
each occurrence of $R^8$ is independently selected from the group consisting of optionally substituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-N(R^{8a})_2$, $-OR^{8a}$, $-CO_2R^{8a}$, $-SO_2R^{8a}$, $-SOR^{8a}$, $-SO_2N(R^{8a})_2$, and $-SR^{8a}$;
each occurrence of $R^9$ is independently selected from the group consisting of optionally substituted $C_{1-6}$ alkyl, optionally substituted $C_{2-6}$ alkenyl, optionally substituted $C_{2-6}$ alkynyl, nitro, cyano, halo, $C_{1-6}$ haloalkyl, $C_{1-6}$ alkoxy, optionally substituted $C_{6-10}$ aryl, optionally substituted $C_{6-10}$ aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, $-N(R^{9a})_2$, $-OR^{9a}$, $-CO_2R^{9a}$, $-SO_2R^{9a}$, $-SOR^{9a}$, $-SO_2N(R^{9a})_2$, and $-SR^{9a}$;
each occurrence of $R^{8a}$ and $R^{9a}$ is independently selected from the group consisting of hydrogen, acyl, optionally substituted aliphatic, optionally substituted carbocyclyl, optionally substituted heterocyclyl, optionally substituted aryl, and optionally substituted heteroaryl, or two $R^{8a}$ or $R^{9a}$ groups are taken together with their intervening atoms to form an optionally substituted heterocyclic ring; and
p is 0, 1, 2, or 3.

30. A method of producing a compound of Formula (I) of claim 1, the method comprising reacting a compound of Formula (I-e):

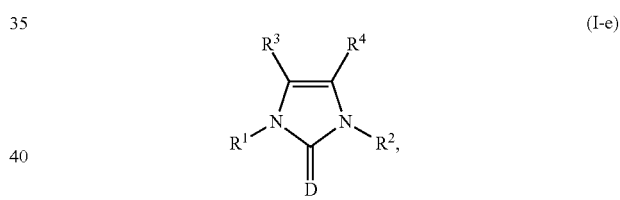

with a Brønsted acid, a Lewis acid, or an acid anhydride to produce the compound of Formula (I), wherein the Lewis acid is LiX, $MgX_2$, $ScX_3$, $ScR^6_3YX_3$, $YR^6_3$, $BR^6_3$, $BX_3$, $TiX_4$, $TiR^6_4$, $ZrX_4$, $ZrR^6_4$, $FeX_3$, $FeR^6_3$, $ZnX_2$, $ZnR^6_2$, $AlX_3$, $AlR^6_3$, $InX_3$, $InR^6_3$, $SiX_4$, $SiR^6_4$, $SnX_2$, $SnR^6_2$, $SnX_4$, $SnR^6_4$, $BiX_3$, or $BiR^6_3$; and X, $R^6$, D, $R^1$, $R^2$, $R^3$, and $R^4$ are as defined in claim 1.

* * * * *

UNITED STATES PATENT AND TRADEMARK OFFICE
CERTIFICATE OF CORRECTION

PATENT NO. : 10,759,764 B2
APPLICATION NO. : 15/029602
DATED : September 1, 2020
INVENTOR(S) : Tobias Ritter et al.

It is certified that error appears in the above-identified patent and that said Letters Patent is hereby corrected as shown below:

In the Claims

In Claim 23, at Column 87, Lines 30-40, the formula:

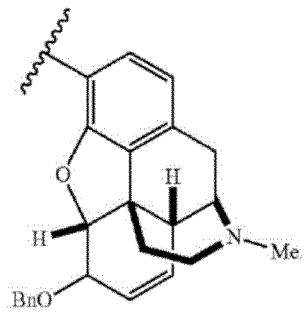

Should be replaced with the formula:

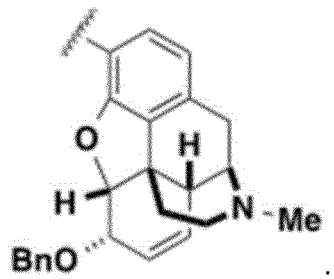

Signed and Sealed this
Twenty-fourth Day of November, 2020

Andrei Iancu
*Director of the United States Patent and Trademark Office*